US008263040B2

(12) United States Patent  
Platzek et al.

(10) Patent No.: US 8,263,040 B2  
(45) Date of Patent: Sep. 11, 2012

(54) METAL CHELATES HAVING A PERFLUORINATED PEG RADICAL, PROCESSES FOR THEIR PREPARATION, AND THEIR USE

(75) Inventors: Johannes Platzek, Berlin (DE); Heiko Schirmer, Berlin (DE); Hanns-Joachim Weinmann, Berlin (DE); Bernd Misselwitz, Glienieke (DE); Ludwig Zorn, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1305 days.

(21) Appl. No.: 11/873,986

(22) Filed: Oct. 17, 2007

(65) Prior Publication Data

US 2008/0159954 A1  Jul. 3, 2008

Related U.S. Application Data

(60) Provisional application No. 60/852,963, filed on Oct. 20, 2006, provisional application No. 60/890,071, filed on Feb. 15, 2007.

(30) Foreign Application Priority Data

Oct. 18, 2006 (DE) .......................... 10 2006 049 821

(51) Int. Cl.  
*A61K 51/00* (2006.01)

(52) U.S. Cl. ..................................... 424/1.73; 424/1.65

(58) Field of Classification Search .................... None  
See application file for complete search history.

(56) References Cited

U.S. PATENT DOCUMENTS

| 4,586,511 | A | 5/1986 | Clark, Jr. |
| 4,588,279 | A | 5/1986 | Fukuchi |
| 4,639,364 | A | 1/1987 | Hoey |
| 5,210,290 | A | 5/1993 | Gries |
| 5,362,478 | A | 11/1994 | Desai et al. |
| 5,567,765 | A | 10/1996 | Moore et al. |
| 5,690,909 | A | 11/1997 | Platzek |
| 5,702,637 | A | 12/1997 | Johnson |
| 5,756,688 | A * | 5/1998 | Snow et al. ............. 534/16 |
| 5,972,241 | A | 10/1999 | Johnson et al. |
| 6,083,479 | A | 7/2000 | Platzek |
| 6,461,587 | B1 | 10/2002 | Platzek |
| 6,468,502 | B1 | 10/2002 | Platzek |
| 6,495,118 | B1 | 12/2002 | Platzek |
| 6,641,797 | B2 | 11/2003 | Platzek et al. |
| 6,676,928 | B2 * | 1/2004 | Platzek et al. ............. 424/9.363 |
| 6,916,461 | B2 | 7/2005 | Platzek |
| 7,226,578 | B2 | 6/2007 | Platzek et al. |
| 7,344,704 | B2 | 3/2008 | Misselwitz et al. |
| 2002/0076379 | A1 | 6/2002 | Platzek |
| 2002/0076380 | A1 | 6/2002 | Platzek |
| 2003/0064026 | A1 | 4/2003 | Platzek |
| 2005/0228347 | A1 | 10/2005 | Verkaart |
| 2006/0093554 | A1 | 5/2006 | Platzek |

FOREIGN PATENT DOCUMENTS

| CA | 2 418 790 | 2/1993 |
| CA | 2205170 | 5/1996 |
| CA | 2 419 259 | 2/2002 |
| CA | 2 419 223 | 2/2003 |
| CA | 2 560 544 | 8/2005 |
| DE | 40 08 179 | 9/1991 |
| DE | 42 03 254 | 8/1993 |
| DE | 43 17 588 A1 | 12/1994 |
| DE | 196 03 033 | 7/1997 |
| DE | 197 44 003 | 7/1999 |
| DE | 197 44 004 | 7/1999 |
| DE | 199 14 101 | 10/2000 |
| DE | 100 40 858 | 3/2002 |
| DE | 100 40 381 C1 | 6/2002 |
| DE | 199 48 651 A1 | 7/2003 |
| EP | 0 292 306 | 11/1988 |
| EP | 0 307 863 | 3/1989 |
| EP | 0 628 316 | 12/1994 |
| JP | 2004 101881 A | 4/2004 |
| WO | WO 90/14846 | 12/1990 |
| WO | WO 93/07907 | 4/1993 |
| WO | WO 94/05335 | 3/1994 |
| WO | WO 94/22368 | 10/1994 |
| WO | WO 95/31965 A | 11/1995 |
| WO | WO 96/15092 A | 5/1996 |
| WO | WO 96/33251 A | 10/1996 |
| WO | WO 99/01161 A1 | 1/1999 |
| WO | WO 99/17809 | 4/1999 |
| WO | WO 02/13874 A | 2/2002 |
| WO | WO 02/13875 A | 2/2002 |
| WO | WO 02/14309 A | 2/2002 |
| WO | WO 03/086474 A | 10/2003 |
| WO | WO 2005/ 072780 A | 8/2005 |

OTHER PUBLICATIONS

Entry for "free radical". 2002 Hawley's Chemical Dictionary, 14th edition.*  
Mohs AM, Zong Y, Guo J, Parker DL, Lu ZR. Peg-g-poly(GdDTPA-co-L-cystine): effect of PEG chain length on in vivo contrast enhancement in MRI. 2005 Biomacromolecules 6: 2305-2311.*  
Database CA [Online] Chemical Abstracts Service, Columbus, Ohio, US; Eleev, A.F. et al: "Antiwear additives for lubricants and fuels" (Jun. 20, 2003).  
Database CA [Online] Chemical Abstracts Service, Columbus, Ohio, US; Romanov, D.V.et al: "Preparation of Chelate-Forming Dibenzo-Containing Five-Membered Cyclic Compounds With Two Symmetric Fluorinated .Beta .-Dicarbonyl Substituents and Their Chelation of Europium for Use in Luminescence Immunoassay", (Apr. 10, 2007).

(Continued)

Primary Examiner — Michael G Hartley  
Assistant Examiner — Jennifer Lamberski  
(74) Attorney, Agent, or Firm — Millen, White, Zelano & Branigan, P.C.

(57) ABSTRACT

The invention relates to the subjects characterized in the patent claims, namely metal chelates having a perfluorinated PEG radical, processes for their preparation, and their use, processes for their preparation and their use in NMR and X-ray diagnosis, radiodiagnosis and radiotherapy, and in MRT lymphography.

31 Claims, 3 Drawing Sheets

OTHER PUBLICATIONS

PCT International Search Report of International Publication issued Dec. 4, 2007, in WO 2008/046463, International Publication Date: Apr. 24, 2008; International Application No. PCT/EP2007/007284; International Filing Date: Aug. 11, 2007. Applicant: Bayer Schering Pharma AG.

Takeshi, H. "Dry Imaging Material", English Abstracts of Japanese Patent Publication No. 2004101881, Publication Date: Apr. 2, 2004, Application No: 2002263866, Application Date: Sep. 10, 2002, Applicant: Konica Minolta Holdings, Inc. (Patent Abstracts of Japan).

Takeshi, H. "Dry imaging material for medical treatment has structural layer(s) containing silver particles, organic silver salt, reducer, binder and electroconductive organic conductive polymer", English translation of Japanese Patent Publication No. 2004101881, Publication Date: Apr. 2, 2004, Application No. 2002263866, Application Date: Sep. 10, 2002, Applicant: Konica Minolta Holdings, Inc. (Thomson Innovation Record Review).

Romanov, D.V. et al. "Preparation of chelate-forming dibenzo-containing five-membered cyclic compounds with two symmetric fluorinated .beta.-dicarbonyl substitutents and their chelation of europium for use in luminescence immunoassay", Database CA [Online] Chemical Abstracts Service, Database Accession No. 2007:400431, HCAPLUS, Caesar Accession No. 1122 (2007).

English Translation of PCT International Preliminary Report on Patentability issued Sep. 19, 2008 in International Application No. PCT/EP2007/007284, International Filing Date: Aug. 11, 2007. International Publication: WO 2008/046463. Applicant: Bayer Schering Pharma AG.

English Translation of German Patent/Publication DE 4203254A1. "Fluorhaltige nuclearmagnetic resonance probe and their use" by H. Tiedtke, et al. Applicant: Max-Planck-Gesellschaft (Thomson Innovation Record Review), Publication date: Aug. 12, 1993.

English Translation of International Publication No. WO 1999/01161, International Publication Date: Jan. 14, 1999. International Application No. PCT/EP1998/03143, International Filing Date: May 28, 1998. Applicant: Schering AG.

* cited by examiner

Title substance from Example 2c ; 50 µmol/kg i.v.; T1-TSE, TR/TE 451/8.7 ms, TA 4:48;

Rat having stimulated lymph nodes; arrows: popliteal lymph nodes

Title substance from Example 2l c; 50 μmol/kg i.v.;T4TSE, TR/TE 451/8.7 ms, TA 4:48;
Rat having stimuated lymph nodes; arrows: popliteal lymph nodes Title substance from Example 22 c : 50 µmol/kg i.v.; T1-TSE, TR/TE 451/8.7 ms, TA 4:48;
Rat having stimulated lymph nodes; arrows: popliteal lymph nodes

METAL CHELATES HAVING A PERFLUORINATED PEG RADICAL, PROCESSES FOR THEIR PREPARATION, AND THEIR USE

This application claims the benefit of the filing date of U.S. Provisional Application Ser. No. 60/852,963 filed Oct. 20, 2006, and U.S. Provisional Application Ser. No. 60/890,071 filed Feb. 15, 2007, both of which are incorporated by reference herein.

The invention relates to the items characterized in the patent claims, namely metal chelates having a perfluorinated PEG radical, processes for their preparation, and their use, processes for their preparation and their use in NMR and X-ray diagnosis, radio-diagnosis and radiotherapy, and in MRT lymphography. The metal chelates having a perfluorinated PEG radical are used in magnetic resonance tomography (MRT) for the demonstration of various physiological and pathophysiological structures and thus for improvement of the diagnostic information, namely the location and the degree of illness, selection and outcome assessment of a targeted therapy and for prophylaxis. The compounds according to the invention are very particularly suited for lymphography, for tumour diagnosis and for infarct and necrosis imaging and are distinguished by outstanding tolerability.

In the field of nuclear magnetic resonance, a few fluorine-containing compounds are known which can be used in the area of imaging. Usually such compounds, however, are only proposed for use in fluorine-19 imaging and are only suitable for this use. Such compounds are disclosed, for example, in U.S. Pat. No. 4,639,364 (Mallinckrodt), DE 4203254 (Max-Planck-Gesellschaft), WO 93/07907 (Mallinckrodt), U.S. Pat. No. 4,586,511 (Children's Hospital Medical Center), EP 307863 (Air Products), U.S. Pat. No. 4,588,279 (University of Cincinnati, Children's Hospital Research Foundation) and WO 94/22368 (Molecular Biosystems).

Further fluorine-compounds which can be employed for imaging are disclosed in U.S. Pat. No. 5,362,478 (VIVORX), U.S. Pat. No. 4,586,511, DE 4008179 (Schering), WO 94/05335 and WO 94/22368 (both Molecular Biosystems), EP 292 306 (TERUMO Kabushiki Kaisha), EP 628 316 (TERUMO Kabushiki Kaisha) and DE 4317588 (Schering).

While no interactions take place between the two nuclei in compounds which contain the elements fluorine and iodine, in compounds which contain fluorine and para-magnetic centres (free radicals, metal ions), an intensive interaction takes place, which is manifested in a reduction of the relaxation time of the fluorine nucleus. The size of this effect depends on the number of unpaired electrons of the metal ion ($Gd^{3+}$>$Mn^{2+}$>$Fe^{3+}$>$Cu^{2+}$) and on the distance between the paramagnetic ion and the $^{19}F$ atom.

The more unpaired electrons of the metal ion which are present and the closer these are brought to the fluorine, the greater the reduction of the relaxation time of the fluorine nucleus.

The reduction of the relaxation time as a function of the distance from the para-magnetic ion makes itself noticeable in all nuclei of uneven spin number, thus also in the proton, and gadolinium compounds are therefore widely used as contrast agents in magnetic resonance tomography MAGNEVIST®, PROHANCE®, OMNISCAN®, DOTAREM®.

In $^1H$ MR imaging ($^1H$ MRI), however, the relaxation time $T^1$ or $T^2$ of the protons, that is especially of the protons of water, and not the relaxation time of the fluorine nuclei is measured and used for the imaging. The quantitative measure of the reduction of the relaxation time is the relaxivity [L/mmol·s]. For reduction of the relaxation times, completes of para-magnetic ions are employed with success. The relaxivity of some commercial preparations is stated in the following table:

|  | $T^1$ relaxivity in water [L/mmol · s, 39° C., 0.47 T] | $T^1$ relaxivity in plasma [L/mmol · s, 39° C., 0.47 T] |
|---|---|---|
| MAGNEVIST ® | 3.8 | 4.8 |
| DOTAREM ® | 3.5 | 4.3 |
| OMNISCAN ® | 3.8 | 4.4 |
| PRO HANCE ® | 3.7 | 4.9 |

In these compounds, only interactions between the protons and the gadolinium ion take place. For these contrast agents in water, a relaxivity of about 4 [L/mmol·s] is thus observed.

Thus, both fluorine compounds for fluorine-19 imaging in which the reduced relaxation time of the fluorine nucleus is utilized, and non-fluorine-containing compounds in which the relaxation time of the protons of the water is measured, are used successfully for MR imaging.

On the introduction of a perfluorocarbon-containing radical into a paramagnetic contrast agent, that is on the combination of properties which hitherto were only known as suitable for fluorine-imaging compounds with compounds which were used for proton imaging, the relaxivity relating to the protons of the water surprisingly also increases rapidly. It achieves values of 10-50 [L/mmol·s] in comparison to values of between 3.5 and 3.8 [L/mmol·s] as have already been listed for some commercial products in the above table.

Perfluoroalkyl-containing metal complexes are already known from DE 196 03 033.1, WO 99/01161, DE 19914101, DE 10040381, DE 10040858. These compounds, however, cannot be employed satisfactorily for all applications, as the tolerability is usually inadequate. Thus there is still a need for MRT contrast agents which have both outstanding imaging properties and are simultaneously excellently tolerable in order to maintain the non-invasive character of the diagnosis method. This is important, for example, if tumours including remote metastases are to be diagnosed and thus a distribution of the contrast agent over the entire body is to be achieved.

Malignant tumours metastasize to an increased extent in regional lymph nodes, it also being possible for several lymph node stations to be involved. Thus lymph node metastases are found in approximately 50-69% of all patients having malignant tumours (Elke, Lymphographie [Lymphography], in: Frommhold, Stender, Thurn (eds.), Radiologische Diagnostik in Klinik and Praxis [Radiological Diagnosis in the Clinic and Practice], Volume IV, Thieme Verlag Stuttgart, 7th ed., 434-496, 1984). The diagnosis of a metastatic attack on lymph nodes is of great importance with respect to the therapy and prognosis of malignant diseases. Using the modern imaging methods (CT, US and MRI), lymphogenous colonies of malignant tumours are only inadequately recognized, as usually only the size of the lymph node can be used as a diagnostic criterion. Thus small metastases in non-enlarged lymph nodes (<2 cm) cannot be differentiated from lymph node hyperplasias without malignant attack (Steinkamp et al., Sonographie und Kernspintomographie: Differentialdiagnostik von reaktiver Lymphknoten-vergrößerung und Lymphknotenmetastasen am Hals [Sonography and Magnetic Resonance Tomography: differential diagnosis of reactive lymph node enlargement and lymph node metastases in the neck], Radiol.diagn. 33:158, 1992).

It would be desirable that when using specific contrast agents lymph nodes with metastatic attack and hyperplastic lymph nodes could be differentiated.

Direct X-ray lymphography (injection of an oily contrast agent suspension into a prepared lymph vessel) is known as an only rarely utilized invasive method, which can only demonstrate a few lymphatic drainage stations.

Experimentally, fluorescent-labelled dextrans are also used in animal experiments in order to be able to observe the lymphatic drainage after interstitial application thereof. It is thus common to all customary markers for the demonstration of lymph passages and lymph nodes after interstitial/intracutaneous administration that they are substances of particulate character ("particulates", e.g. emulsions and nanocrystal suspensions) or large polymers (see also WO 90/14846). On account of their deficient local and systemic tolerability and their low lymph accessibility, which causes an inadequate diagnostic efficiency, the preparations described hitherto, however, still do not prove optimal for indirect lymphography.

As the demonstration of lymph nodes is of central importance for the early recognition of metastatic attack in cancer patients, there is a great need for lymph-specific contrast agent preparations for the diagnosis of corresponding changes in the lymphatic system which are characterized by very good tolerability. The lymphatic system within the meaning of the present invention comprises both the lymph nodes and the lymphatic vessels. The substances of the present invention are therefore suitable for the diagnosis of changes in the lymphatic system, preferably for the diagnosis of changes in the lymph nodes and/or the lymphatic vessels, in particular diagnosis of metastases in the lymph nodes.

A contrast agent loading which is as high as possible and high stability are just as desirable as diagnostically relevant, as uniform as possible lymph enrichment above and beyond several lymph stations. The loading of the entire body should be kept low by rapid and complete excretion of the contrast agent. A rapid onset of action if possible as early as within a few hours after contrast agent administration is of importance for radiological practice. Good systemic tolerability is necessary.

Not least, it is desirable to have available lymph-specific contrast agents which allow both the primary tumour and a possible lymph node metastasis to be demonstrated in one diagnostic session.

Another important area in medicine is the detection, location and monitoring of necroses or infarcts. Thus, myocardial infarction is not a static process, but a dynamic process which extends over a relatively long period (weeks to months). The illness proceeds in approximately three phases which are not sharply separated from one another, but overlapping. The first phase, the development of the myocardial infarct, comprises the 24 hours after the infarction, in which the destruction progresses from the subendocardium to the myocardium (wavefront phenomenon). The second phase, the already existing infarct, comprises the stabilization of the area in which fibre formation (fibrosis) takes place as a healing process. The third phase, the healed infarct, begins after all destroyed tissue is replaced by fibrous scar tissue. During this period extensive restructuring takes place.

To date, no precise and reliable process is known which makes the present phase of a myocardial infarct diagnosable in the living patient. For the assessment of a myocardial infarct, it is of crucial importance to know how large the amount of the tissue lost in the infarct is and in which position the loss took place, since the type of therapy depends on this knowledge.

Infarcts take place not only in the myocardium, but also in other tissues, particularly in the brain.

While the infarct is curable to a certain extent, in the case of necrosis, locally restricted tissue death, only the harmful sequelae for the remainder of the body can be prevented or at least alleviated. Necroses can arise in many ways: by means of injuries, chemicals, oxygen deficit or by radiation. As with the infarct, the knowledge of the extent and type of a necrosis is important for the further medical course of action.

Early on, attempts therefore took place to improve the location of infarcts and necroses by use of contrast agents in non-invasive procedures such as scintigraphy or magnetic resonance tomography. In the literature, the attempts to employ porphyrins for necrosis imaging take up a large space. The results achieved, however, yield an inconsistent picture. Moreover, porphyrins tend to deposit in the skin, which leads to photosensitization. The sensitization can last for days, in fact even weeks. This is an undesirable side effect in the use of porphyrins as diagnostics. Moreover, the therapeutic index for porphyrins is only very small, as, for example, for Mn-TPPS an action commences only at a dose of 0.2 mmol/kg, but the $LD_{50}$ is already 0.5 mmol/kg. Contrast agents for necrosis and infarct imaging not derived from the porphyrin structure are described in DE 19744003 (Schering AG), DE 19744004 (Schering AG) and WO 99/17809 (EPIX). Hitherto, however, there are still no compounds which can be employed satisfactorily as contrast agents in infarct and necrosis imaging.

The same problem is present in the area of the compounds which can be employed in order to diagnose thrombi or atherosclerotic plaques: there are no compounds which can be employed satisfactorily as contrast agents for the demonstration of thrombi or atherosclerotic plaques and are simultaneously characterized by outstanding tolerability.

The object of the invention was therefore to make available contrast agents which on the one hand have outstanding imaging properties as MRT contrast agents, and are suitable in particular for tumour and necrosis imaging and/or lymphography and/or for blood pool imaging and/or for the demonstration of thrombi or atherosclerotic plaques, and are simultaneously distinguished by outstanding tolerability.

The object is achieved by
metal chelates comprising
 a) at least one perfluorinated PEG radical, and
 b) at least one chelator radical, and
 c) at least one metal ion equivalent of atomic number 21-29, 31-33, 37-39, 42-44, 49 or 57-83
and salts thereof.

In a preferred embodiment, the metal chelates contain a perfluorinated PEG radical, and a chelator radical.

In another preferred embodiment, the metal chelates contain a perfluorinated PEG radical, and 2 chelator radicals.

In a particularly preferred embodiment, the present invention relates to metal chelates according to formula I:

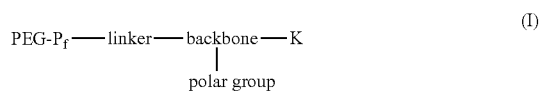

where
PEG-$P_f$ is a perfluorinated PEG radical having 4 to 30 carbon atoms,
linker is a linker group which connects the PEG-$P_f$ radical to the backbone,
backbone is a trivalent radical, K is a chelate radical, consisting of a chelator radical, at least one metal ion equivalent of atomic number 21-29, 31-33, 37-39, 42-44, 49 or 57-83, and in the radical K free acid groups which are optionally present can optionally be present as salts of organic and/or inorganic bases or amino acids or amino acid amides, and polar group is a polar group.

Likewise additionally comprised by the invention are intermediates of the above-mentioned metal chelates, where the intermediates contain a) at least one perfluorinated PEG radical, and
b) at least one chelator radical, where perfluorinated PEG radical and chelator radical have the above-mentioned meaning, and under the assumption that the intermediates contain no metal ion equivalent of atomic number 21-29, 31-33, 37-39, 42-44, 49 or 57-83.

Preferred intermediates of abovementioned metal chelates according to formula I are characterized by formula Ia:

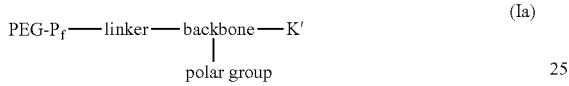

where

PEG-$P_f$ is a perfluorinated PEG radical having 4 to 30 carbon atoms linker is a linker group which connects the PEG-$P_f$ radical to the backbone backbone is a trivalent radical K' is a chelator radical, and polar group is a polar group, under the assumption that the chelator radical is not occupied by a metal ion equivalent of atomic number 21-29, 31-33, 37-39, 42-44, 49 or 57-83.

Particularly preferred embodiments of the intermediates correspond to the preferred embodiments of the metal chelates, with the proviso that the intermediates are not occupied by a metal ion equivalent of atomic number 21-29, 31-33, 37-39, 42-44, 49 or 57-83.

Preferred Embodiments of the Perfluorinated PEG Radical of the Metal Chelates and Intermediates According to the Invention:

In a preferred embodiment, the metal chelates and intermediates contain a perfluorinated PEG radical having 4-30 C atoms, in particular having 4-20 C-atoms.

In a particularly preferred embodiment, the perfluorinated PEG radical is linear. In particular, linear perfluorinated PEG radicals having 6-12 C atoms are preferred, very particularly preferably having 7, 8, 9, 10, or 11 C atoms.

In another particularly preferred embodiment, the perfluorinated PEG radical is branched. In particular, branched perfluorinated PEG radicals having 8-16 C atoms are preferred, very particularly preferably having 9, 10, 11, 12, 13, or 14 C atoms.

In a very preferred embodiment, the PEG radical has the following formula XXI:

$$CF_3-(CF_2)_{n'''}-[-O-(CF_2)_2]_{m'''}-O-(CF_2)- \quad (XXI)$$

where n''' is an integer between 0 and 6, preferably 0, 1, 2 or 3, and m''' is an integer between 1 and 14, preferably 2 and 9, in particular preferably 2, 3, 4 or 5.

Preferred Embodiments of the Chelator Radical of the Metal Chelates and Intermediates According to the Invention:

In a preferred embodiment, the metal chelates and intermediates are characterized in that the chelator radical is cyclic or open-chain.

In a particularly preferred embodiment, the chelator radical is cyclic, in particular the chelator radical is a DOTA radical or a derivative thereof.

Very particularly preferably, the cyclic chelator radical having a complexed metal ion is selected from the following radicals:

chelator radical of the general formula II:

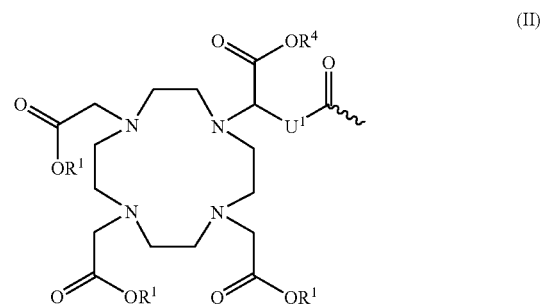

in which $R^1$ is a hydrogen atom or a metal ion equivalent of atomic number 21-29, 31-33, 37-39, 42-44, 49 or 57-83, with the proviso that at least two $R^1$ are metal ion equivalents, $R^4$ is hydrogen or a metal ion equivalent mentioned under $R^1$, and $U^1$ is $-C_6H_4-O-CH_2-\omega-$ or a group $-(CH2)_{p'}-$, where ω is the binding site to —CO— and p' is an integer between 1 and 4;

chelator radicals of the general formula III:

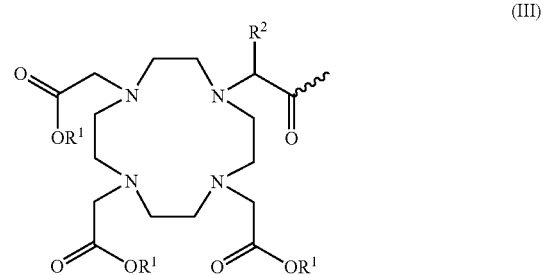

where $R^1$ has the abovementioned meaning, and $R^2$ is hydrogen, $C_1$-$C_7$-alkyl, benzyl, phenyl, $-CH_2OH$ or $-CH_2OCH_3$;

chelator radical of the general formula IV:

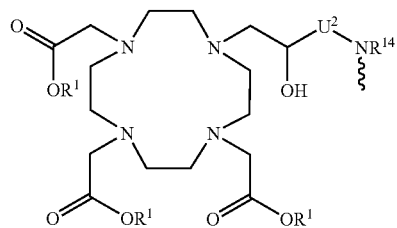

(IV)

in which
R$^1$ has the abovementioned meaning,
R$^{14}$ is H or C$_1$-C$_4$ alkyl, and
U$^2$ is a straight-chain or branched, saturated or unsaturated C$_1$-C$_{20}$ alkylene group optionally comprising imino, phenylene, phenylenoxy, phenylenimino, amide, hydrazide, carbonyl or ester groups, oxygen, sulphur and/or nitrogen atom(s), and is optionally substituted by hydroxyl, mercapto, oxo, thioxo, carboxyl, carboxyalkyl, ester, and/or amino group(s);

chelator radical of the general formula IVa:

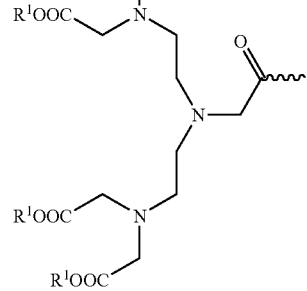

(IVa)

in which
R$^1$ has the abovementioned meaning,
R$^2$ and R$^3$ independently of one another are hydrogen, C$_1$-C$_7$-alkyl, benzyl, phenyl, —CH$_2$OH or —CH$_2$OCH$_3$, and
U is —C$_6$H$_4$—O—CH$_2$-ω-, —(CH$_2$)$_{1-5}$-ω, a phenylene group, —CH$_2$—NHCO—CH$_2$—CH(CH$_2$COOH)—C$_6$H$_4$-ω-, —C$_6$H$_4$—(OCH$_2$CH$_2$)$_{0-1}$—N(CH$_2$COOH)—CH$_2$-ω or a C$_1$-C$_{12}$-alkylene or —(CH$_2$)$_{7-12}$—C$_6$H$_4$—O-group optionally interrupted by one or more oxygen atoms, 1 to 3 —NHCO—, 1 to 3 —CONH groups and/or substituted by 1 to 3 —(CH$_2$)$_{0-5}$COOH groups, where ω is the binding site to —CO—;

chelator radical of the general formula IVb:

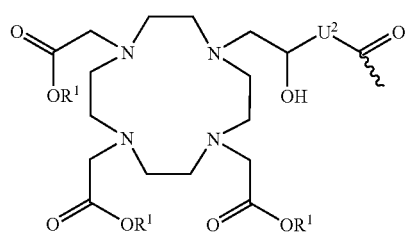

(IVb)

in which
R$^1$ and U$^2$ have the abovementioned meaning;

where free acid groups optionally present in the chelator radical can be present as salts of organic and/or inorganic bases or amino acids or amino acid amides.

The radical U in the chelate K of the general formula IVa is preferably —CH$_2$— or C$_6$H$_4$—O—CH$_2$-ω, where ω is the binding site to —CO—.

In a further preferred embodiment, the chelator radical is open-chain, in particular the radical is a DTPA radical or a derivative thereof, or a chelator based on catecholamide (CAM), terephthalamide (TAM), hydroxypyridone (HOPO) and/or hydroxypyrimidone (HOPY) or derivatives thereof.

In particular, the open-chain chelator radical having a complexed metal ion is selected from the following radicals:

chelator radicals of the general formula Va or Vb:

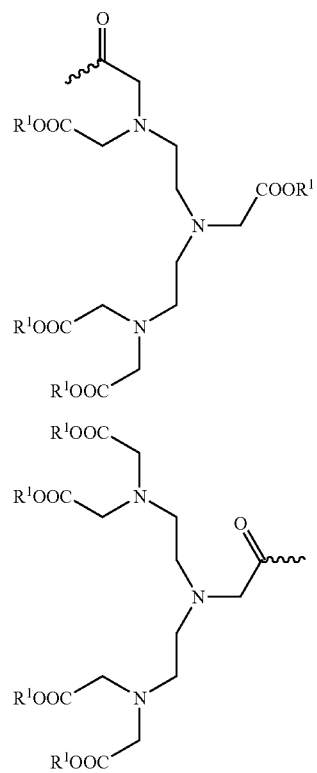

in which R$^1$ has the abovementioned meaning, chelator radicals of the general formula VI:

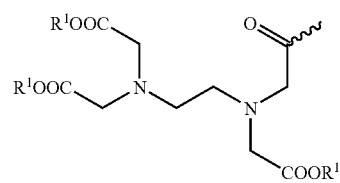

(VI)

in which R$^1$ has the abovementioned meaning, chelator radicals of the general formula VIII:

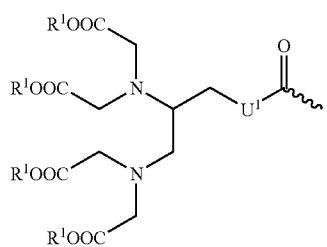
(VII)

in which $R^1$ and $U^1$ have the abovementioned meaning, where ω is the binding site to —CO—;
chelator radicals of the general formula VIII:

$(K^1)_3\text{-}A'\text{-}U'\text{—}$  (VIII), in which $K^1$ independently of one another are a radical

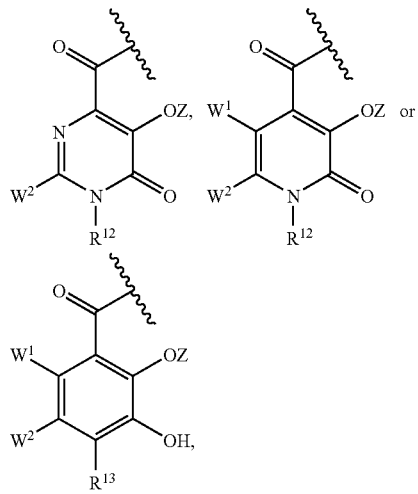

and in which
Z has the meaning of $R^1$,
$R^{12}$ is a hydrogen atom or a straight-chain or branched, saturated or unsaturated $C_{1-10}$-alkyl radical, which is optionally interrupted by 1-3 oxygen atoms, 1-3 nitrogen atoms, 1-2 —CONH— and/or 1-3 —$NR^5$— radicals, is optionally substituted by 1-4 hydroxyl groups, 1-2 carboxyl groups (which are optionally present in protected form), 1-2 —$SO_3H$ groups (which are optionally present in protected form), 1-2 —$PO_3H_2$ groups and/or 1-2 halogen atoms and/or in which optionally 1-2 carbon atoms are present as carbonyl groups, where the alkyl radical or a part of the alkyl radical can be arranged in cyclic form,
$R^{13}$ is a hydrogen atom, a straight-chain or branched, saturated or unsaturated $C_{1-10}$-alkyl radical which is optionally interrupted by 1-3 oxygen atoms, 1-3 nitrogen atoms and/or 1-3 —$NR^5$— radicals, is optionally substituted by 1-2 hydroxyl groups, 1-2 carboxyl groups, 1-2 —$SO_3H$ groups, 1-2 —$PO_3H_2$ groups and/or 1-2 halogen atoms and/or in which optionally 1-2 carbon atoms are present as carbonyl groups, where the alkyl radical or a part of the alkyl radical can be arranged in cyclic form, —COOH, halogen, —$CONR^5R^6$, —$SO_3H$ or —$PO_3H_2$, $R^5$ and $R^6$ independently of one another are a hydrogen atom or a straight-chain, branched or cyclic, saturated or unsaturated $C_{1-10}$-alkyl radical, which is optionally substituted by 1-4 hydroxyl groups or interrupted by 1-2 oxygen atoms,
$W^1$ and $W^2$ independently of one another are a radical $R^1$ or —$CONR^5R^6$,
A' is a radical

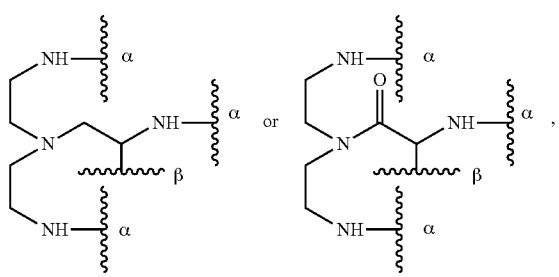

in which the positions α represents the linkages to $K^1$ and the positions β represents the linkages to U', and
U' is a direct bond or a straight-chain, cyclic or branched, saturated or unsaturated $C_{1-20}$-alkylene radical, which is optionally interrupted by 1-3 oxygen atoms, 1-3 sulphur atoms, 1-3 nitrogen atoms, 1-3 —$NR^5$— radicals, 1-3 —NHCO— radicals, 1-3 —CONH— radicals, 1-2 —CO— radicals, 1-3 —O—P—(=O)(—OH)—O— radicals and/or 1-2 arylene radicals, optionally substituted by 1-3 straight-chain, branched or cyclic, saturated or unsaturated $C_{1-6}$-alkyl radicals, 1-3 hydroxyl groups, 1-3 carboxyl groups, 1-3 aryl groups, 1-3 halogen atoms and/or 1-3 —O—$C_{1-6}$-alkyl groups, where the alkyl radical is straight-chain, branched or cyclic, saturated or unsaturated, and/or in which optionally 1-3 carbon atoms can be present as carbonyl groups, where the alkylene radical or a part of the alkylene radicals can be arranged in cyclic form, and 1-4 carbon atom(s) as carbonyl group(s),
chelator radical comprising a scaffold radical are bonded to the 3 radicals of the general formula IX:

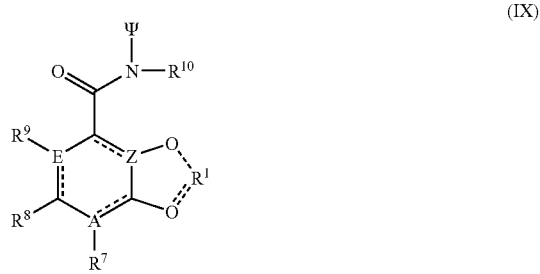
(IX)

where
$R^7$, $R^8$ and $R^9$ independently of one another are selected from H, a linear or branched, $C_1$-$C_6$-alkyl group, which can optionally be interrupted by 1-4 oxygen atoms, 1-4 sulphur atoms, 1-4 nitrogen atoms, 1-4 —$NR^3$— radicals, 1-4 —NHCO— radicals, 1-4 —CONH— radicals, 1-2 —CO— radicals, 1-4 —O—P—(=O)(—OH)— O— radicals and/or 1-2 arylene radicals, is optionally substituted by 1-3 straight-chain, branched or cyclic, saturated or unsaturated $C_{1-10}$-alkyl radicals, 1-3 hydroxyl groups, 1-3 carboxyl groups, 1-3 aryl groups, 1-3 halogen atoms and/or 1-3 —O—$C_{1-6}$-alkyl groups, where the alkyl radical is straight-chain, branched or cyclic, saturated or unsaturated, and/or in which optionally 1-3 carbon atoms can be present as carbonyl groups, where the alkylene radical or a part of the alkylene radical can be present in cyclic form, a substituted or unsubstituted aryl group or aralkyl group, substituted or unsubstituted $C_1$-$C_6$-heteroalkyl group, or hydroxyl, carboxyl, amide, ester and amino groups, where, if A is nitrogen, then $R^7$ can be different from amino and if E is nitrogen, then $R^9$ is not present, and where for one of the 3 radicals according to formula (IX) $R^7$ or $R^8$ or $R^9$ is a divalent group which connects the chelator radical (having a complexed metal ion) to the backbone, $R^{10}$ is a group selected from H, a substituted or unsubstituted $C_1$-$C_6$-alkyl group, a substituted or unsubstituted aryl group, substituted or unsubstituted $C_1$-$C_6$-heterolkyl group, or hydroxyl groups, carboxyl groups, amide groups, and ester groups, and A, E and Z independently of one another are selected from carbon and nitrogen ψ is the bond to the scaffold, and at least 3 of the radicals of the formula (IX) must be present in order to form a chelator within the meaning of the present invention, where these 3 radicals can be identical or different.

A preferred scaffold is a triethylenamine radical of the following formula:

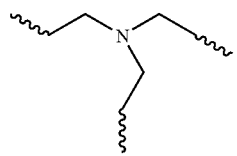

Chelator radicals resulting therefrom are TREN derivatives.

Particularly preferred chelator radicals are TREN-bis-HOPO-TAM radicals and derivatives thereof, TREN-tris-HOPO radicals, TREN-bis-HOPO-HOPY radicals, TREN-tris-HOPY, TREN-bis-HOPY-TAM radicals.

In a preferred embodiment, for one of the 3 radicals according to formula (IX) $R^7$ is a divalent group which connects the chelator radical with complexed metal ion to the backbone.

In a particularly preferred embodiment, the 3 radicals according to formula (IX) are selected from the following radicals:

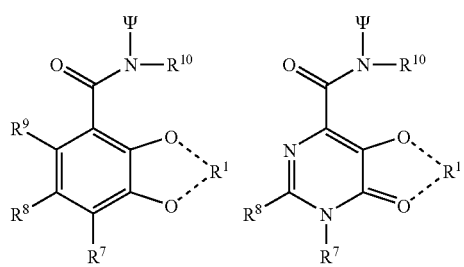

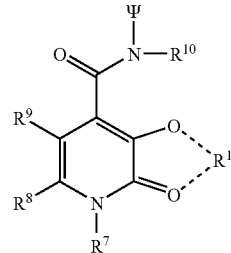

Particularly preferred TREN-bis-HOPO-TAM radicals are of the following formula:

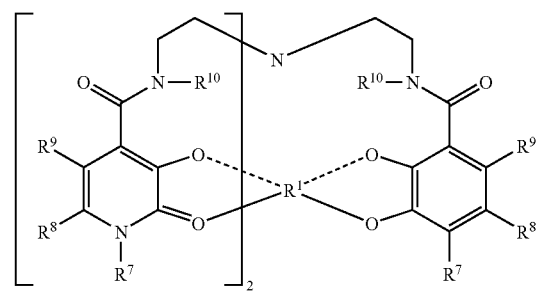

Especially preferred are those TREN-bis-HOPO-TAM radicals, in which the $R^7$ of the TAM radical is a divalent group which connects the chelator radical with complexed metal ion to the backbone.

In a particularly preferred embodiment, the divalent group which connects the chelator radical with complexed metal ion to the backbone is a group —C(O)—.

In another preferred embodiment, R8 and R9 independently of one another are H or C1-C4-alkyl groups or C1-C6-hydroxyalkyl groups Particularly preferred compounds are those with the chelate K of the general formula IVa.

In a preferred embodiment, $U^2$ is a $C_1$-$C_6$ alkylene chain, which is optionally interrupted by 1 to 2 —NHCO— groups and/or 1 to 1 O— atoms, and which can be substituted by 1 to 3 —OH groups.

The radical $U^2$ in the metal complex K is especially preferably a linear alkylene group having 1 to 6 C atoms, in particular 2, 3 or 4 C atoms, or a linear alkylene group having 1 to 6 C— atoms, in particular 2, 3 or 4 C— atoms, which is interrupted by 1O atom, or a linear alkylene group having 1 to 6 C— atoms, in particular 2, 3 or 4 C atoms, which contains an —NHCO— group.

In a particularly preferred embodiment, $U^2$ is an ethylene group.

The alkyl groups $R^2$ and $R^3$ in the macrocycle of the general formula IVa can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, 1,2-dimethylpropyl may be mentioned. Preferably, $R^2$ and $R^3$ are independently of one another hydrogen or $C_1$-$C_4$-alkyl.

In a very particularly preferred embodiment, $R^2$ is methyl and $R^3$ is hydrogen.

The benzyl group or the phenyl group $R^2$ or $R^3$ in the chelate K of the general formula IVa can also be substituted in the ring.

The compounds of the formula VIII and IX according to the invention comprise catechol radicals. These radicals contribute a coordinated metal ion to the coordination or to the charge equalization. Therefore Z is either a hydrogen atom or a metal ion equivalent.

The hydroxypyridinone or hydroxypyrimidone radical, which can be $K^1$ in the general formula VIII, in a preferred embodiment carries a substituent $R^{12}$, which is a hydrogen atom or a straight-chain or branched, saturated or unsaturated $C_{1-10}$-alkyl radical, which is optionally interrupted by 1-3 oxygen atoms, 1-3 nitrogen atoms and/or 1-3 —$NR^5$— radicals, is optionally substituted by 1-4 hydroxyl groups, 1-2 carboxyl groups (which are optionally present in protected form), 1-2 —$SO_3H$ groups (which are optionally present in protected form), 1-2 —$PO_3H_2$— groups and/or 1-2 halogen atoms and/or in which optionally 1-2 carbon atoms are present as carbonyl groups, where the alkyl radical or a part of the alkyl radical can be arranged in cyclic form.

Preferably, $R^{12}$ is a hydrogen atom or a straight-chain or branched, preferably straight-chain $C_{1-5}$-alkyl radical, which can be interrupted by 1-2 oxygen atoms or by 1-2 —CONH— and/or can be substituted by 1-4 hydroxyl groups, a carboxyl group and/or a group —$SO_3H$. Preferred examples of $R^{12}$ are —H, —$CH_2$—CO—$NH_2$, —$CH_3$, —$CH_2$—$CH_3$, —$CH_2$—$CH_2$—$CH_3$, —CH($CH_3$)—$CH_3$, —C($CH_3$)($CH_3$)—$CH_3$, —$CH_2$—OH, —$CH_2$—$CH_2$—OH, —$CH_2$—$CH_2$—O—$CH_3$, —$CH_2$—COOH, —$CH_2$—COOt-But, —$CH_2$—COO$CH_2$—$C_6H_5$, —$CH_2$—$CH_2$—$SO_3H$, —$CH_2$—$CH_2$—$CH_2$—$SO_3H$, —$CH_2$—$CH_2$—$CH_2$—$CH_2$—$SO_3H$, —$CH_2$—CH(OH)—$CH_2$—OH, —$CH_2$—$CH_2$—O—$CH_2$—$CH_2$—O—$CH_3$, —$CH_2$—$CH_2$—O—$CH_2$—$CH_2$—OH, —$CH_2$—$CH_2$—O—$CH_2$—COOH and —CH[$CH_2$—O—CH—($CH_2$—OH)$_2$]$_2$, —H, methoxyethyl, methyl, —$CH_2$—CO—$NH_2$ and —$CH_2$—COOH, in particular —$CH_2$—CO—$NH_2$, methoxyethyl and methyl, are particularly preferred.

$W^1$ and $W^2$ independently of one another are a radical $R^{12}$, where $R^{12}$ is as defined above and also comprises the above preferred radicals. Particularly preferably, $W^1$ and $W^2$ independently are a hydrogen atom or a straight-chain or branched, preferably straight-chain $C_{1-5}$-alkyl radical, in particular a hydrogen atom or a methyl radical. For example, one of $W^1$ and $W^2$ can be a hydrogen atom and the other of $W^1$ and $W^2$ can be a methyl radical, or $W^1$ and $W^2$ can both be a hydrogen atom.

The catechol radical, which can alternatively be $K^1$ in the formula VIII, carries a substituent $R^{13}$. This can be a hydrogen atom, a straight-chain or branched, saturated or unsaturated $C_{1-10}$-alkyl radical, which is optionally interrupted by 1-3 oxygen atoms, 1-3 nitrogen atoms and/or 1-3 —$NR^5$— radicals, is optionally substituted by 1-2 hydroxyl groups, 1-2 carboxyl groups, 1-2 —$SO_3H$ groups, 1-2 —$PO_3H_2$ groups and/or 1-2 halogen atoms and/or in which optionally 1-2 carbon atoms are present as carbonyl groups, where the alkyl radical or a part of the alkyl radical can be arranged in cyclic form, —COOH, halogen, —CON$R^5R^6$, —$SO_3H$ or —$PO_3H_2$. Preferred alkyl radicals and alkyl radicals which are substituted and interrupted by heteroatoms for $R^{13}$ are those as described above for $R^3$. Fluorine, chlorine, bromine and iodine are suitable as a halogen.

The above radicals $R^5$ and $R^6$ independently of one another are a hydrogen atom or a straight-chain, branched or cyclic, saturated or unsaturated $C_{1-6}$-alkyl radical which is optionally substituted by 1-2 hydroxyl groups. Suitable $C_{1-6}$-alkyl radicals for $R^5$ and $R^6$ are in particular methyl, ethyl, propyl, isopropyl, n-butyl, isobutyl, tert-butyl, pentyl, hexyl, cyclohexyl, 2-hydroxyethyl and —CH[$CH_2$—O—CH—($CH_2$—OH)$_2$]$_2$.

In one embodiment of the present invention, U' in the formula (VIII) is a phenylene or cyclohexylene radical or a straight-chain or branched, saturated $C_{1-10}$-alkylene radical, which can be interrupted by an oxygen atom, an —$NR^5$— radical, one or two amide radical(s) and/or a phenylene radical and in which one or two carbon atom(s) can be present as carbonyl group(s). A straight-chain or branched, saturated $C_{1-4}$-alkylene radical in which one or two carbon atom(s) are present as carbonyl group(s) is very particularly preferred.

For example, U' can be selected from the group consisting of —$CH_2$—$CH_2$—CO—, —$CH_2$—$CH_2$—CO—NH—$CH_2$—$CH_2$—CO—, —$CH_2$—CO—NH—$CH_2$—CO—, —CH($CH_3$)—CO—NH—$CH_2$—CO—NH—$CH_2$—$CH_2$—CO—, —($CH_2$)$_4$—CO—, —($CH_2$)$_4$—NH—CO—$CH_2$—$CH_2$—CO— and —($CH_2$)$_4$—NH—CO—$CH_2$—O—$CH_2$—CO—, where these radicals are bonded left of A' in the reading direction and right of the backbone radical in the reading direction.

The radicals of the formula (VIII) and their preparation are known from DE 102004062258.2.

The radicals of the formula (IX) and their preparation are known from WO 03/016923.

Preferred Embodiments for the Linker of Metal Chelates According to the Invention (According to Formula I) and Intermediates (According to Formula Ia):

In a preferred embodiment, the linker is a carbon chain having 1-15 C atoms, which can be linear or branched, saturated or unsaturated, and which is optionally interrupted by 1-5 oxygen atoms, 1-3 —NHCO— groups, 1-3 —CONH— groups, 1-2 sulphur atoms, 1-4 —NH— groups and/or 1-2 phenylene groups, which can optionally be substituted by 1-2 OH groups, 1-2 NH2 groups, 1-2-COOH groups, or 1-2 —SO3H groups, and which is optionally substituted by 1-6 OH groups, 1-5 —COOH groups (which are optionally present in protected form), 1-2 SO3H groups (which are optionally present in protected form), 1-3 NH2 groups and/or 1-3 $C_1$-$C_4$-alkoxy groups.

In a particularly preferred embodiment, the linker is a group of the formula X:

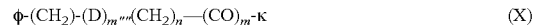

where

D is O or S, n is an integer between 1 and 15, m and m'''' independently of one another are either 0 or 1, φ is the binding site of the linker to PEG-Pf, and κ is the binding site of the linker to the backbone.

In a preferred embodiment of the linker according to formula X, m=0 and n=2-4, especially preferably n=2.

In a further preferred embodiment D is oxygen.

In another preferred embodiment, m=1 and n=1-3.

Preferably, m'''' is 1.

Preferred Embodiments for the Backbone of Metal Chelates According to the Invention (According to Formula I) and Intermediates (According to Formula Ia):

In a preferred embodiment, backbone is a phosphorus- and/or nitrogen-containing radical, especially preferably a nitrogen-containing radical, very particularly preferably a nitrogen-containing radical selected from: amino acids having a functional side chain such as aspartic acid, glutamic acid, serine, cysteine, ornithines, lysines and 2,4-diaminobutyric acid, and an alkylenediamine radical and derivatives thereof, nitrogen and 3,5-diaminobenzoic acid.

In a particularly preferred embodiment, the backbone is selected from the following groups XIa to XIm:

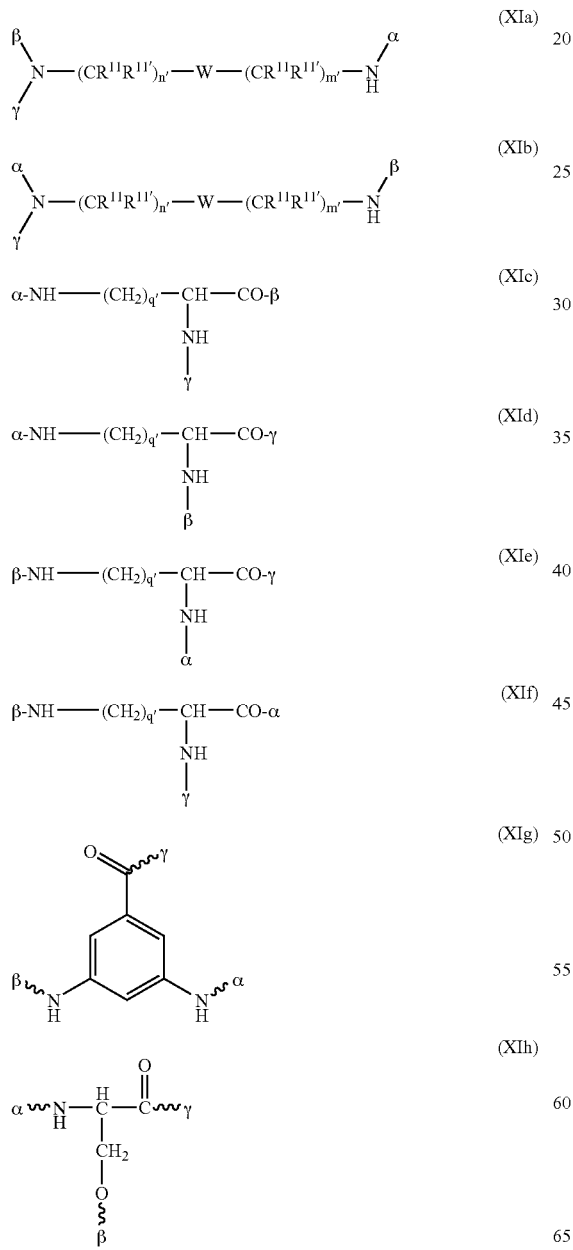

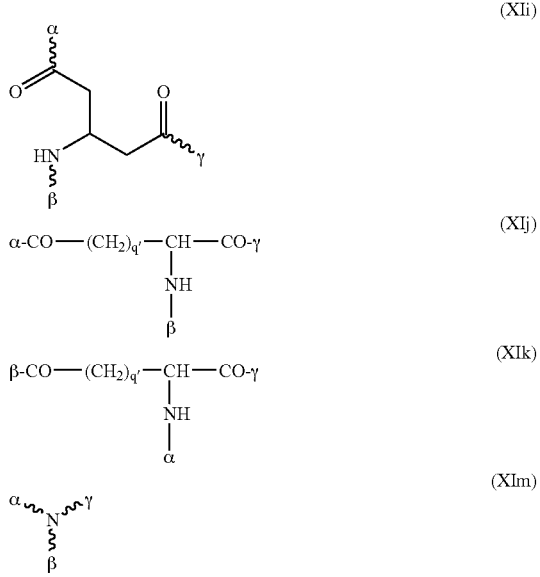

where
n' and m' independently of one another are an integer between 0 and 4, and m'+n' is $\geq 1$, and
$R^{11}$ and $R^{11'}$ are independently of one another either —H or —OH, where when m'+n'$\geq 1$ each group —$(CR^{11}R^{11'})$— can be identical or different, and
W is either a direct bond, —O— or a phenylene group, which can optionally be substituted by 1 to 4 hydroxyl groups, and
q' is either 1, 2, 3 or 4,
where α is the binding site of backbone to the chelate K, β is the binding site of backbone to the polar group and γ is the binding site of backbone to the radical linker.

Preferred metal chelates are those having backbone (XIb), (XIc), (XIe) and (XIm).

Preferred Embodiments for the Polar Group of Metal Chelates According to the Invention (According to Formula I) and Intermediates (According to Formula Ia):

In another preferred embodiment of the invention, the polar group is a monosaccharide radical having 5 or 6 C atoms or an oligosaccharide radical, preferably glucose, mannose, galactose, ribose, arabinose or xylose or their deoxysugars such as, for example, 6-deoxygalactose (fucose) or 6-deoxy-mannose (rhamnose) or their peralkylated derivatives. Glucose, mannose and galactose, in particular mannose, are particularly preferred where the mono- or oligosaccharide radical is bonded to the backbone via a group Q where Q has the meaning of a group selected from:

δ-CO—$(CH_2)_{n''}$-ε,

δ-NH—$(CH_2)_{n''}$-ε, or

δ-$(CH_2)_{m''}$-ε where
n" is an integer from 1 and 5, and
m" is an integer from 1 and 6, and
δ indicates the binding site to the backbone, and
ε is the binding site to the mono- or oligosaccharide radical.

In another preferred embodiment, the polar group is a radical selected from the chelate radicals of the general formulae II to IX, where R$^1$ here is a hydrogen atom or a metal ion equivalent of atomic number 20-29, 31-33, 37-39, 42-44, 49 or 57-83, and R$^2$, R$^3$, R$^4$, R$^5$, R$^6$, R$^7$, R$^8$, R$^9$, R$^{10}$, R$^{12}$, R$^{13}$, K', A', U, U', U$^2$, U$^1$ and p' have the meaning indicated above, or a carbon chain having 1-30 C atoms bonded to the backbone via —CO—, —NR$^{14}$— or a direct bond, which can be linear or branched, saturated or unsaturated, and which is optionally interrupted by 1-10 oxygen atoms, 1-5 —NHCO— groups, 1-5 —CONH— groups, 1-2 sulphur atoms, 1-5 —NH— groups or 1-2 phenylene groups, which can optionally be substituted by 1-2 OH groups, 1-2 NH$_2$ groups, 1-2 —COOH groups, or 1-2 —SO$_3$H groups, and which is optionally substituted by 1-10 OH groups, 1-5 —COOH groups, 1-2 SO$_3$H groups, 1-5 NH$_2$ groups, 1-5 C$_1$-C$_4$-alkoxy groups R$^{14}$ is hydrogen or C$_1$-C$_4$ alkyl.

In a particularly preferred embodiment of the present invention, the polar group is selected from one of the following radicals:

—C(O)CH$_2$O[(CH$_2$)$_2$O]$_p$R'

—C(O)CH$_2$OCH[CH$_2$OCH(CH$_2$OR')$_2$]$_2$

—C(O)CH$_2$OCH$_2$CH[CH$_2$OCH(CH$_2$OR')$_2$]$_2$

—R"N[(CH$_2$)$_2$O]$_p$R'

—N{[(CH$_2$)$_2$O]$_p$R'}$_2$

—R"NCH$_2$CH(OH)CH$_2$OH

—N[CH$_2$CH(OH)CH$_2$OH]$_2$

—R"NCH(CH$_2$OH)CH(OH)CH$_2$OH

—N[CH(CH$_2$OH)CH(OH)CH$_2$OH]$_2$

—R"NCH[CH$_2$OCH(CH$_2$OR')$_2$]$_2$

—R"NCH$_2$CH[CH$_2$OCH(CH$_2$OR')$_2$]$_2$

—R"NCH$_2$CH$_2$OCH[CH$_2$OCH(CH$_2$OR')$_2$]$_2$

—R"NCH$_2$CH$_2$OCH$_2$CH[CH$_2$OCH(CH$_2$OR')$_2$]$_2$

—N{CH[CH$_2$OCH(CH$_2$OR')$_2$]$_2$}$_2$

—N{CH$_2$CH[CH$_2$OCH(CH$_2$OR')$_2$]$_2$}$_2$

—R"NCH$_2$CH(OH)CH(OH)CH(OH)CH(OH)CH$_2$OH

—N[CH$_2$CH(OH)CH(OH)CH(OH)CH(OH)CH$_2$OH]$_2$ or a complex of the formula (IVa),
where
R$^1$, R$^2$, R$^3$ and U are as defined above for formula (IVa),
p is either 1, 2, 3, 4, 5, 6, 7, 8 or 9, and
R' is either —H or —CH$_3$, and
R" is either H or a C$_1$ to C$_4$-alkyl radical.
Preferably, p is 1, 2, 3, or 4.
The polar radicals cited here are commercial products or are prepared according to methods described in the literature: Cassel et al., *Eur. J. Org. Chem.*, 2001, 5, 875-896; Whitessides et al., *JACS*, 1994, 5057-5062; Voegtle et al., *Liebigs Ann. Chem.*, 1980, 858-862; Liu et al., *Chem. Commun.*, 2002, 594; Mitchell et al., *Heterocyclic Chem.*, 1984, 697-699; Bartsch et al., *J. Org. Chem.*, 1984, 4076-4078; Keana et al., *J. Org. Chem.*, 1983, 2647-2654.

In a very particularly preferred embodiment, the polar group is a radical bonded to the backbone, of the formula:

—C(O)CH$_2$O[(CH$_2$)$_2$O]$_p$R' in which
p and R' have the meaning indicated above, where especially preferably R' is the group —CH$_3$.

Preferred Embodiments for Metal Ions of Metal Chelates According to the Invention:

If the compound according to the invention is intended for use in NMR diagnosis, the metal ion of the signal-emitting group must be paramagnetic. These are in particular the di- and trivalent ions of the elements of atomic number 21-29, 42, 44 and 58-70. Suitable ions are, for example, the chromium(III), iron(II), cobalt(II), nickel (II), copper(II), praseodymium(III), neodymium(III), samarium(III) and ytterbium(III) ion. Because of their strong magnetic moment, gadolinium(III), terbium(III), dysprosium(III), holmium(III), erbium(III), iron(III) and manganese(II) ions are particularly preferred.

For use of the compounds according to the invention in nuclear medicine (radio-diagnostics and radiotherapy), the metal ion must be radioactive. Suitable radio-isotopes are, for example, those of the elements of atomic number 27, 29, 31-33, 37-39, 43, 49, 62, 64, 70, 75 and 77. Technetium, gallium, indium, rhenium and yttrium are preferred.

If the compound according to the invention is intended for use in X-ray diagnosis, the metal ion is preferably derived from an element of relatively high atomic number in order to achieve adequate absorption of the X-rays. It has been found that diagnostic agents which contain a physiologically tolerable complex salt with metal ions of elements of atomic number 25, 26 and 39 and 57-83 are suitable for this purpose.

Manganese(II), iron(II), iron(III), praseodymium(III), neodymium(III), samarium(III), gadolinium(III), ytterbium(III) or bismuth(III) ions, in particular dysprosium (III) ions and yttrium(III) ions, are preferred.

Acidic hydrogen atoms optionally present in R$^1$, that is those which have not been substituted by the central ion, can optionally be replaced completely or partially by cations of inorganic and/or organic bases or amino acids or amino acid amides.

Suitable inorganic cations are, for example, the lithium ion, the potassium ion, the calcium ion and in particular the sodium ion. Suitable cations of organic bases are, inter alia, those of primary, secondary or tertiary amines, such as, for example, ethanolamine, diethanolamine, morpholine, glucamine, N,N-dimethyl-glucamine and in particular N-methylglucamine. Suitable cations of amino acids are, for example, those of lysine, of arginine and of ornithine and the amides of otherwise acidic or neutral amino acids.

The compounds according to the invention are particularly suitable for use in NMR and X-ray diagnosis, radiodiagnosis and radiotherapy, and in MRT lymphography. The metal chelates having a perfluorinated PEG radical are in particular suitable for use in magnetic resonance tomography (MRT) for the demonstration of various physiological and pathophysiological structures and thus for the improvement of the diagnostic information, for example the location and the degree of illness, for the selection and outcome assessment of a targeted therapy and for the prophylaxis of diseases and disorders.

Suitable diseases and disorders comprise oncoses, in particular detection and characterization of primary tumors, remote metastases, lymph node metastases and necroses, cardiovascular diseases, in particular changes in the vessel diameter such as stenoses and aneurysms, atherosclerosis by detection of atherosclerotic plaques, thromboembolic diseases, infarcts, necroses, inflammation, in particular arthritis, osteomyelitis, ulcerative colitis, and nerve damage.

In a particularly preferred embodiment, the substances according to the invention are employed for MRT lymphography.

In a further particularly preferred embodiment, the substances according to the invention are employed for blood pool imaging.

In a particularly preferred embodiment, the substances according to the invention are employed for necrosis or tumour imaging.

The invention also relates to pharmaceutical compositions which contain at least one physiologically tolerable compound according to the invention, optionally with the additives customary in galenics.

The compounds of the present invention are distinguished by outstanding tolerability and at the same time outstanding imaging properties. They are thus particularly highly suitable for systemic use in MRT, in particular in MRT lymphography and in tumour imaging. The compounds are by outstanding systemic tolerability.

The preparation of the pharmaceutical compositions according to the invention is carried out in a manner known per se by suspending or dissolving the complex compounds according to the invention—optionally with addition of the additives customary in galenics—in aqueous medium and subsequently optionally sterilizing the suspension or solution. Suitable additives are, for example, physiologically acceptable buffers (such as, for example, tromethamine), additives of complexing agents or weak complexes (such as, for example, diethylenetriaminepentaacetic acid or the Ca complexes corresponding to the metal complexes according to the invention) or—if necessary—electrolytes such as, for example, sodium chloride or—if necessary—antioxidants such as, for example, ascorbic acid.

If suspensions or solutions of the compositions according to the invention in water or physiological saline solution are desired for enteral or parenteral administration or other purposes, they are mixed with one or more of the excipient(s) customary in galenics [for example methylcellulose, lactose, mannitol] and/or surfactant(s) [for example lecithins, TWEEN®, MYRJ®] and/or flavouring(s) for taste correction [for example ethereal oils].

In principle, it is also possible to prepare the pharmaceutical compositions according to the invention without isolation of the complexes. In each case, particular care must be used to perform the chelate formation in such a way that the complexes according to the invention are virtually free of non-complexed metal ions having a toxic action.

This can be guaranteed, for example, by control titrations during the preparation process with the aid of colour indicators such as Xylenol Orange. The invention therefore also relates to processes for the preparation of the complex compounds and their salts. As the last assurance, purification of the isolated complex remains.

In the case of the in-vivo administration of the compositions according to the invention, these can be administered together with a suitable vehicle such as, for example, serum or physiological saline solution and together with another protein such as, for example, human serum albumin (HSA).

The compositions according to the invention are customarily administered parenterally, preferably i.v. They can also be administered intravasally or interstitially/intra-cutaneously, depending on whether body vessels or tissue are to be investigated.

The pharmaceutical compositions according to the invention preferably contain 0.1 µmol-2 mol/l of the complex and are dosed as a rule in amounts of 0.0001-5 mmol/kg.

The compositions according to the invention fulfil the various requirements for suitability as contrast agents for magnetic resonance tomography. After oral or parenteral administration, they are outstandingly suitable for improving the image obtained with the aid of magnetic resonance tomographs in its meaningfulness by increasing the signal intensity. Furthermore, they exhibit the high efficacy which is necessary in order to burden the body with amounts of foreign substances which are as small as possible, and the outstanding tolerability which is necessary in order to maintain the non-invasive character of the investigations.

The good water solubility and low osmolality of the compositions according to the invention allows highly concentrated solutions to be prepared, thereby keeping the volume burden of the circulation within justifiable limits and compensating the dilution by the body fluid. Furthermore the compositions according to the invention not only have a high stability in vitro, but also a surprisingly high stability in vivo, such that release or exchange of the ions—which are toxic per se—bound in the complexes within the time in which the novel contrast agents are excreted completely again only takes place extremely slowly.

In general, the compositions according to the invention are dosed as NMR diagnostics in amounts of 0.0001-5 mmol/kg, preferably 0.005-0.5 mmol/kg.

Furthermore, the complex compounds according to the invention can advantageously be used as susceptibility reagents and shift reagents for in-vivo NMR spectroscopy.

On account of their favourable radioactive properties and the good stability of the complex compounds contained in them, the compositions according to the invention are also suitable as radiodiagnostics. Details of such a use and dosage are described, for example, in "Radiotracers for Medical Applications", CRC Press, Boca Raton, Fla.

The compounds and compositions according to the invention can also be used in positron emission tomography, which uses positron-emitting isotopes such as, for example, $^{43}$Sc, $^{44}$Sc, $^{52}$Fe, $^{55}$Co, $^{68}$Ga and $^{86}$Y (Heiss, W. D.; Phelps, M. E.; Positron Emission Tomography of Brain, Springer Verlag Berlin, Heidelberg, N.Y. 1983).

The compounds according to the invention are distinguished especially in that they are completely eliminated from the body and are thus outstandingly tolerable. The outstanding imaging properties can thus be utilized and the non-invasive character of the diagnosis can be retained.

Since the substances according to the invention concentrate in malignant tumors (no diffusion into healthy tissue, but high permeability of tumour vessels), they can also assist the radiation therapy of malignant tumors. This differs from the corresponding diagnosis only by the amount and nature of the isotopes used. The aim here is the destruction of tumour cells by energy-rich short-wave radiation having a range which is as low as possible. For this, interactions of the metals (such as, for example, iron or gadolinium) contained in the complexes with ionizing radiation (e.g. X-rays) or with neutron beams are utilized. By means of this effect, the local radiation dose is significantly increased at the site where the metal complex is situated (e.g. in tumors). In order to produce the same radiation dose in malignant tissue, when using such metal complexes the radiation burden for healthy tissue can be reduced considerably and thus burdening side effects for the patients can be avoided. The metal complex conjugates according to the invention are therefore also suitable as a radiosensitizing substance in radiation therapy of malignant tumors (e.g. utilization of Mössbauer effects or in neutron capture therapy). Suitable β-emitting ions are, for example, $^{46}$Sc, $^{47}$Sc, $^{48}$Sc, $^{72}$Ga, $^{73}$Ga and $^{90}$Y. Suitable α-emitting ions having low half-lives are, for example, $^{211}$Bi, $^{212}$Bi, $^{213}$Bi and $^{214}$Bi, where $^{212}$Bi is preferred. A suitable photon- and electron-emitting ion is $^{158}$Gd, which can be obtained from $^{157}$Gd by neutron capture.

If the composition according to the invention is intended for use in the variant of radiation therapy proposed by R. L. Mills et al. (Nature Vol. 336, (1988), p. 787], the central ion must be derived from a Mössbauer isotope such as, for example, $^{57}$Fe or $^{151}$Eu.

In the case of the in-vivo administration of the compositions according to the invention, these can be administered together with a suitable vehicle such as, for example, serum or physiological saline solution and together with another protein such as, for example, human serum albumin. The dosage here is dependent on the nature of the cellular disorder, the metal ion used and the nature of the imaging method.

The compositions according to the invention are customarily administered parenterally, preferably i.v. They can also be administered—as already discussed—intravasally or interstitially/intracutaneously, depending on whether body vessels or tissue are to be investigated.

The compositions according to the invention are outstandingly suitable as X-ray contrast agents, where it is particularly to be emphasized that no signs of the anaphylaxis-like reactions known from the iodine-containing contrast agents can be detected with them in biochemical/pharmacological investigations. Because of the favourable absorption properties, they are particularly useful in regions of higher tube voltages for digital subtraction techniques.

In general, the compositions according to the invention are dosed in amounts of 0.1-5 mmol/kg, preferably 0.25-1 mmol/kg, for use as X-ray contrast agents in analogy to the example of meglumine diatrizoate.

The expression "metal ion equivalent" as used in the present application is a term which is customary and known to the person skilled in the art in the field of complex chemistry. A metal ion equivalent is an equivalent of metal ions which can bind to, for example, a carboxylate group instead of hydrogen. For example, a $Gd^{3+}$ can bind to 3 carboxylate groups, i.e. ⅓$Gd^{3+}$ corresponds to the metal ion equivalent $R^1$, for example, in formula (II), (III), (IV), (IVa), (IVb), (Va), (Vb), (VI) or (VII) if the metal is gadolinium.

A "PEG radical" within the meaning of the present invention is a monovalent linear or branched alkyl radical having up to 30 C atoms comprising at least one ethylene oxide radical. Preferably, the radical is linear. Preferably, the radical contains 1-14 ethylene oxide radicals. PEG radicals are particularly preferred in which all ethylene oxide radicals according to the following formula are present in the radical:

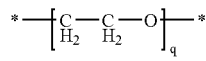

where q is the number of ethylene oxide radicals.

A "perfluorinated PEG radical" within the meaning of the present invention is a monovalent radical derived from a PEG radical where the radical is perfluorinated.

A "polar group" within the meaning of the present invention is a radical comprising functional groups, whose characteristic electron distributions of the substance according to the invention give a considerable electrical dipole moment. Such groups cause the affinity to other polar chemical compounds (see also intermolecular forces) and they are therefore also responsible for the hydrophilic character of the substances according to the invention. Polar radicals are those having an electrical dipole moment and polarized covalent bond.

"TREN" within the meaning of the present invention is the abbreviation for tris(aminoethyl)amine.

"HOPO" within the meaning of the present invention is the abbreviation for hydroxypyridinone "HOPY" within the meaning of the present invention is the abbreviation for hydroxypyrimidinone "TAM" within the meaning of the present invention is the abbreviation for terephthalamide "Chelator" within the meaning of the present invention is a complex-forming substance, which with at least one metal ion of atomic number 21-29, 31-33, 37-39, 42-44, 49 or 57-83 a complex having a stability constant of at least $10^{15}$, preferably at least $10^{18}$. The stability constant is determined as described in (Martell, A. E.; Motekaitis, R. J. *The Determination and Use of Stability Constants*, 2nd ed.; VCH: New York, 1992).

Exemplary Description of Synthesis Routes:

The invention furthermore relates to a process for the preparation of perfluoro-PEG-containing metal complexes of the general formula I

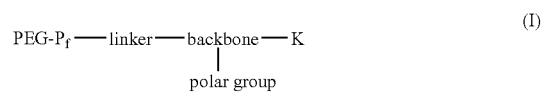

with K in the sense of a metal complex of one of the general formulae II, III, IVa, IVb, Va, Vb, VI to VIII, and linker, backbone, polar group and PEG-$P_f$, in the sense indicated above, characterized in that, in a manner known per se, a carboxylic acid of the general formula II

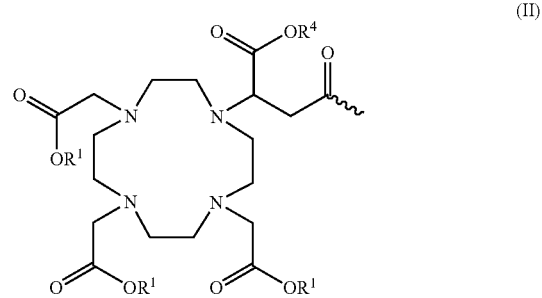

in which $R^1$ is a metal ion equivalent of atomic number 21-29, 31-33, 37-39, 42-44, 49 or 57-83 or a carboxyl protective group, and $R^4$ and $U^1$ have the meaning mentioned above
or a carboxylic acid of the general formula III

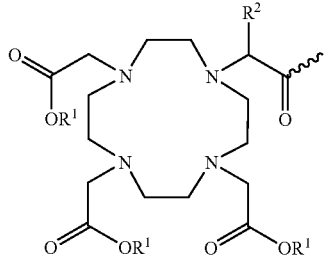
(III)

in which $R^1$ and $R^2$ have the meaning mentioned
or a carboxylic acid of the general formula IVa or IVb

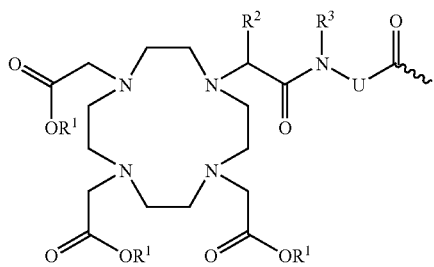
(IVa)

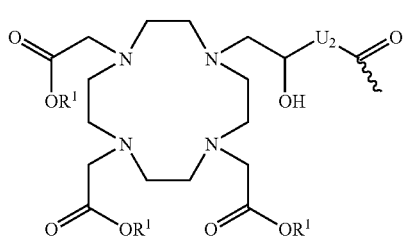
(IVb)

in which $R^1$, $R^2$, $R^3$ and U, $U_2$ have the meaning mentioned
or a carboxylic acid of the general formula Va or Vb

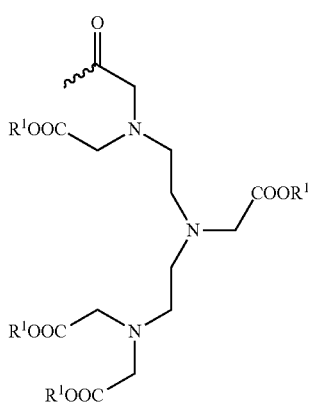
(Va)

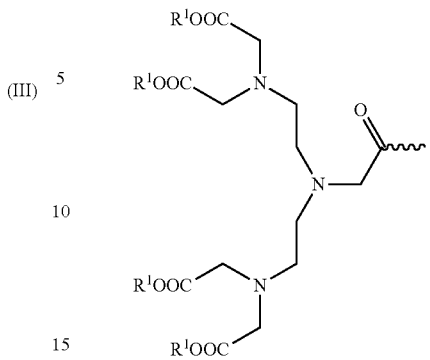
(Vb)

in which $R^1$ has the abovementioned meaning,
or a carboxylic acid of the general formula VI

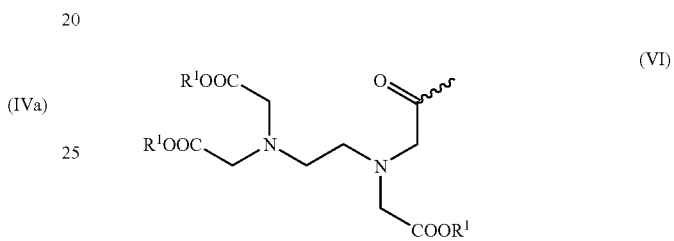
(VI)

in which $R^1$ has the meaning mentioned
or a carboxylic acid of the general formula VII

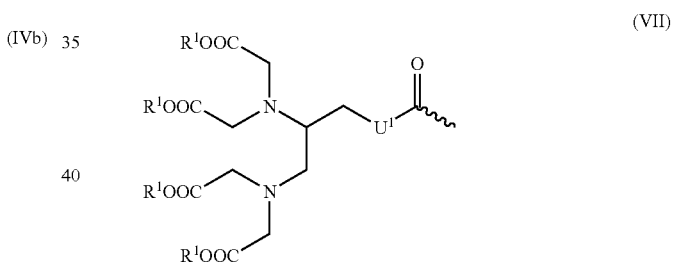
(VII)

in which $R^1$ and $U^1$ have the meanings mentioned,
or a carboxylic acid of the general formula VIII

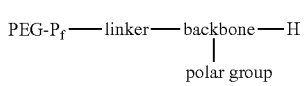
(VIII)

in which $K^1$ and A' have the meanings mentioned,
and U' contains a carboxylic acid radical terminally,
in optionally activated form with an amine of the general formula XIIa $$\text{PEG-P}_f\text{—linker—backbone—H} \atop | \atop \text{polar group} \quad \text{(XIIa)}$$

in which linker, backbone, polar group and PEG-$P_f$, which have the meaning indicated above, are reacted in a coupling reaction and optionally subsequent removal of optionally present protective groups to give a metal complex of the general formula I
or
if $R^1$ has the meaning of a protective group, after removal of these protective groups in a subsequent step, are reacted in a manner known per se with at least one metal oxide or metal salt of an element of atomic number 21-29, 31-33, 37-39, 42-44, 49 or 57-83, and subsequently, if desired, optionally present acidic hydrogen atoms are substituted by cations of inorganic and/or organic bases, amino acids or amino acid amides.

This process for the preparation of metal complex carboxylic acid amides is known from DE 196 52 386.

The mixture of metal complex carboxylic acid employed in the coupling reaction, which contains optionally present carboxyl and/or hydroxyl groups in protected form, and at least one solubilizing substance in an amount of up to 5, preferably 0.5-2 mol, equivalents based on the metal complex carboxylic acid can be prepared both in an added reaction step and isolated (e.g. by evaporation, freeze drying or spray drying of an aqueous or water-miscible solution of the constituents or by precipitation with an organic solvent from a solution of this type) and subsequently reacted in DMSO with a dehydrating reagent and optionally a coupling aid and formed in situ optionally by addition of solubilizing substance(s) to the DMSO suspension of metal complex carboxylic acid, dehydrating reagent and optionally a coupling aid.

For pretreatment (acid activation), the reaction solution prepared by one of these processes is kept for 1 to 24, preferably 3 to 12, hours at temperatures of 0 to 50° C., preferably at room temperature.

Subsequently, an amine of the general formula XIIa is added

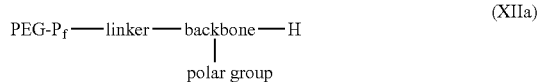

(XIIa)

in which linker, backbone, polar group and PEG-P$_f$ have the meanings indicated above, without solvent or dissolved, for example, in dimethyl sulphoxide, alcohols such as, for example, methanol, ethanol, isopropanol or their mixtures, formamide, dimethylformamide, water or mixtures of the solvent mentioned, preferably in dimethyl sulphoxide, in water or in solvents mixed with water. For the amide coupling, the reaction mixture thus obtained is kept at temperatures of 0 to 70° C., preferably 30 to 60° C., for 1 to 48, preferably 8 to 24, hours.

In some cases it has proved advantageous to employ the amine in the reaction in the form of its salts, e.g. as the hydrobromide or hydrochloride. For the liberation of the amine, a base such as, for example, triethylamine, diisopropylethylamine, N-methyl-morpholine, pyridine, tripropylamine, tributylamine, lithium hydroxide, lithium carbonate, sodium hydroxide or sodium carbonate is added.

The protective groups optionally still present are subsequently removed.

The isolation of the reaction product is carried out according to the methods known to the person skilled in the art, preferably by precipitation with organic solvents, preferably acetone, 2-butanone, diethyl ether, ethyl acetate, methyl t-butyl ether, isopropanol or their mixtures. Further purification can be carried out, for example, by chromatography, crystallization or ultrafiltration.

Suitable solubilizing substances are alkali metal, alkaline earth metal, trialkylammonium salts, tetraalkylammonium salts, ureas, N-hydroxyimides, hydroxyaryltriazoles, substituted phenols and salts of heterocyclic amines. The following may be mentioned by way of example: lithium chloride, lithium bromide, lithium iodide, sodium bromide, sodium iodide, lithium methanesulphonate, sodium methanesulphonate, lithium p-toluenesulphonate, sodium p-toluenesulphonate, potassium bromide, potassium iodide, sodium chloride, magnesium bromide, magnesium chloride, magnesium iodide, tetraethylammonium p-toluenesulphonate, tetramethylammonium p-toluenesulphonate, pyridinium p-toluenesulphonate, triethylammonium p-toluenesulphonate, 2-morpholino-ethylsulphonic acid, 4-nitrophenol, 3,5-dinitrophenol, 2,4-dichlorophenol, N-hydroxysuccinimide, N-hydroxyphthalimide, urea, tetramethylurea, N-methylpyrrolidone, formamide and cyclic ureas, where the five first-mentioned compounds are preferred. Dehydrating reagents used are all agents known to the person skilled in the art. Mention may be made by way of example of carbodiimides and onium reagents such as, for example, dicyclohexylcarbodiimide (DCCI), 1-ethyl-3-(3-dimethylaminopropyl)-carbodiimide hydroxychloride (EDC), benzotriazol-1-yloxytris(dimethylamino)-phosphonium hexafluorophosphate (BOP) and O-(benzotriazol-1-yl)-1,1,3,3-tetramethyluronium hexafluorophosphate (HBTU), preferably DCCI.

In the literature, for example, the following suitable processes are described:

Activation of carboxylic acids. Survey in Houben-Weyl, Methoden der Organischen Chemie [Methods of Organic Chemistry], Volume XV/2, Georg Thieme Verlag Stuttgart, 1974 (and J. Chem. Research (S) 1996, 302).

Activation with carbodiimides. R. Schwyzer and H. Kappeler, Helv. 46: 1550 (1963).

E. Wünsch et al., B. 100: 173 (1967).

Activation with carbodiimides/hydroxysuccinimide: J. Am. Chem. Soc. 86: 1839 (1964) and J. Org. Chem. 53: 3583 (1988). Synthesis 453 (1972).

Anhydride method, 2-ethoxy-1-ethoxycarbonyl-1,2-dihydroquinoline: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

Imidazolide method: B. F. Gisin, R. B. Menifield, D. C. Tosteon, Am. Soc. 91: 2691 (1969).

Acid chloride methods, thionyl chloride: Helv., 42: 1653 (1959).

Oxalyl chloride: J. Org. Chem., 29: 843 (1964).

Coupling aids optionally to be used are all suitable coupling aids known to the person skilled in the art (Houben-Weyl, Methoden der organischen Chemie, Vol. XV/2, Georg Thieme-Verlag, Stuttgart, 1974). Mention may be made by way of example of 4-nitro-phenol, N-hydroxysuccinimide, 1-hydroxybenzotriazole, 1-hydroxy-7-azabenzotriazole, 3,5-dinitrophenol and pentafluorophenol. 4-Nitrophenol and N-hydroxysuccinimide are preferred; the first-mentioned reagent here is particularly preferred.

The removal of the protective groups is carried out by processes known to the person skilled in the art, for example by hydrolysis, hydrogenolysis, alkaline hydrolysis of the esters with alkali in aqueous-alcoholic solution at temperatures of 0° to 50° C., acidic hydrolysis with mineral acids or in the case of, for example, tert-butyl esters, with the aid of trifluoroacetic acid. [Protective Groups in Organic Synthesis, 2nd Edition, T. W. Greene and P. G. M. Wuts, John Wiley and Sons, Inc. New York, 1991], in the case of benzyl ethers with hydrogen/palladium/carbon.

The compounds according to the invention of the general formula I $$\text{PEG-P}_f\text{—linker—backbone—K} \atop | \atop \text{polar group} \quad (I)$$

with K in the sense of a metal complex of the general formula (IV), and linker, backbone, polar group and PEG-P$_f$ in the sense indicated above are prepared by reacting an amine of the general formula IV (IV) [structure: DO3A-type macrocycle with OR$^1$ groups and CH(OH)—U$^2$—NR$^{14}$ side chain]

in which R$^1$ is a metal ion equivalent of atomic number 21-29, 31-33, 37-39, 42-44, 49 or 57-83 or a carboxyl protective group, and U$^2$ and R$^{14}$ in the sense indicated above, with an optionally activated carboxylic acid of the general formula XIIIb $$\text{PEG-P}_f{'}\text{—linker—backbone—OH} \atop | \atop \text{polar group} \quad (XIIb)$$

where linker, backbone, polar group and PEG-P$_f$ have the meanings indicated above, in a coupling reaction and optionally subsequent removal of protective groups optionally present to give a metal complex of the general formula I or if R$^1$ has the meaning of a protective group, after removal of these protective groups, reacting in a subsequent step in a manner known per se with at least one metal oxide or metal salt of an element of atomic number 21-29, 31-33, 37-39, 42-44, 49 or 57-83, and subsequently, if desired, optionally substituting acidic hydrogen atoms present by cations of inorganic and/or organic bases, amino acids or amino acid amides.

The carboxylic acids employed of the general formulae IIa to VIIa are either known compounds or are prepared according to the processes described in the examples, see DE 10040381 and DE 10040858. Thus, the preparation of the carboxylic acids of the general formula IIa is known from DE 196 52 386. Amines of the general formula IV can be prepared as described in WO 95/17451.

Compounds of the general formula XIIa+b $$\text{PEG-P}_f{'}\text{—linker—backbone—H} \atop | \atop \text{polar group} \quad (XIIa)$$

$$\text{PEG-P}_f{'}\text{—linker—backbone—OH} \atop | \atop \text{polar group} \quad (XIIb)$$

with backbone in the sense of $$\beta\diagdown\!\!\!\!_{\gamma}\!\!N\text{—}(CR^{11}R^{11'})_{n'}\text{—}W\text{—}(CR^{11}R^{11'})_{m'}\text{—}\underset{H}{N}\diagdown\!\!\!\!^{\alpha} \quad (XIa)$$

$$\alpha\diagdown\!\!\!\!_{\gamma}\!\!N\text{—}(CR^{11}R^{11'})_{n'}\text{—}W\text{—}(CR^{11}R^{11'})_{m'}\text{—}\underset{H}{N}\diagdown\!\!\!\!^{\beta} \quad (XIb)$$

$$\alpha\text{-NH—}(CH_2)_{q'}\text{—}\underset{\underset{\gamma}{NH}}{CH}\text{—CO-}\beta \quad (XIc)$$

$$\alpha\text{-NH—}(CH_2)_{q'}\text{—}\underset{\underset{\beta}{NH}}{CH}\text{—CO-}\gamma \quad (XId)$$

$$\beta\text{-NH—}(CH_2)_{q'}\text{—}\underset{\underset{\alpha}{NH}}{CH}\text{—CO-}\gamma \quad (XIe)$$

$$\beta\text{-NH—}(CH_2)_{q'}\text{—}\underset{\underset{\gamma}{NH}}{CH}\text{—CO-}\alpha \quad (XIf)$$

(XIg) [3,5-diaminobenzoyl structure with α and β NH positions and γ carbonyl]

(XIh) [serine-type: α-NH—CH(CH$_2$—O-β)—C(=O)-γ]

(XIi) [glutamic acid-type structure with α, β, γ positions]

$$\alpha\text{-CO—}(CH_2)_{q'}\text{—}\underset{\underset{\beta}{NH}}{CH}\text{—CO-}\gamma \quad (XIj)$$

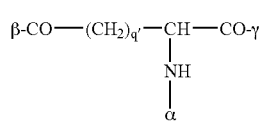 (XIk)

 (XIm)

where α is the binding site of backbone to the chelate K, β is the binding site of backbone to the polar group and γ is the binding site of backbone to the radical linker, are prepared by reacting the hydrophilic carboxylic acids R described above by methods of amide formation known to the person skilled in the art with amines of the general formula XIIIa

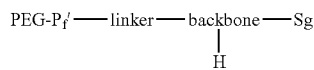 (XIIIa)

or in the case of the hydrophilic amines R described above, by methods of amide formation known to the person skilled in the art with carboxylic acids of the general formula XIIIb

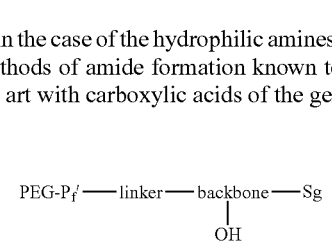 (XIIIb)

with Sg in the sense of a protective group and linker, backbone and PEG-P$_f$ in the sense indicated above.

The removal of the protective groups is carried out by processes known to the person skilled in the art, for example by hydrolysis, hydrogenolysis, alkaline hydrolysis of the esters with alkali in aqueous-alcoholic solution at temperatures of 0° to 50° C., acidic hydrolysis with mineral acids or in the case of, for example, tert-butyl esters with the aid of trifluoroacetic acid. [Protective Groups in Organic Synthesis, 2nd Edition, T. W. Greene and P. G. M. Wuts, John Wiley and Sons, Inc. New York, 1991], in the case of benzyl ethers with hydrogen/palladium/carbon.

Compounds of the general formula XIIIa+b,

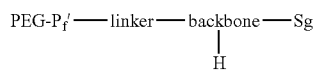 (XIIIa)

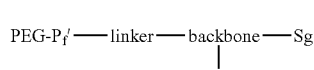 (XIIIb)

which are derived from the compounds of the general formula XIIa+b,

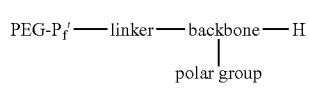 (XIIa)

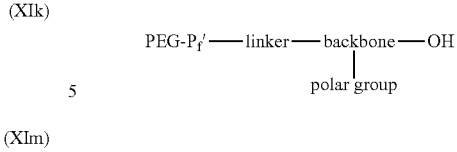 (XIIb)

with backbone in the sense of

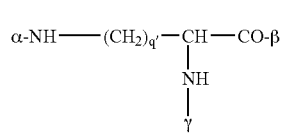 (XIc)

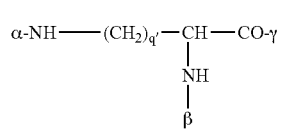 (XId)

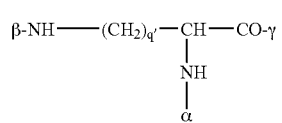 (XIe)

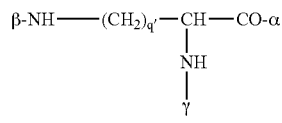 (XIf)

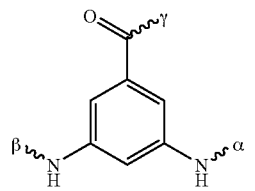 (XIg)

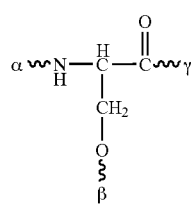 (XIh)

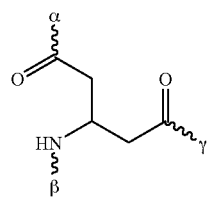 (XIi)

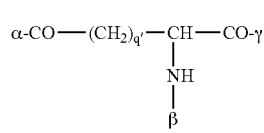 (XIj)

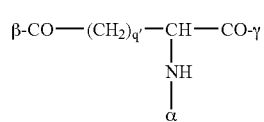 (XIk)

are prepared by reacting doubly protected amino acids of the general formula XIV

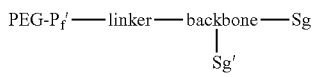 (XIV)

Sg and Sg' in the sense of a protective group, where Sg and Sg' can be cleaved differently, and reacting linker, backbone and PEG-P$_f$ in the sense indicated above, The removal of the protective groups takes place according to the processes known to the person skilled in the art described above.

Compounds of the general formula (XIV) are prepared by reacting doubly protected amino acids of the general formula XVa+b

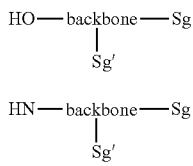

(XVa)

(XVb)

according to methods of amide formation known to the person skilled in the art, in the case of (XVa) with amines of the general formula XVIa, PEG-P$_f'$-linker-NH (XVIa)

or, in the case of (XVb) with acids of the general formula XVIb,

PEG-P$_f'$-linker-OH (XVIb)

Such doubly protected amino acids of the general formula (XVa+b) are commercial products (Bachem).

Compounds of the general formula XIIa,

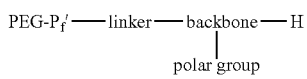 (XIIa)

with backbone in the sense of

 (XIm)

are prepared by reacting acids of the general formula XVIb

PEG-P$_f'$-linker-OH (XVIb)

with the hydrophilic primary amines R described above according to methods of amide formation known to the person skilled in the art.

Compounds of the general formula XIIIa,

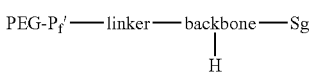 (XIIIa)

which are derived from the compounds of the general formula XIIa,

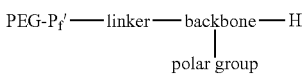 (XIIa)

with backbone in the sense of

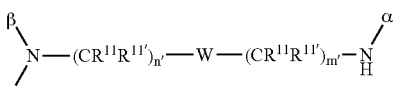 (XIa)

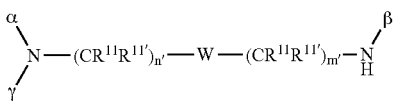 (XIb)

are prepared by reacting monoprotected diamines of the general formula XVII

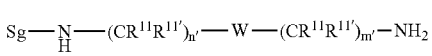 (XVII)

with $R^{11}$, $R^{11'}$, n', W and m' in the sense indicated above and with Sg in the sense of a protective group, with nucleophiles of the general formula XVIc, PEG-P$_f'$-linker-Nu (XVIc)

in which Nu is a nucleofuge, in the presence of a base and optionally of a phase-transfer catalyst. As a nucleofuge, the radicals —Cl, —Br, —I, —OTs, —OMs, —OSO$_2$CF$_3$, —OSO$_2$C$_4$F$_9$ or —OSO$_2$C$_8$F$_{17}$, for example, can be present in the alkylation reagent of the general formula XVIc.

Monoprotected diamines of the general formula (XVII) are known from the literature and are described in the following publications Atwell et al., *Synthesis*, 1984, 1032-1033.
Koenig et al., *Eur. J. Org. Chem.*, 2002, 3004-3014.
Boeijen et al., *J. Org. Chem.*, 2001, 8454-8462.
Spivak et al., *J. Org. Chem.*, 1999, 4627-4634.
Pittelkov et al., *Synthesis*, 2002, 2195-2202.
Katchalski et al., *J. Am. Chem. Soc.*, 1951, 1829.
BASF AG patent, DE 1130803

Acids of the general formula (XVIb) can be prepared by dissolving alcohols of the general formula XIX PEG-P$_f$—OCF$_2$CH$_2$OH (XIX)

in a non-water-miscible organic solvent and reacting with an alkylating reagent of the general formula (XX)

Nu-L-COO—Sg (XX), in which Nu is a nucleofuge, L is —(CH$_2$)—$_z$, (where z=1-5), —CH$_2$—CHOH—, or —CH(CHOH—CH$_2$OH)—CHOH—CHOH—, and Sg is a protective group,
in the presence of a base and optionally of a phase transfer catalyst. As a nucleofuge, the radicals —Cl, —Br, —I, —OTs, —OMs, —OSO$_2$CF$_3$, —OSO$_2$C$_4$F$_9$ or —OSO$_2$C$_8$F$_{17}$, for example, can be present in the alkylating reagent of the general formula XVIII.

The protective group is a customary acid protective group. These protective groups are highly familiar to the person skilled in the art (Protective Groups in Organic Syntheses, second Edition, T. W. Greene and P. G. M. Wuts, John Wiley & Sons Inc., New York 1991).

The reaction according to the invention can be carried out at temperatures of 0-50° C., preferably of 0° C. to room temperature. The reaction times are from 10 minutes to 24 hours, preferably from 20 minutes to 12 hours.

The base is either added in solid form, preferably finely powdered, or as a 10-70% strength, preferably 30-50% strength, aqueous solution. Preferred bases used are NaOH and KOH.

Organic, non-water-miscible solvents which can be employed in the alkylation process according to the invention are, for example, toluene, benzene, CF$_3$-benzene, hexane, cyclohexane, diethyl ether, tetrahydrofuran, dichloromethane, MTB or their mixtures.

Phase transfer catalysts used in the process according to the invention are the quaternary ammonium or phosphonium salts known for this purpose or alternatively crown ethers such as, for example, [15]-crown-5 or [18]-crown-6. Preferably, quaternary ammonium salts having four identical or different hydrocarbon groups on the cation, selected from methyl, ethyl, propyl, isopropyl, butyl or isobutyl are suitable. The hydrocarbon groups on the cation must be large enough in order to guarantee a good solubility of the alkylating reagent in the organic solvent. According to the invention, N(butyl)$_4^+$-Cl$^-$, N(butyl)$_4^+$-HSO$_4^-$, but also N(methyl)$_4^+$-Cl$^-$ is particularly preferably employed.

Numerous examples of alcohols of the general formula (XIX) are described in U.S. Pat. No. 3,293,306.

Amines of the general formula (XVIa) can be obtained according to the following process: from the corresponding acids of the general formula (XVIb) by reaction with primary amines or ammonia according to methods of amide formation known to the person skilled in the art, and subsequent reduction, in a manner known per se, using diborane or lithium aluminium hydride.

Nucleophiles of the general formula (XVIc) can be obtained according to the following process: from the corresponding acids of the general formula (XVIb) by reduction, in a manner known per se, using DIBAL or lithium aluminium hydride to give the corresponding secondary alcohols. These can subsequently be converted to the corresponding nucleophiles by means of a Mitsunobu reaction [O. Mitsunobu, Synthesisis, 1981, 1-28].

On account of their outstanding tolerability and their pharmacokinetic properties, such as the very high contrast agent content at early points in time after administration and the rapid renal excretion, the compounds according to the invention are particularly suitable for the demonstration of the blood space, e.g. as a blood pool agent.

EXAMPLES

Example 1 a) 2H,2H,4H,4H,-3,6,9,12-Tetraoxaperfluorohexadecanoic acid 53.4 g (275 mmol) of tert-butyl bromoacetate are added at 0° C. to 100 g (182.45 mmol) of 1H,1H,-3,6,9-trioxaperfluoro-1-tridecanol (Apollo) and 20.5 g (365 mmol) of finely powdered potassium hydroxide and a catalytic amount (2 g) of tetra-n-butylammonium hydrogensulphate in 800 ml of toluene and the mixture is stirred at this temperature for 2 h and at room temperature for 12 h. The reaction solution is treated with 1500 ml of ethyl acetate and 800 ml of water. The organic phase is separated off and washed twice with 500 ml each of water, subsequently dried over magnesium sulphate and evaporated to dryness in vacuo. The residue is suspended in a mixture consisting of 1200 ml of methanol and 0.5 M sodium hydroxide solution in the ratio 2:1 and subsequently heated at 60° C. for 12 h. For work up, the reaction mixture is neutralized by treating with AMBERLITE® IR 120 ($^+$ form) cation exchange resin, filtered off from the exchanger, evaporated to dryness and chromatographed on silica gel (eluent: ethyl acetate/hexane 1:3).

Yield: 57.6 g (52% of theory) of a colourless wax
Elemental analysis:

| calc.: | C 23.78 | H 0.83 | F 59.55 |
| fnd.: | C 24.01 | H 0.87 | F 59.32 | b) (2H,2H,4H,4H,-3,6,9,12-Tetraoxaperfluorohexadecanoic acid)N-methylamide 15.3 g (120 mmol) of oxalyl chloride are added to 50 g (82.49 mmol) of the title compound from Example 1a in 500 ml of dichloromethane and the mixture is stirred at room temperature for 14 h. It is evaporated to dryness in vacuo, the residue is dissolved in 400 ml of dichloromethane, methylamine gas is passed into the solution at 0° C. for about 2 h and the mixture is subsequently stirred at room temperature for 4 h. The reaction solution is treated with 400 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 47.9 g (94% of theory) of a colourless wax
Elemental analysis:

| calc.: | C 25.22 | H 1.30 | N 2.26 | F 58.30 |
| fnd.: | C 25.36 | H 1.35 | N 2.22 | F 58.06 | c) N-Methyl-(1H,1H,2H,2H,4H,4H,-3,6,9,12-tetraoxaperfluorohexadecyl)amine 45 g (72.68 mmol) of the title compound from Example 1b in 150 ml of THF are treated with 50 ml of 10 M boranedimethyl sulphide (in THF) and heated under reflux for 5 h. The mixture is cooled to 0° C., 100 ml of methanol are added dropwise, and it is stirred at room temperature for 1 h and subsequently evaporated to dryness in vacuo. The residue is taken up in a mixture of 300 ml of ethanol/50 ml of 1 M hydrochloric acid and stirred at 40° C. for 14 h. It is evaporated to dryness in vacuo, the residue is taken up in 300 ml of 5% strength sodium hydroxide solution and extracted three times with 300 ml each of dichloromethane. The combined organic phases are dried over magnesium sulphate, evaporated to dryness in vacuo and the residue is chromatographed on silica gel (eluent: dichloromethane/methanol 10:1).

Yield: 33.9 g (77% of theory) of a colourless oil

Elemental analysis:

| calc.: | C 25.80 | H 1.67 | N 2.31 | F 59.64 |
|---|---|---|---|---|
| fnd.: | C 25.96 | H 1.69 | N 2.27 | F 59.36 | d) 6-N-Benzyloxycarbonyl-2-N-trifluoroacetyl-L-lysine[N-methyl-(1H,1H,2H,2H,4H,4H,-3,6,9,12-tetraoxaperfluorohexadecyl)]amide 24.7 g (100 mmol) of EEDQ (ethyl 2-ethoxy-1,2-dihydroquinoline-1-carboxylate) are added at 0° C. to 18.82 g (50 mmol) of 6-N-benzyloxycarbonyl-2-N-trifluoroacetyl-L-lysine (prepared according to EP 01/08498) and 30.31 g (50 mmol) of the title compound from Example 1c in 200 ml of THF and the mixture is stirred at room temperature for 16 h. It is evaporated to dryness in vacuo and the residue is chromatographed on silica gel (eluent: dichloromethane/methanol 20:1).
Yield: 38.6 g (80% of theory) of a colourless viscous oil.
Elemental analysis:

| calc.: | C 36.15 | H 2.82 | N 4.36 | F 43.38 |
|---|---|---|---|---|
| fnd.: | C 36.32 | H 2.85 | N 4.32 | F 43.11 | e) 6-N-Benzyloxycarbonyl-L-lysine[N-methyl-(1H,1H,2H,2H,4H,4H,-3,6,9,12-tetraoxaperfluorohexadecyl)]amide Ammonia gas is passed at 0° C. into a solution of 38 g (39.44 mmol) of the title compound from Example 1d in 250 ml of ethanol for 1 h, and the mixture is subsequently stirred at 0° C. for 4 h. It is evaporated to dryness in vacuo and the residue is precipitated from water with stirring. The solid is filtered off and dried in vacuo at 50° C.
Yield: 34.3 g (98% of theory) of an amorphous solid.
Elemental analysis:

| calc.: | C 37.38 | H 3.25 | N 4.84 | F 41.61 |
|---|---|---|---|---|
| fnd.: | C 37.54 | H 3.29 | N 4.79 | F 41.44 | f) 6-N-Benzyloxycarbonyl-2-N-[1-O-α-d-carbonylmethyl-(2,3,4,6-tetra-O-benzyl)-mannopyranose]-L-lysine[N-methyl-(1H,1H,2H,2H,4H,4H,-3,6,9,12-tetraoxaperfluorohexadecyl)]amide 9.51 g (46.11 mmol) of dicyclohexylcarbodiimide are added at 0° C. to a solution of 32.0 g (36.89 mmol) of the title compound from Example 1e and 22.09 g (36.89 mmol) of 1-O-α-d-carbonylmethyl-(2,3,4,6-tetra-O-benzyl)mannopyranose (prepared according to WO 99/01160 A1) and 4.25 g (36.89 mmol) N-hydroxysuccinimide in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).
Yield: 39.6 g (74% of theory) of a colourless viscous oil.

Elemental analysis:

| calc.: | C 52.25 | H 4.45 | N 2.90 | F 24.93 |
|---|---|---|---|---|
| fnd.: | C 52.43 | H 4.48 | N 2.87 | F 24.78 | g) 2-N-(1-O-α-d-Carbonylmethylmannopyranose)-L-lysine[N-methyl-(1H,1H,2H,2H,4H,4H,-3,6,9,12-tetraoxaperfluorohexadecyl)]amide 5.0 g of palladium catalyst (10% Pd/C) are added to a solution of 38.0 g (26.24 mmol) of the title compound from Example 1f in 600 ml of ethanol and the mixture is hydrogenated at room temperature for 24 h. It is filtered off from the catalyst and the filtrate is evaporated to dryness in vacuo.
Yield: 25.2 g (quantitative) of a colourless solid.
Elemental analysis:

| calc.: | C 34.01 | H 3.59 | N 4.41 | F 37.86 |
|---|---|---|---|---|
| fnd.: | C 34.48 | H 3.65 | N 4.36 | F 37.59 | h) 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine-[N-methyl-(1H,1H,2H,2H,4H,4H,-3,6,9,12-tetraoxaperfluorohexadecyl)]amide, Gd complex 20 g (20.76 mmol) of the title compound from Example 1g, 2.39 g (20.76 mmol) of N-hydroxysuccinimide, 1.76 g (41.52 mmol) of lithium chloride and 13.07 g (20.76 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved in 200 ml of dimethyl sulphoxide with gentle warming. 5.35 g (25.95 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).
Yield 21.5 g (62% of theory) of a colourless solid
Water content (Karl Fischer): 6.5%
Elemental analysis (based on the anhydrous substance):

| calc.: | C 35.30 | H 3.99 | N 7.16 | F 23.06 | Gd 10.05 |
|---|---|---|---|---|---|
| fnd.: | C 35.48 | H 4.03 | N 7.14 | F 22.98 | Gd 10.00 |

Example 2 a) (2H,2H,4H,4H,-3,6,9,12-Tetraoxaperfluorohexadecanoic acid)N-2-(methoxyethyl)-amide 2.55 g (20 mmol) of oxalyl chloride are added to 10 g (16.5 mmol) of the title compound from Example 1a in 100 ml of dichloromethane and the mixture is stirred at room temperature for 14 h. It is evaporated to dryness in vacuo, the residue is dissolved in 100 ml of dichloromethane, 2.48 g (33 mmol) of 2-methoxyethylamine (Aldrich) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 9.9 g (90% of theory) of a colourless wax
Elemental analysis:

| calc.: | C 27.16 | H 1.82 | N 2.11 | F 54.43 |
|---|---|---|---|---|
| fnd.: | C 27.36 | H 1.87 | N 2.08 | F 54.29 | b) N-2-Methoxyethyl-(1H,1H,2H,2H,4H,4H,-3,6,9,12-tetraoxaperfluorohexadecyl)-amine 9.5 g (14.32 mmol) of the title compound from Example 2a in 50 ml of THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. The mixture is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.5 g (91% of theory) of a colourless oil
Elemental analysis:

| calc.: | C 27.75 | H 2.17 | N 2.16 | F 55.60 |
|---|---|---|---|---|
| fnd.: | C 27.88 | H 2.20 | N 2.13 | F 55.41 | c) 1,4,7-Tris(carboxylatomethyl)-10-[(3-aza-4-oxo-5-methyl-5-yl)-acid N-(1H,1H,2H,2H,4H,4H,-3,6,9,12-tetraoxaperfluorohexadecyl)-N-(2-methoxyethyl)amide]-1,4,7,10-tetraazacyclododecane, Gd complex 8 g (12.32 mmol) of the title compound from Example 2b, 1.42 g (12.32 mmol) of N-hydroxysuccinimide, 1.04 g (24.64 mmol) of lithium chloride and 7.76 g (12.32 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 3.18 g (15.4 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 9.2 g (56% of theory) of a colourless solid
Water content (Karl Fischer): 5.8%
Elemental analysis (based on the anhydrous substance):

| calc.: | C 32.39 | H 3.36 | N 6.66 | F 28.63 | Gd 12.47 |
|---|---|---|---|---|---|
| fnd.: | C 32.51 | H 3.41 | N 6.64 | F 28.51 | Gd 12.39 |

Example 3 a) 2H,2H,4H,4H,-3,6,9,12-Tetraoxaperfluorotridecanoic acid 72.8 g (375 mmol) of tert-butyl bromoacetate are added at 0° C. to 100 g (251.21 mmol) of 1H,1H,-3,6,9-trioxaperfluoro-1-decanol (Apollo) and 28.1 g (500 mmol) of finely powdered potassium hydroxide and a catalytic amount (2 g) of tetra-n-butylammonium hydrogensulphate in 800 ml of toluene and the mixture is stirred at this temperature for 2 h and at room temperature for 12 h. The reaction solution is treated with 1500 ml of ethyl acetate and 800 ml of water. The organic phase is separated off and washed twice with 500 ml each of water, subsequently dried over magnesium sulphate and evaporated to dryness in vacuo. The residue is suspended in a mixture consisting of 1200 ml of methanol and 0.5 M sodium hydroxide solution in the ratio 2:1 and subsequently heated at 60° C. for 12 h. For workup, the reaction mixture is neutralized by treating with AMBERLITE® IR 120 (H$^+$ form) cation exchange resin, filtered off from the exchanger, evaporated to dryness and chromatographed on silica gel (eluent: ethyl acetate/hexane 1:3).

Yield: 67.5 g (59% of theory) of a colourless oil
Elemental analysis:

| calc.: | C 23.70 | H 1.10 | F 54.15 |
|---|---|---|---|
| fnd.: | C 23.93 | H 1.14 | F 54.02 | b) (2H,2H,4H,4H,-3,6,9,12-Tetraoxaperfluorotridecanoic acid)N-methylamide 15.3 g (120 mmol) of oxalyl chloride are added to 40 g (87.70 mmol) of the title compound from Example 3a in 500 ml of dichloromethane and the mixture is stirred at room temperature for 14 h. It is evaporated to dryness in vacuo, the residue is dissolved in 400 ml of dichloromethane, methylamine gas is passed into the solution at 0° C. for about 2 h and the mixture is subsequently stirred at room temperature for 4 h. The reaction solution is treated with 400 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 35.4 g (86% of theory) of a colourless oil
Elemental analysis:

| calc.: | C 25.60 | H 1.72 | N 2.99 | F 52.64 |
|---|---|---|---|---|
| fnd.: | C 25.82 | H 1.75 | N 2.94 | F 52.48 | c) N-Methyl-(1H,1H,2H,2H,4H,4H,-3,6,9,12-tetraoxaperfluorotridecyl)amine 34 g (72.47 mmol) of the title compound from Example 3b in 150 ml of THF are treated with 50 ml of 10 M boranedimethyl sulphide (in THF) and heated under reflux for 5 h. The mixture is cooled to 0° C., 100 ml of methanol are added dropwise, and it is stirred at room temperature for 1 h and subsequently evaporated to dryness in vacuo. The residue is taken up in a mixture of 300 ml of ethanol/50 ml of 1 M hydrochloric acid and stirred at 40° C. for 14 h. The mixture is evaporated to dryness in vacuo, and the residue is taken up in 300 ml of 5% strength sodium hydroxide solution and extracted three times with 300 ml each of dichloromethane. The combined organic phases are dried over magnesium sulphate, evaporated to dryness in vacuo and the residue is chromatographed on silica gel (eluent: dichloromethane/methanol 10:1).

Yield: 27.9 g (85% of theory) of a colourless oil
Elemental analysis:

| | | | | |
|---|---|---|---|---|
| calc.: | C 26.39 | H 2.21 | N 3.08 | F 54.26 |
| fnd.: | C 26.54 | H 2.18 | N 3.07 | F 54.21 | d) 6-N-Benzyloxycarbonyl-2-N-trifluoroacetyl-L-lysine[N-methyl-(1H,1H,2H,2H,4H,4H,-3,6,9,12-tetraoxaperfluorotridecyl)]amide 24.7 g (100 mmol) of EEDQ (ethyl 2-ethoxy-1,2-dihydroquinoline-1-carboxylate) are added at 0° C. to 18.82 g (50 mmol) of 6-N-benzyloxycarbonyl-2-N-trifluoroacetyl-L-lysine (prepared according to EP 01/08498) and 22.76 g (50 mmol) of the title compound from Example 3c in 200 ml of THF and the mixture is stirred at room temperature for 16 h. It is evaporated to dryness in vacuo and the residue is chromatographed on silica gel (eluent: dichloromethane/methanol 20:1).

Yield: 31.7 g (78% of theory) of a colourless viscous oil.
Elemental analysis:

| | | | | |
|---|---|---|---|---|
| calc.: | C 38.39 | H 3.35 | N 5.17 | F 37.37 |
| fnd.: | C 38.60 | H 3.42 | N 5.10 | F 37.12 | e) 6-N-Benzyloxycarbonyl-L-lysine[N-methyl-(1H,1H,2H,2H,4H,4H,-3,6,9,12-tetraoxaperfluorotridecyl)]amide Ammonia gas is passed into a solution of 30 g (36.88 mmol) of the title compound from Example 3d in 250 ml of ethanol at 0° C. for 1 h, and the mixture is subsequently stirred at 0° C. for 4 h. It is evaporated to dryness in vacuo and the residue is precipitated from water by stirring. The solid is filtered off and dried in vacuo at 50° C.

Yield: 25.2 g (95% of theory) of an amorphous solid.
Elemental analysis:

| | | | | |
|---|---|---|---|---|
| calc.: | C 40.18 | H 3.93 | N 5.86 | F 34.42 |
| fnd.: | C 40.29 | H 3.95 | N 5.83 | F 34.37 | f) 6-N-Benzyloxycarbonyl-2-N-[1-O-α-d-carbonylmethyl-(2,3,4,6-tetra-O-benzyl)-mannopyranose]-L-lysine[N-methyl-(1H,1H,2H,2H,4H,4H,-3,6,9,12-tetraoxaperfluorotridecyl)]amide 8.63 g (41.81 mmol) of dicyclohexylcarbodiimide are added at 0° C. to a solution of 24.0 g (33.45 mmol) of the title compound from Example 3e and 20.03 g (33.45 mmol) of 1-O-α-d-carbonylmethyl-(2,3,4,6-tetra-O-benzyl)mannopyranose (prepared according to WO 99/01160 A1) and 3.85 g (33.45 mmol) of N-hydroxysuccinimide in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 34.2 g (79% of theory) of a colourless viscous oil.
Elemental analysis:

| | | | | |
|---|---|---|---|---|
| calc.: | C 55.51 | H 4.97 | N 3.24 | F 19.03 |
| fnd.: | C 55.76 | H 5.01 | N 3.20 | F 18.96 | g) 2-N-(1-O-α-d-Carbonylmethylmannopyranose)-L-lysine[N-methyl-(1H,1H,2H,2H,-4H,4H,3,6,9,12-tetraoxaperfluorotridecyl)]amide 5.0 g of palladium catalyst (10% Pd/C) are added to a solution of 33.0 g (25.42 mmol) of the title compound from Example 3f in 600 ml of ethanol and the mixture is hydrogenated at room temperature for 24 h. It is filtered off from the catalyst and the filtrate is evaporated to dryness in vacuo.

Yield: 20.6 g (quantitative) of a colourless solid.
Elemental analysis:

| | | | | |
|---|---|---|---|---|
| calc.: | C 35.88 | H 4.27 | N 5.23 | F 30.74 |
| fnd.: | C 36.03 | H 4.32 | N 5.19 | F 30.59 | h) 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(1H,1H,2H,2H,4H,4H,-3,6,9,12-tetraoxaperfluorotridecyl)]amide, Gd complex 15 g (18.67 mmol) of the title compound from Example 3g, 2.15 g (18.67 mmol) of N-hydroxysuccinimide, 1.58 g (37.34 mmol) of lithium chloride and 11.76 g (18.67 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 4.82 g (23.34 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 15.6 g (55% of theory) of a colourless solid
Water content (Karl Fischer): 7.0%
Elemental analysis (based on the anhydrous substance):

| | | | | | |
|---|---|---|---|---|---|
| calc.: | C 36.49 | H 4.42 | N 7.92 | F 17.45 | Gd 11.11 |
| fnd.: | C 36.75 | H 4.45 | N 7.89 | F 17.39 | Gd 11.04 |

Example 4 a) (2H,2H,4H,4H,-3,6,9,12-Tetraoxaperfluorotridecanoic acid)N-2-(methoxyethyl)-amide 3.19 g (25 mmol) of oxalyl chloride are added to 10 g (21.92 mmol) of the title compound from Example 3a in 100 ml of dichloromethane and the mixture is stirred at room temperature for 14 h. It is evaporated to dryness in vacuo, the residue is dissolved in 100 ml of dichloromethane, 3.29 g (43.84 mmol) of 2-methoxyethylamine (Aldrich) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 9.5 g (84% of theory) of a colourless wax
Elemental analysis:

| calc.: | C 28.08 | H 2.36 | N 2.73 | F 48.12 |
|---|---|---|---|---|
| fnd.: | C 28.26 | H 2.40 | N 2.71 | F 47.98 | b) N-2-Methoxyethyl-(1H,1H,2H,2H,4H,4H,-3,6,9,12-tetraoxaperfluorotridecyl)amine 9.0 g (17.54 mmol) of the title compound from Example 4a in 50 ml of THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. It is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 7.5 g (86% of theory) of a colourless oil
Elemental analysis:

| calc.: | C 28.87 | H 2.83 | N 2.81 | F 49.47 |
|---|---|---|---|---|
| fnd.: | C 29.02 | H 2.87 | N 2.78 | F 49.31 | c) 1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorotridecyl)-N-(2-methoxyethyl)amide]1,4,7,10-tetraazacyclododecane, Gd complex 7.0 g (14.02 mmol) of the title compound from Example 4b, 1.61 g (14.02 mmol) of N-hydroxysuccinimide, 1.19 g (28.04 mmol) of lithium chloride and 8.83 g (14.02 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 3.62 g (17.53 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 8.5 g (51% of theory) of a colourless solid
Water content (Karl Fischer): 6.7%
Elemental analysis (based on the anhydrous substance):

| calc.: | C 33.52 | H 3.81 | N 7.56 | F 22.23 | Gd 14.15 |
|---|---|---|---|---|---|
| fnd.: | C 33.62 | H 3.84 | N 7.52 | F 22.14 | Gd 14.07 |

Example 5 a) 1H,1H,-3,6,9-Trioxa-2,5,8-trimethylperfluorododecan-1-ol 3.76 g (99.4 mmol) of sodium borohydride are added to 100 g (150.58 mmol) of 3,6,9-trioxa-2,5,8-trimethylperfluorotridecanoyl fluoride (Oakwood) 500 ml dioxane and the mixture is stirred at 60° C. for 2 h. The reaction solution is poured 500 ml of ice water, and extracted three times with 300 ml each of diethyl ether. The combined organic phases are dried over magnesium sulphate, evaporated to dryness in vacuo and chromatographed on silica gel (eluent: ethyl acetate/hexane 1:2).

Yield: 83.1 g (85% of theory) of a colourless oil
Elemental analysis:

| calc.: | C 22.24 | H 0.47 | F 67.42 |
|---|---|---|---|
| fnd.: | C 22.36 | H 0.51 | F 67.29 | b) 2H,2H,4H,4H,-3,6,9,12-Tetraoxa-5,8,11-trimethylperfluoropentadecanoic acid 22.3 g (115 mmol) of tert-butyl bromoacetate are added at 0° C. to 50 g (77.15 mmol) of the title compound from Example 5a and 8.5 g (152 mmol) of finely powdered potassium hydroxide and a catalytic amount (1 g) of tetra-n-butylammonium hydrogen-sulphate in 400 ml of toluene and the mixture is stirred at this temperature for 2 h and at room temperature for 12 h. The reaction solution is treated with 1000 ml of ethyl acetate and 500 ml of water. The organic phase is separated off and washed twice with 300 ml each of water, subsequently dried over magnesium sulphate and evaporated to dryness in vacuo. The residue is suspended in a mixture consisting of 800 ml of methanol and 0.5 M sodium hydroxide solution in the ratio 2:1 and subsequently heated at 60° C. for 12 h. For work up, the reaction mixture is neutralized by treating with AMBERLITE® IR 120 (H+ form) cation exchange resin, filtered off from the exchanger, evaporated to dryness and chromatographed on silica gel (eluent: ethyl acetate/hexane 1:3).

Yield: 24.0 g (44% of theory) of a colourless wax
Elemental analysis:

| calc.: | C 23.81 | H 0.71 | F 61.88 |
|---|---|---|---|
| fnd.: | C 24.02 | H 0.74 | F 61.56 | c) (2H,2H,4H,4H,-3,6,9,12-Tetraoxa-5,8,11-trimethylperfluoropentadecanoic acid)N-methylamide 5.1 g (40 mmol) of oxalyl chloride are added to 21 g (29.74 mmol) of the title compound from Example 5b in 200 ml of dichloromethane and the mixture is stirred at room temperature for 14 h. It is evaporated to dryness in vacuo, the residue is taken up in 200 ml of dichloromethane, methylamine gas is passed into the solution at 0° C. for about 2 h and the mixture is subsequently stirred at room temperature for 4 h. The reaction solution is treated with 200 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 17.3 g (81% of theory) of a colourless wax

Elemental analysis:

| calc.: | C 25.05 | H 1.12 | N 1.95 | F 60.76 |
|---|---|---|---|---|
| fnd.: | C 25.22 | H 1.17 | N 1.93 | F 60.54 | d) N-Methyl-(2H,2H,4H,4H,-3,6,9,12-tetraoxa-5,8,11-trimethylperfluoropentadecyl)-amine 16.5 g (22.94 mmol) of the title compound from Example 5c in 50 ml of THF are treated with 20 ml of 10 M boranedimethyl sulphide (in THF) and heated under reflux for 5 h. The mixture is cooled to 0° C., 30 ml of methanol are added dropwise, and it is stirred at room temperature for 1 h and subsequently evaporated to dryness in vacuo. The residue is taken up in a mixture of 100 ml of ethanol/15 ml of 1 M hydrochloric acid and stirred at 40° C. for 14 h. It is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 13.6 g (84% of theory) of a colourless wax

Elemental analysis:

| calc.: | C 25.55 | H 1.43 | N 1.99 | F 61.69 |
|---|---|---|---|---|
| fnd.: | C 25.72 | H 1.46 | N 1.95 | F 61.53 | e) 6-N-Benzyloxycarbonyl-2-N-trifluoroacetyl-L-lysine[N-methyl-(2H,2H,4H,4H,-3,6,9,12-tetraoxa-5,8,11-trimethylperfluoropentadecyl)]amide 9.88 g (40 mmol) of EEDQ (ethyl 2-ethoxy-1,2-dihydroquinoline-1-carboxylate) are added at 0° C. to 7.53 g (20 mmol) of 6-N-benzyloxycarbonyl-2-N-trifluoroacetyl-L-lysine (prepared according to EP 01/08498) and 14.10 g (20 mmol) of the title compound from Example 5d in 200 ml of THF and the mixture is stirred at room temperature for 16 h. It is evaporated to dryness in vacuo and the residue is chromatographed on silica gel (eluent: dichloromethane/methanol 20:1).

Yield: 17.5 g (82% of theory) of an amorphous solid.

Elemental analysis:

| calc.: | C 35.01 | H 2.56 | N 3.95 | F 46.44 |
|---|---|---|---|---|
| fnd.: | C 35.23 | H 2.60 | N 3.91 | F 46.27 | f) 6-N-Benzyloxycarbonyl-L-lysine[N-methyl-(2H,2H,4H,4H,-3,6,9,12-tetraoxa-5,8,11-trimethylperfluoropentadecyl)]amide Ammonia gas is passed into a solution of 17 g (15.98 mmol) of the title compound from Example 5e in 100 ml of ethanol at 0° C. for 1 h, and the mixture is subsequently stirred at 0° C. for 4 h. It is evaporated to dryness in vacuo and the residue is precipitated from water by stirring. The solid is filtered off and dried in vacuo at 50° C.

Yield: 14.9 g (97% of theory) of an amorphous solid.

Elemental analysis:

| calc.: | C 36.00 | H 2.92 | N 4.34 | F 45.16 |
|---|---|---|---|---|
| fnd.: | C 36.19 | H 2.96 | N 4.29 | F 44.98 | g) 6-N-Benzyloxycarbonyl-2-N-[1-O-α-d-carbonylmethyl-(2,3,4,6-tetra-O-benzyl)-mannopyranose]-L-lysine[N-methyl-(2H,2H,4H,4H,-3,6,9,12-tetraoxa-5,8,11-trimethylperfluoropentadecyl)]amide 3.81 g (18.48 mmol) of dicyclohexylcarbodiimide are added at 0° C. to a solution of 14.3 g (14.78 mmol) of the title compound from Example 5f and 8.85 g (14.78 mmol) of 1-O-α-d-carbonylmethyl-(2,3,4,6-tetra-O-benzyl)mannopyranose (prepared according to WO 99/01160 A1) and 1.70 g (14.78 mmol) of N-hydroxysuccinimide in 100 ml of dimethylformamide, the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 18.8 g (82% of theory) of a colourless viscous oil.

Elemental analysis:

| calc.: | C 50.43 | H 4.17 | N 2.71 | F 28.22 |
|---|---|---|---|---|
| fnd.: | C 50.68 | H 4.22 | N 2.68 | F 28.09 | h) 2-N-(1-O-α-d-Carbonylmethylmannopyranose)-L-lysine[N-methyl-(2H,2H,4H,4H,-3,6,9,12-tetraoxa-5,8,11-trimethylperfluoropentadecyl)]amide 3.0 g of palladium catalyst (10% Pd/C) are added to a solution of 18.0 g (11.63 mmol) of the title compound from Example 5g in 300 ml of ethanol and the mixture is hydrogenated at room temperature for 24 h. It is filtered off from the catalyst and the filtrate is evaporated to dryness in vacuo.

Yield: 12.4 g (quantitative) of a colourless solid.

Elemental analysis:

| calc.: | C 33.06 | H 3.25 | N 3.99 | F 41.47 |
|---|---|---|---|---|
| fnd.: | C 33.39 | H 3.31 | N 3.94 | F 41.18 | i) 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(2H,2H,4H,4H,-3,6,9,12-tetraoxa-5,8,11-trimethylperfluoropentadecyl)] amide, Gd complex 11.8 g (11.20 mmol) of the title compound from Example 5h, 1.29 g (11.20 mmol) of N-hydroxysuccinimide, 0.95 g (22.40 mmol) of lithium chloride and 7.05 g (11.20 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.89 g (14.00 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 11.7 g (58% of theory) of a colourless solid
Water content (Karl Fischer): 7.4%
Elemental analysis (based on the anhydrous substance):

| calc.: | C 34.62 | H 3.75 | N 6.73 | F 26.24 | Gd 9.44 |
|---|---|---|---|---|---|
| fnd.: | C 34.78 | H 3.78 | N 6.75 | F 26.09 | Gd 9.36 |

Example 6 a) (2H,2H,4H,4H,-3,6,9,12-Tetraoxa-5,8,11-trimethylperfluoropentadecanoic acid)N-2-(methoxyethyl) amide 2.55 g (20 mmol) of oxalyl chloride are added to 10 g (14.16 mmol) of the title compound from Example 5b in 100 ml of dichloromethane and the mixture is stirred at room temperature for 14 h. The mixture is evaporated to dryness in vacuo, the residue is dissolved in 100 ml dichloromethane, 2.13 g (28.32 mmol) of 2-methoxyethylamine (Aldrich) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 10.1 g (93% of theory) of a colourless wax
Elemental analysis:

| calc.: | C 26.75 | H 1.58 | N 1.84 | F 57.25 |
|---|---|---|---|---|
| fnd.: | C 26.88 | H 1.64 | N 1.82 | F 57.11 | b) N-2-Methoxyethyl-(2H,2H,4H,4H,-3,6,9,12-tetraoxa-5,8,11-trimethylperfluoropentadecyl)amine 9.5 g (12.45 mmol) of the title compound from Example 6a in 50 ml THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. The mixture is evaporated to dryness in vacuo, the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.2 g (88% of theory) of a colourless oil
Elemental analysis:

| calc.: | C 27.25 | H 1.88 | N 1.87 | F 58.32 |
|---|---|---|---|---|
| fnd.: | C 27.51 | H 1.90 | N 1.88 | F 58.16 | c) 1,4,7-Tris(carboxylatomethyl)-10-[(3-aza-4-oxo-5-methyl-5-yl)acid N-(2H,2H,4H,4H,-3,6,9,12-tetraoxa-5,8,11-trimethylperfluoropentadecyl)-N-(2-methoxyethyl)amide]1,4,7,10-tetraazacyclododecane, Gd complex 7.6 g (10.14 mmol) of the title compound from Example 6b, 1.17 g (10.14 mmol) of N-hydroxysuccinimide, 0.86 g (20.28 mmol) of lithium chloride and 6.39 g (10.14 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml dimethyl sulphoxide. 2.62 g (12.68 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 7.7 g (52% of theory) of a colourless solid
Water content (Karl Fischer): 7.0%
Elemental analysis (based on the anhydrous substance):

| calc.: | C 31.77 | H 3.11 | N 6.17 | F 32.11 | Gd 11.55 |
|---|---|---|---|---|---|
| fnd.: | C 31.89 | H 3.14 | N 6.19 | F 32.01 | Gd 11.48 |

Example 7 a) 1H,1H,-3,6,9,12-Tetraoxa-2,5,8,11-tetramethylperfluoropentadecan-1-ol 3.01 g (79.5 mmol) of sodium borohydride are added to 100 g (120.46 mmol) of 3,6,9,12-tetraoxa-2,5,8,11-tetramethylperfluorotridecanoyl fluoride (Oakwood) 500 ml of dioxane and the mixture is stirred at 60° C. for 2 h. The reaction solution is poured 500 ml of ice water, and extracted three times with 300 ml each of diethyl ether. The combined organic phases are dried over magnesium sulphate, evaporated to dryness in vacuo and chromatographed on silica gel (eluent: ethyl acetate/hexane 1:2).

Yield: 87.3 g (89% of theory) of a colourless oil
Elemental analysis:

| calc.: | C 22.13 | H 0.37 | F 67.67 |
|---|---|---|---|
| fnd.: | C 22.19 | H 0.37 | F 67.58 | b) 3,6,9,12,15-Pentaoxa-5,8,11,14-tetramethylperfluorooctadecanoic acid 17.8 g (92 mmol) of tert-butyl bromoacetate are added at 0° C. to 50 g (61.41 mmol) of the title compound from Example 7a and 6.88 g (123 mmol) of finely powdered potassium hydroxide and a catalytic amount (1 g) of tetra-n-butylammonium hydrogensulphate in 400 ml of toluene and the mixture is stirred at this temperature for 2 h and at room temperature for 12 h. The reaction solution is treated with 1000 ml of ethyl acetate and treated with 500 ml of water. The organic phase is separated off and washed twice with 300 ml each of water, subsequently dried over magnesium sulphate and evaporated to dryness in vacuo. The residue is suspended in a mixture consisting of 800 ml of methanol and 0.5 M sodium hydroxide solution in the ratio 2:1 and subsequently heated at 60° C. for 12 h. For workup, the reaction mixture is neutralized by treating with AMBERLITE® IR 120 (H⁺ form) cation exchange resin, filtered off from the exchanger, evaporated to dryness and chromatographed on silica gel (eluent: ethyl acetate/hexane 1:3).

Yield: 20.9 g (39% of theory) of a colourless wax
Elemental analysis:

| calc.: | C 23.41 | H 0.58 | F 63.17 |
|---|---|---|---|
| fnd.: | C 23.66 | H 0.61 | F 62.94 | c) (3,6,9,12,15-Pentaoxa-5,8,11,14-tetramethylperfluorooctadecanoic acid)N-methyl-amide 5.1 g (40 mmol) of oxalyl chloride are added to 20 g (22.93 mmol) of the title compound from Example 7b in 200 ml of dichloromethane and the mixture is stirred at room temperature for 14 h. It is evaporated to dryness in vacuo, the residue is dissolved in 200 ml of dichloromethane, methylamine gas is passed into the solution at 0° C. for about 2 h and the mixture is subsequently stirred at room temperature for 4 h. The reaction solution is treated with 200 ml 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 15.0 g (74% of theory) of a colourless wax
Elemental analysis:

| calc.: | C 24.42 | H 0.91 | N 1.58 | F 62.24 |
|---|---|---|---|---|
| fnd.: | C 24.59 | H 0.92 | N 1.56 | F 62.03 | d) N-Methyl-(3,6,9,12,15-pentaoxa-5,8,11,14-tetramethylperfluorooctadecyl)amine 14.5 g (16.38 mmol) of the title compound from Example 7c in 50 ml of THF are treated with 15 ml of 10 M boranedimethyl sulphide (in THF) and the mixture is heated under reflux for 5 h. It is cooled to 0° C., 30 ml of methanol are added dropwise, and it is stirred at room temperature for 1 h and subsequently evaporated to dryness in vacuo. The residue is taken up in a mixture of 100 ml of ethanol/15 ml of 1 M hydrochloric acid and stirred at 40° C. for 14 h. The mixture is evaporated to dryness in vacuo, the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 12.6 g (88% of theory) of a colourless wax
Elemental analysis:

| calc.: | C 24.82 | H 1.16 | N 1.61 | F 63.24 |
|---|---|---|---|---|
| fnd.: | C 24.99 | H 1.19 | N 1.63 | F 62.98 | e) 6-N-Benzyloxycarbonyl-2-N-trifluoroacetyl-L-lysine[N-methyl-(3,6,9,12,15-pentaoxa-5,8,11,14-tetramethylperfluorooctadecyl)]amide 4.94 g (20 mmol) of EEDQ (ethyl 2-ethoxy-1,2-dihydroquinoline-1-carboxylate) are added at 0° C. to 3.76 g (10 mmol) of 6-N-benzyloxycarbonyl-2-N-trifluoroacetyl-L-lysine (prepared according to EP 01/08498) and 8.71 g (10 mmol) of the title compound from Example 7d in 200 ml THF and the mixture is stirred at room temperature for 16 h. It is evaporated to dryness in vacuo and the residue is chromatographed on silica gel (eluent: dichloromethane/methanol 20:1).

Yield: 10.5 g (85% of theory) of an amorphous solid.
Elemental analysis:

| calc.: | C 33.21 | H 2.21 | N 3.42 | F 49.44 |
|---|---|---|---|---|
| fnd.: | C 33.52 | H 2.29 | N 3.37 | F 49.34 | f) 6-N-Benzyloxycarbonyl-L-lysine[N-methyl-(3,6,9,12,15-pentaoxa-5,8,11,14-tetramethylperfluorooctadecyl)]amide Ammonia gas is passed into a solution of 10 g (8.13 mmol) of the title compound from Example 7e in 100 ml of ethanol at 0° C. for 1 h, and the mixture is subsequently stirred at 0° C. for 4 h. It is evaporated to dryness in vacuo and the residue is precipitated from water by stirring. The solid is filtered off and dried in vacuo at 50° C.

Yield: 9.1 g (99% of theory) of an amorphous solid.
Elemental analysis:

| calc.: | C 33.91 | H 2.49 | N 3.71 | F 48.60 |
|---|---|---|---|---|
| fnd.: | C 34.12 | H 2.52 | N 3.75 | F 48.41 | g) 6-N-Benzyloxycarbonyl-2-N-[1-O-α-d-carbonylmethyl-(2,3,4,6-tetra-O-benzyl)-mannopyranose]-L-lysine[N-methyl-(3,6,9,12,15-pentaoxa-5,8,11,14-tetramethylperfluorooctadecyl)]amide 1.93 g (9.38 mmol) of dicyclohexylcarbodiimide are added at 0° C. to a solution of 8.5 g (7.50 mmol) of the title compound from Example 7f and 4.49 g (7.50 mmol) of 1-O-α-d-carbonylmethyl-(2,3,4,6-tetra-O-benzyl)mannopyranose (prepared according to WO 99/01160 A1) and 863 mg (7.50 mmol) of N-hydroxysuccinimide in 100 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 10.8 g (84% of theory) of a colourless viscous oil.
Elemental analysis:

| calc.: | C 47.65 | H 3.76 | N 2.45 | F 32.14 |
|---|---|---|---|---|
| fnd.: | C 47.79 | H 3.80 | N 2.45 | F 31.95 | h) 2-N-(1-O-α-d-Carbonylmethylmannopyranose)-L-lysine[N-methyl-(3,6,9,12,15-pentaoxa-5,8,11,14-tetramethylperfluorooctadecyl)]amide 2.0 g of palladium catalyst (10% Pd/C) are added to a solution of 10.2 g (5.95 mmol) of the title compound from Example 7g in 200 ml of ethanol and the mixture is hydrogenated at room temperature for 24 h. It is filtered off from the catalyst and the filtrate is evaporated to dryness in vacuo.

Yield: 7.3 g (quantitative) of a colourless solid.
Elemental analysis:

| calc.: | C 31.52 | H 2.81 | N 3.45 | F 45.18 |
|---|---|---|---|---|
| fnd.: | C 31.77 | H 2.94 | N 3.41 | F 44.99 | i) 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(3,6,9,12,15-pentaoxa-5,8,11,14-tetramethylperfluorooctadecyl)]amide, Gd complex 6.8 g (5.58 mmol) of the title compound from Example 7h, 642 mg (5.58 mmol) of N-hydroxysuccinimide, 473 mg (11.16 mmol) of lithium chloride and 3.51 g (5.58 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 100 ml of dimethyl sulphoxide. 1.44 g (6.98 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 7.1 g (64% of theory) of a colourless solid
Water content (Karl Fischer): 7.5%
Elemental analysis (based on the anhydrous substance):

| calc.: | C 33.45 | H 3.41 | N 6.12 | F 30.09 | Gd 8.59 |
|---|---|---|---|---|---|
| fnd.: | C 33.64 | H 3.42 | N 6.06 | F 30.14 | Gd 8.52 |

Example 8 a) (3,6,9,12,15-Pentaoxa-5,8,11,14-tetramethylperfluorooctadecanoic acid)N-2-(methoxyethyl)amide 2.55 g (20 mmol) of oxalyl chloride are added to 10 g (11.47 mmol) of the title compound from Example 7b in 100 ml of dichloromethane and the mixture is stirred at room temperature for 14 h. It is evaporated to dryness in vacuo, the residue is dissolved in 100 ml of dichloromethane, 1.72 g (22.94 mmol) of 2-methoxyethylamine (Aldrich) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 9.5 g (89% of theory) of a colourless wax
Elemental analysis:

| calc.: | C 25.85 | H 1.30 | N 1.51 | F 59.29 |
|---|---|---|---|---|
| fnd.: | C 26.00 | H 1.32 | N 1.54 | F 59.08 | b) N-2-Methoxyethyl-(3,6,9,12,15-pentaoxa-5,8,11,14-tetramethylperfluorooctadecyl)-amine 9.0 g (9.68 mmol) of the title compound from Example 8a in 50 ml of THF are treated with 15 ml of 10 M boranedimethyl sulphide (in THF) and the mixture is heated under reflux for 5 h. It is cooled to 0° C., 20 ml of methanol are added dropwise, and the mixture is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. The mixture is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.1 g (91% of theory) of a colourless oil
Elemental analysis:

| calc.: | C 26.25 | H 1.54 | N 1.53 | F 60.19 |
|---|---|---|---|---|
| fnd.: | C 26.29 | H 1.58 | N 1.47 | F 60.11 | c) 1,4,7-Tris(carboxylatomethyl)-10-[(3-aza-4-oxo-5-methyl-5-yl)acid N-(3,6,9,12,15-pentaoxa-5,8,11,14-tetramethylperfluorooctadecyl)-N-(2-methoxyethyl)amide]1,4,7,10-tetraazacyclododecane, Gd complex 7.5 g (8.19 mmol) of the title compound from Example 8b, 943 mg (8.19 mmol) of N-hydroxysuccinimide, 694 mg (16.38 mmol) of lithium chloride and 5.16 g (8.19 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.11 g (10.24 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 7.9 g (58% of theory) of a colourless solid
Water content (Karl Fischer): 7.3%

Elemental analysis (based on the anhydrous substance):

| | | | | | |
|---|---|---|---|---|---|
| calc.: | C 30.68 | H 2.77 | N 5.50 | F 36.08 | Gd 10.30 |
| fnd.: | C 30.81 | H 2.79 | N 5.50 | F 35.97 | Gd 10.22 |

Example 9 a) 1-N-(Benzyloxycarbonyl)-1H,1H,2H,2H,5H,5H,7H,7H-3-aza-4-oxo-6,9,12,15-tetraoxaperfluorohexadecylamine 3.19 g (25 mmol) of oxalyl chloride are added to 10 g (21.92 mmol) of the title compound from Example 3a in 100 ml of dichloromethane and the mixture is stirred at room temperature for 14 h. It is evaporated to dryness in vacuo, the residue is dissolved in 100 ml of dichloromethane, 8.52 g (43.84 mmol) of N-benzyloxycarbonyl-ethylenediamine (Atwell et al., *Synthesis,* 1984, 1032-1033) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 11.0 g (79% of theory) of a colourless wax
Elemental analysis:

| | | | | |
|---|---|---|---|---|
| calc.: | C 36.09 | H 2.71 | N 4.43 | F 39.06 |
| fnd.: | C 36.22 | H 2.74 | N 4.38 | F 38.89 | b) 1-N-(Benzyloxycarbonyl)-1H,1H,2H,2H,4H,4H,5H,5H,7H,7H-3-aza-6,9,12,15-tetraoxaperfluorohexadecylamine 10.6 g (16.76 mmol) of the title compound from Example 9a in 50 ml of THF are treated with 15 ml of 10 M boranedimethyl sulphide (in THF) and heated under reflux for 5 h. The mixture is cooled to 0° C., 20 ml of methanol are added dropwise, stirred at room temperature for 1 h and subsequently evaporated to dryness in vacuo. The residue is taken up in a mixture of 100 ml of ethanol/50 ml of 1 M hydrochloric acid and stirred at 40° C. for 14 h. The mixture is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.4 g (81% of theory) of a colourless wax
Elemental analysis:

| | | | | |
|---|---|---|---|---|
| calc.: | C 36.91 | H 3.10 | N 4.53 | F 39.94 |
| fnd.: | C 37.06 | H 3.15 | N 4.48 | F 39.67 | c) N-[2-(Benzyloxycarbonyl)aminoethyl-N-(1H,1H,2H,2H,4H,4H-3,6,9,12-tetraoxaperfluorotridecyl)-2-[2-(2-methoxyethoxy)ethoxy]acetamide 3.34 g (16.18 mmol) of dicyclohexylcarbodiimide is added at 0° C. to a solution of 8 g (12.94 mmol) of the title compound from Example 9b and 2.31 g (12.94 mmol) of [2-(2-methoxyethoxy)ethoxy]acetic acid (Aldrich) and 1.49 g (12.94 mmol) of N-hydroxy-succinimide in 100 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 8.5 g (84% of theory) of a colourless viscous oil.
Elemental analysis:

| | | | | |
|---|---|---|---|---|
| calc.: | C 40.11 | H 4.01 | N 3.60 | F 31.72 |
| fnd.: | C 40.36 | H 4.10 | N 3.53 | F 31.52 | d) N-2-(Aminoethyl)-N-(1H,1H,2H,2H,4H,4H-3,6,9,12-tetraoxaperfluorotridecyl)-2-[2-(2-methoxyethoxy)ethoxy]acetamide 2.0 g of palladium catalyst (10% Pd/C) are added to a solution of 8.2 g (10.53 mmol) of the title compound from Example 9c in 200 ml of ethanol and the mixture is hydrogenated at room temperature for 24 h. It is filtered off from the catalyst and the filtrate is evaporated to dryness in vacuo.

Yield: 6.8 g (quantitative) of a colourless solid.
Elemental analysis:

| | | | | |
|---|---|---|---|---|
| calc.: | C 33.55 | H 3.91 | N 4.35 | F 38.33 |
| fnd.: | C 33.76 | H 3.98 | N 4.17 | F 37.98 | e) N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-3,6,9,12-tetraoxaperfluorotridecyl)-2-[2-(2-methoxyethoxy)ethoxy]acetamide, Gd complex 6.0 g (9.31 mmol) of the title compound from Example 9d, 1.07 g (9.31 mmol) of N-hydroxysuccinimide, 789 mg (18.62 mmol) of lithium chloride and 5.86 g (9.31 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 100 ml of dimethyl sulphoxide. 2.4 g (11.64 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 8.2 g (66% of theory) of a colourless solid
Water content (Karl Fischer): 6.1%
Elemental analysis (based on the anhydrous substance):

| | | | | | |
|---|---|---|---|---|---|
| calc.: | C 35.38 | H 4.25 | N 7.81 | F 19.66 | Gd 12.52 |
| fnd.: | C 35.57 | H 4.31 | N 7.77 | F 19.52 | Gd 12.46 |

Example 10 a) 1-N-(Benzyloxycarbonyl)-1H,1H,2H,2H,5H,5H, 7H,7H-3-aza-4-oxo-6,9,12,15-tetraoxa-8,11,14-trimethylperfluorooctadecylamine 3.19 g (25 mmol) of oxalyl chloride are added to 15 g (21.24 mmol) of the title compound from Example 5b in 100 ml of dichloromethane and the mixture is stirred at room temperature for 14 h. It is evaporated to dryness in vacuo, the residue is dissolved in 100 ml of dichloromethane, 8.26 g (42.48 mmol) of N-benzyloxycarbonyl-ethylenediamine (Atwell et al., *Synthesis*, 1984, 1032-1033) and the mixture is subsequently stirred at room temperature for 4 h. The reaction solution is treated with 100 ml 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 13.9 g (74% of theory) of a colourless wax
Elemental analysis:

| calc.: | C 32.67 | H 1.94 | N 3.17 | F 49.52 |
|---|---|---|---|---|
| fnd.: | C 32.88 | H 1.89 | N 3.04 | F 49.88 | b) 1-N-(Benzyloxycarbonyl)-1H,1H,2H,2H,4H,4H, 5H,5H,7H,7H-3-aza-6,9,12,15-tetraoxa-8,11,14-trimethylperfluorooctadecylamine 13.5 g (15.30 mmol) of the title compound from Example 10a in 50 ml of THF are treated with 15 ml of 10 M boranedimethyl sulphide (in THF) and heated under reflux for 5 h. The mixture is cooled to 0° C., 20 ml of methanol are added dropwise, and the mixture is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. It is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 9.0 g (68% of theory) of a colourless wax
Elemental analysis:

| calc.: | C 33.20 | H 2.21 | N 3.23 | F 50.32 |
|---|---|---|---|---|
| fnd.: | C 33.52 | H 2.29 | N 3.14 | F 50.16 | c) N-[2-(Benzyloxycarbonyl)aminoethyl-N-(1H,1H, 2H,2H,4H,4H-6,9,12,15-tetraoxa-8,11,14-trimethylperfluoropentadecyl)-2-[2-(2-methoxyethoxy)ethoxy]acetamide 2.52 g (12.24 mmol) of dicyclohexylcarbodiimide are added at 0° C. to a solution of 8.5 g (9.79 mmol) of the title compound from Example 10b and 1.74 g (9.79 mmol) of [2-(2-methoxyethoxy)ethoxy]acetic acid (Aldrich) and 1.13 g (9.79 mmol) of N-hydroxy-succinimide in 100 ml of dimethylformamide, and the mixture is stirred at 0° C. for 3 h and subsequently stirred at room temperature for 16 h. It is filtered from the precipitated urea, the filtrate is evaporated to dryness in vacuo and the residue is chromatographed on silica gel (eluent: dichloromethane/methanol 20:1).

Yield: 8.1 g (80% of theory) of a colourless viscous oil.
Elemental analysis:

| calc.: | C 36.20 | H 3.04 | N 2.72 | F 42.48 |
|---|---|---|---|---|
| fnd.: | C 36.44 | H 3.09 | N 2.68 | F 42.21 | d) N-2-(Aminoethyl)-N-(1H,1H,2H,2H,4H,4H-6,9, 12,15-tetraoxa-8,11,14-trimethylperfluoropentadecyl)-2-[2-(2-methoxyethoxy)ethoxy]acetamide 2.0 g of palladium catalyst (10% Pd/C) are added to a solution of 8.0 g (7.78 mmol) of the title compound from Example 10c in 200 ml of ethanol and the mixture is hydrogenated at room temperature for 24 h. It is filtered off from the catalyst and the filtrate is evaporated to dryness in vacuo.

Yield: 7.0 g (quantitative) of a colourless solid.
Elemental analysis:

| calc.: | C 30.89 | H 2.82 | N 3.13 | F 48.85 |
|---|---|---|---|---|
| fnd.: | C 30.98 | H 2.80 | N 3.19 | F 48.67 | e) N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H, 4H,4H-6,9,12,15-tetraoxa-8,11,14-trimethylperfluoropentadecyl)-2-[2-(2-methoxyethoxy)ethoxy]-acetamide, Gd complex 6.5 g (7.27 mmol) of the title compound from Example 10d, 837 mg (7.27 mmol) of N-hydroxysuccinimide, 616 mg (14.54 mmol) of lithium chloride and 4.58 g (7.27 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 100 ml of dimethyl sulphoxide. 1.87 g (9.09 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 8.1 g (69% of theory) of a colourless solid
Water content (Karl Fischer): 6.7%
Elemental analysis (based on the anhydrous substance):

| calc.: | C 33.49 | H 3.55 | N 6.51 | F 29.01 | Gd 10.44 |
|---|---|---|---|---|---|
| fnd.: | C 33.64 | H 3.58 | N 6.46 | F 28.94 | Gd 10.37 |

Example 11 a) 6-N-(Benzyloxycarbonyl)-2-N-(2H,2H,4H,4H-3, 6,9,12,-tetraoxaperfluorotridecanoyl)-L-lysine methyl ester 3.19 g (25 mmol) of oxalyl chloride are added to 10 g (21.92 mmol) of the title compound from Example 3a in 100 ml of dichloromethane and the mixture is stirred at room temperature for 14 h. It is evaporated to dryness in vacuo, the residue is dissolved in 100 ml of dichloromethane, treated with 8.07 g (27.4 mmol) of 6-N-benzyloxycarbonyl-L-lysine methyl ester (Bachem) and 2.75 g (27.4 mmol) of triethylamine and subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 13.5 g (84% of theory) of a colourless wax
Elemental analysis:

| calc.: | C 39.36 | H 3.44 | N 3.82 | F 33.72 |
|---|---|---|---|---|
| fnd.: | C 39.48 | H 3.47 | N 3.74 | F 33.59 | b) 2-N-(2H,2H,4H,4H-3,6,9,12,-tetraoxaperfluorotridecanoyl)-L-lysine methyl ester 2.0 g of palladium catalyst (10% Pd/C) are added to a solution of 13.0 g (17.75 mmol) of the title compound from Example 11a in 200 ml of ethanol and the mixture is hydrogenated at room temperature for 24 h. It is filtered off from the catalyst and the filtrate is evaporated to dryness in vacuo.

Yield: 10.7 g (quantitative) of a colourless solid.
Elemental analysis:

| calc.: | C 32.12 | H 3.20 | N 4.68 | F 41.28 |
|---|---|---|---|---|
| fnd.: | C 32.39 | H 3.32 | N 4.55 | F 40.96 | c) 6-N-[1-O-α-d-Carbonylmethyl-(2,3,4,6-tetra-O-benzyl)mannopyranose]-2-N-(2H,2H,4H,4H-3,6,9,12,-tetraoxaperfluorotridecanoyl)-L-lysine methyl ester 4.44 g (21.51 mmol) of dicyclohexylcarbodiimide are added at 0° C. to a solution of 10.3 g (17.21 mmol) of title compound from Example 11b, 10.30 g (17.21 mmol) of 1-O-α-d-carbonylmethyl-(2,3,4,6-tetra-O-benzyl)mannopyranose (prepared according to WO 99/01160 A1), 1.98 g (17.21 mmol) of N-hydroxysuccinimide and 3.47 g (34.42 mmol) of triethylamine in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 16.6 g (82% of theory) of a colourless viscous oil.
Elemental analysis:

| calc.: | C 52.98 | H 4.70 | N 2.38 | F 20.95 |
|---|---|---|---|---|
| fnd.: | C 53.31 | H 4.78 | N 2.30 | F 20.68 | d) 6-N-[1-O-α-d-Carbonylmethyl-(2,3,4,6-tetra-O-benzyl)mannopyranose]-2-N-(2H,2H,4H,4H-3,6,9,12,-tetraoxaperfluorotridecanoyl)-L-lysine 16.0 g (13.57 mmol) of the title compound from Example 11c are dissolved in 100 ml of methanol and 25 ml of 2 N potassium hydroxide solution and stirred at room temperature for 16 h. The mixture is acidified with 2 N hydrochloric acid, concentrated in vacuo, and extracted three times with 50 ml each of ethyl acetate. The combined organic phases are dried over magnesium sulphate, evaporated to dryness in vacuo and the residue is chromatographed on silica gel (eluent: dichloromethane/methanol 10:1).

Yield: 12.4 g (78% of theory) of a colourless solid.
Elemental analysis:

| calc.: | C 52.58 | H 4.59 | N 2.40 | F 21.20 |
|---|---|---|---|---|
| fnd.: | C 52.69 | H 4.64 | N 2.42 | F 21.00 | e) 6-N-(1-O-α-d-Carbonylmethylmannopyranose)-2-N-(2H,2H,4H,4H-3,6,9,12,-tetraoxaperfluorotridecanoyl)-L-lysine[1,4,7-tris-(carboxylatomethyl)-1,4,7,10-tetraazacyclododecane-10-N-(2-hydroxy-3-yl)] amide, Gd complex 12.0 g (10.30 mmol) of the title compound from Example 11d, 1.18 g (10.30 mmol) of N-hydroxysuccinimide, 873 mg (20.60 mmol) of lithium chloride and 5.91 g (10.30 mmol) of 1,4,7-tris(carboxylatomethyl)-10-[3-amino-2-hydroxypropyl]-1,4,7,10-tetraazacyclododecane, Gd complex (WO 95/17451, Schering AG) are dissolved with gentle warming in 200 ml of dimethylformamide. 2.66 g (12.88 mmol) of dicyclohexyl-carbodiimide are added at 10° C. and the mixture is stirred at room temperature for 48 h. It is filtered off from the precipitated urea and the filtrate is evaporated to dryness in vacuo. The residue is dissolved in 100 ml of methanol, treated with 2.0 g of palladium catalyst (10% Pd/C) and hydrogenated at room temperature for 24 h. It is filtered off from the catalyst and the filtrate is evaporated to dryness in vacuo. The residue is taken up in a little water, filtered off from insoluble constituents, and the filtrate is subsequently purified by chromatography (RP-18; eluent: gradient of water/acetonitrile).

Yield 7.3 g (49% of theory) of a colourless solid
Water content (Karl Fischer): 6.5%
Elemental analysis (based on the anhydrous substance):

| calc.: | C 36.32 | H 4.22 | N 7.21 | F 18.16 | Gd 11.56 |
|---|---|---|---|---|---|
| fnd.: | C 36.39 | H 4.17 | N 7.23 | F 18.06 | Gd 11.47 |

Example 12 a) 6-N-(Benzyloxycarbonyl)-2-N-(2H,2H,4H,4H-3,6,9,12,-tetraoxa-5,8,11-trimethylperfluoropentadecanoyl)-L-lysine methyl ester 3.19 g (25 mmol) of oxalyl chloride are added to 15 g (21.24 mmol) of the title compound from Example 5a in 100 ml of dichloromethane and the mixture is stirred at room temperature for 14 h. It is evaporated to dryness in vacuo, the residue is dissolved in 100 ml of dichloromethane, treated with 7.82 g (26.55 mmol) of 6-N-benzyloxycarbonyl-L-lysine methyl ester (Bachem) and 2.66 g (26.55 mmol) of triethylamine and subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 16.7 g (80% of theory) of a colourless wax
Elemental analysis:

| calc.: | C 35.45 | H 2.56 | N 2.85 | F 44.47 |
|---|---|---|---|---|
| fnd.: | C 35.68 | H 2.59 | N 2.81 | F 44.36 | b) 2-N-(2H,2H,4H,4H-3,6,9,12,-Tetraoxa-5,8,11-trimethylperfluoropentadecanoyl)-L-lysine methyl ester 2.0 g of palladium catalyst (10% Pd/C) are added to a solution of 16.0 g (16.29 mmol) of the title compound from Example 12a in 200 ml of ethanol and the mixture is hydrogenated at room temperature for 24 h. It is filtered off from the catalyst and the filtrate is evaporated to dryness in vacuo.

Yield: 13.9 g (quantitative) of a colourless solid.
Elemental analysis:

| calc.: | C 29.73 | H 2.26 | N 3.30 | F 51.51 |
|---|---|---|---|---|
| fnd.: | C 30.01 | H 2.35 | N 3.19 | F 51.29 | c) 6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine methyl ester 4.10 g (19.89 mmol) of dicyclohexylcarbodiimide are added at 0° C. to a solution of 13.5 g (15.91 mmol) of title compound from Example 12b, 2.83 g (15.91 mmol) of [2-(2-methoxyethoxy)ethoxy]acetic acid (Aldrich) and 1.83 g (15.91 mmol) of N-hydroxy-succinimide in 200 ml of dimethylformamide, the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 12.4 g (77% of theory) of a colourless viscous oil.
Elemental analysis:

| calc.: | C 33.35 | H 3.10 | N 2.78 | F 43.33 |
|---|---|---|---|---|
| fnd.: | C 33.54 | H 3.21 | N 2.68 | F 43.08 | d) 6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine 12.0 g (11.89 mmol) of the title compound from Example 12c are dissolved in 100 ml of methanol and 25 ml of 2 N potassium hydroxide solution and the mixture is stirred at room temperature for 16 h. It is acidified with 2 N hydrochloric acid, concentrated in vacuo, and extracted three times with 50 ml each of ethyl acetate. The combined organic phases are dried over magnesium sulphate, evaporated to dryness in vacuo and the residue is chromatographed on silica gel (eluent: dichloromethane/methanol 10:1).

Yield: 10.8 g (91% of theory) of a colourless solid.

Elemental analysis:

| calc.: | C 32.61 | H 2.94 | N 2.82 | F 43.94 |
|---|---|---|---|---|
| fnd.: | C 32.77 | H 2.91 | N 2.80 | F 43.86 | e) 6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine[1,4,7-tris-(carboxylatomethyl)-1,4,7,10-tetraazacyclododecane-10-N-(2-hydroxy-3-yl)]amide, Gd complex 10.0 g (10.06 mmol) of the title compound from Example 12d, 1.16 g (10.06 mmol) of N-hydroxysuccinimide, 861 mg (20.12 mmol) of lithium chloride and 5.86 g (10.06 mmol) of 1,4,7-tris(carboxylatomethyl)-10-[3-amino-2-hydroxypropyl]-1,4,7,10-tetraazacyclododecane, Gd complex (WO 95/17451, Schering AG) are dissolved with gentle warming in 200 ml of dimethylformamide. 2.62 g (12.57 mmol) of dicyclohexyl-carbodiimide are added at 10° C. and the mixture is stirred at room temperature for 48 h. It is filtered off from the precipitated urea and the filtrate is evaporated to dryness in vacuo. The residue is purified by chromatography (RP-18; eluent: gradient of water/acetonitrile).

Yield 9.1 g (54% of theory) of a colourless solid
Water content (Karl Fischer): 7.2%
Elemental analysis (based on the anhydrous substance):

| calc.: | C 34.09 | H 3.71 | N 6.32 | F 28.19 | Gd 10.14 |
|---|---|---|---|---|---|
| fnd.: | C 34.27 | H 3.78 | N 6.28 | F 28.01 | Gd 10.10 |

Example 13 a) 6-N-Benzyloxycarbonyl-2-N-(2H,2H,4H,4H-3,6,9,12,-tetraoxaperfluorotridecanoyl)-L-lysine 10 g (13.65 mmol) of the title compound from Example 11a are dissolved in 100 ml of methanol and 25 ml of 2 N potassium hydroxide solution and the mixture is stirred at room temperature for 18 h. It is acidified with 2 N hydrochloric acid, evaporated to dryness and the residue is chromatographed on silica gel (eluent: dichloromethane/methanol 10:1).

Yield: 9.4 g (96% of theory) of a colourless solid.
Elemental analysis:

| calc.: | C 38.45 | H 3.23 | N 3.90 | F 34.38 |
|---|---|---|---|---|
| fnd.: | C 38.61 | H 3.27 | N 3.88 | F 34.19 | b) 6-N-Benzyloxycarbonyl-2-N-(2H,2H,4H,4H-3,6,9,12,-tetraoxaperfluorotridecanoyl)-L-lysine(2-{2-[2-(2-methoxyethoxy)ethoxy]ethoxy}ethyl)amide 3.23 g (15.66 mmol) of dicyclohexylcarbodiimide are added at 0° C. to a solution of 9.0 g (12.53 mmol) of the title compound from Example 13a and 2.60 g (19.12 mmol) of (2-{2-[2-(2-methoxyethoxy)ethoxy]ethoxy}ethyl)amine (Whitessides et al., JACS, 1994, 5057-5062) and 1.44 g (12.53 mmol) of N-hydroxysuccinimide in 200 ml of dimethyl-formamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 10:1).

Yield: 8.99 g (79% of theory) of a colourless viscous oil.
Elemental analysis:

| calc.: | C 42.34 | H 4.66 | N 4.63 | F 27.21 |
|---|---|---|---|---|
| fnd.: | C 42.55 | H 4.69 | N 4.57 | F 27.02 | c) 2-N-(2H,2H,4H,4H-3,6,9,12,-Tetraoxaperfluorotridecanoyl)-L-lysine(2-{2-[2-(2-methoxyethoxy)ethoxy]ethoxy}ethyl)amide 1.0 g of palladium catalyst (10% Pd/C) is added to a solution of 8.7 g (9.58 mmol) of the title compound from Example 13b in 100 ml of ethanol and the mixture is hydrogenated at room temperature for 24 h. It is filtered off from the catalyst and the filtrate is evaporated to dryness in vacuo.

Yield: 7.43 g (quantitative) of a colourless solid.
Elemental analysis:

| calc.: | C 37.27 | H 4.69 | N 5.43 | F 31.93 |
|---|---|---|---|---|
| fnd.: | C 37.48 | H 4.81 | N 5.36 | F 31.74 | d) 6-N-[1,4,7-Tris(carboxylatomethyl)-1,4,7,10-tetraazacyclododecane-10-N-(pentanoyl-3-aza-4-oxo-5-methyl-5-yl)]-2-N-(2H,2H,4H,4H-3,6,9,12,-tetraoxaperfluorotridecanoyl)-L-lysine(2-{2-[2-(2-methoxyethoxy)ethoxy]ethoxy}ethyl)amide, Gd complex 7.0 g (9.05 mmol) of the title compound from Example 13c, 1.04 g (9.05 mmol) of N-hydroxysuccinimide, 767 mg (18.10 mmol) of lithium chloride and 5.70 g (9.05 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 100 ml of dimethyl sulphoxide. 2.33 g (11.31 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 7.7 g (57% of theory) of a colourless solid
Water content (Karl Fischer): 6.7%
Elemental analysis (based on the anhydrous substance):

| calc.: | C 37.28 | H 4.66 | N 8.09 | F 17.83 | Gd 11.35 |
|---|---|---|---|---|---|
| fnd.: | C 37.44 | H 4.69 | N 7.98 | F 17.74 | Gd 11.22 |

Example 14 a) 3,5-Dinitrobenzoic acid[(1H,1H,2H,2H,4H,4H,-3,6,9,12-tetraoxaperfluorotridecyl)-methyl]amide A solution of 5.76 g (25 mmol) of dinitrobenzoyl chloride in 100 ml of dichloromethane is added dropwise at 0° C. to 10 g (21.97 mmol) of the title compound from Example 3c and 4.5 g (44 mmol) of triethylamine dissolved in 200 ml of dichloromethane and the mixture is stirred at 0° C. for 3 h. It is treated with 250 ml of 0.5 M hydrochloric acid, and subsequently stirred at room temperature for 10 min. The organic phase is separated off, dried over magnesium sulphate, evaporated to dryness in vacuo and the residue is chromatographed on silica gel (eluent: hexane/ethyl acetate 3:1).

Yield: 12.1 g (85% of theory) of a colourless solid.
Elemental analysis:

| calc.: | C 31.45 | H 1.86 | N 6.47 | F 38.04 |
|---|---|---|---|---|
| fnd.: | C 31.59 | H 1.92 | N 6.41 | F 37.91 | b) 3,5-Diaminobenzoic acid[(1H,1H,2H,2H,4H,4H,-3,6,9,12-tetraoxaperfluorotridecyl)-methyl]amide 3.0 g of palladium catalyst (10% Pd/C) are added to a solution of 11.7 g (18.02 mmol) of the title compound from Example 14a in 300 ml of ethanol and the mixture is hydrogenated at room temperature for 24 h. It is filtered off from the catalyst and the filtrate is evaporated to dryness in vacuo.

Yield: 10.6 g (quantitative) of a yellowish solid.
Elemental analysis:

| calc.: | C 34.65 | H 2.74 | N 7.13 | F 41.91 |
|---|---|---|---|---|
| fnd.: | C 34.87 | H 2.77 | N 7.11 | F 41.79 | c) 3,5-N,N'-Bis[1,4,7-tris(carboxylatomethyl)-1,4,7,10-tetraazacyclododecane-10-N-(pentanoyl-3-aza-4-oxo-5-methyl-5-yl)]benzoic acid[(1H,1H,2H,2H,4H,4H,-3,6,9,12-tetraoxaperfluorotridecyl)methyl]amide, Gd complex 10.0 g (16.97 mmol) of the title compound from Example 14b, 3.91 g (33.94 mmol) of N-hydroxysuccinimide, 2.88 g (67.88 mmol) of lithium chloride and 21.37 g (33.94 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 8.75 g (42.43 mmol) of dicyclohexylcarbodiimide are added at 10° C. and the mixture is stirred at room temperature for 48 h. The solution is poured into 2000 ml of acetone and subsequently stirred for 10 min. The precipitated solid is filtered off and subsequently purified by chromatography (RP-18; eluent: gradient of water/acetonitrile).

Yield 17.7 g (53% of theory) of a colourless solid
Water content (Karl Fischer): 7.8%
Elemental analysis (based on the anhydrous substance):

| calc.: | C 36.44 | H 4.00 | N 10.04 | F 13.62 | Gd 17.35 |
|---|---|---|---|---|---|
| fnd.: | C 36.59 | H 3.97 | N 10.00 | F 13.56 | Gd 17.29 |

Example 15 a) N-Benzyloxycarbonyl-3-{2-[2-(2-methoxyethoxy)ethoxy]ethyl}-L-serine methyl ester 10 ml of a 10% boron trifluoride etherate solution in chloroform are added dropwise at 0° C. to a solution of 11.76 g (50 mmol) of methyl N-benzyloxycarbonyl-L-aziridine-carboxylate (Aldrich) and 4.85 g (23.36 mmol) of 2-[2-(2-methoxyethoxy)ethoxy]-ethanol (Aldrich) in 100 ml of dichloromethane and the mixture is stirred at room temperature for 6 h. The reaction solution is evaporated to dryness in vacuo and the residue is chromatographed on silica gel (eluent: dichloromethane/methanol 10:1).

Yield: 15.4 g (77% of theory) of a colourless oil.
Elemental analysis:

| calc.: | C 57.13 | H 7.32 | N 3.51 |
|---|---|---|---|
| fnd.: | C 57.54 | H 7.52 | N 3.27 | b) N-Benzyloxycarbonyl-3-{2-[2-(2-methoxyethoxy)ethoxy]ethyl}-L-serine 15.0 g (37.55 mmol) of the title compound from Example 15a are dissolved in 100 ml of methanol and 50 ml of 2 N potassium hydroxide solution and the mixture is stirred at room temperature for 16 h. It is acidified with 2 N hydrochloric acid, concentrated in vacuo, and extracted three times with 50 ml each of ethyl acetate. The combined organic phases are dried over magnesium sulphate, evaporated to dryness in vacuo and the residue is chromatographed on silica gel (eluent: dichloromethane/methanol 10:1).

Yield: 12.9 g (89% of theory) of a colourless solid.
Elemental analysis:

| calc.: | C 56.10 | H 7.06 | N 3.63 |
|---|---|---|---|
| fnd.: | C 56.31 | H 7.11 | N 3.59 | c) N-Benzyloxycarbonyl-3-{2-[2-(2-methoxyethoxy)ethoxy]ethyl}-L-serine 1-[(1H,1H,2H, 2H,4H,4H,-3, 6,9,12-tetraoxaperfluorotridecyl)methyl]amide 12.35 g (50 mmol) of EEDQ (ethyl 2-ethoxy-1,2-dihydroquinoline-1-carboxylate) are added at 0° C. to 10 g (25.95 mmol) of the title compound from Example 15b and 11.82 g (25.95 mmol) of the title compound from Example 3c in 100 ml of THF and the mixture is stirred at room temperature for 16 h. It is evaporated to dryness in vacuo and the residue is chromatographed on silica gel (eluent: dichloromethane/methanol 20:1).

Yield: 17.3 g (81% of theory) of a colourless viscous oil.
Elemental analysis:

| calc.: | C 40.89 | H 4.29 | N 3.41 | F 30.03 |
|---|---|---|---|---|
| fnd.: | C 41.07 | H 4.25 | N 3.37 | F 29.87 | d) 3-{2-[2-(2-Methoxyethoxy)ethoxy]ethyl}-L-serine 1-[(1H,1H,2H,2H,4H,4H,-3,6,9,12-tetraoxaperfluorotridecyl)methyl]amide 2.0 g of palladium catalyst (10% Pd/C) are added to a solution of 15.0 g (18.16 mmol) of the title compound from Example 15c in 200 ml of ethanol and the mixture is hydrogenated at room temperature for 24 h. It is filtered off from the catalyst and the filtrate is evaporated to dryness in vacuo.

Yield: 12.5 g (quantitative) of a colourless solid.
Elemental analysis:

| calc.: | C 34.98 | H 4.25 | N 4.07 | F 35.88 |
|---|---|---|---|---|
| fnd.: | C 35.22 | H 4.31 | N 3.95 | F 35.61 | e) N-[1,4,7-Tris(carboxylatomethyl)-1,4,7,10-tetraazacyclododecane-10-N-(pentanoyl-3-aza-4-oxo-5-methyl-5-yl)]-3-{2-[2-(2-methoxyethoxy)ethoxy]ethyl}-L-serine 1-[(1H 1H,2H,2H,4H,4H,-3,6,9,12-tetraoxaperfluorotridecyl)methyl]amide, Gd complex 10.0 g (14.53 mmol) of the title compound from Example 15d, 1.67 g (14.53 mmol) of N-hydroxysuccinimide, 1.22 g (29.06 mmol) of lithium chloride and 9.15 g (14.53 mmol) of 1,4,7-tris(carboxylatomethyl)-10-[1-carboxy-3-aza-4-oxo-5-methylpentan-5-yl]-1,4, 7,10-tetraazacyclododecane, Gd complex (WO 98/24775, Schering AG, (Example 1)) are dissolved with gentle warming in 200 ml of dimethyl sulphoxide. 3.75 g (18.16 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 11.9 g (58% of theory) of a colourless solid
Water content (Karl Fischer): 8.0%
Elemental analysis (based on the anhydrous substance):

| calc.: | C 36.03 | H 4.42 | N 7.54 | F 19.00 | Gd 12.09 |
|---|---|---|---|---|---|
| fnd.: | C 36.19 | H 4.44 | N 7.50 | F 18.96 | Gd 12.01 |

Example 16 a) N-tert-Butyloxycarbonyl-L-glutamic acid 5-benzyl ester 1-[(1H,1H,2H,2H,4H,4H,-3,6,9,12-tetraoxaperfluorotridecyl)methyl]amide 9.88 g (40 mmol) of EEDQ (ethyl 2-ethoxy-1,2-dihydroquinoline-1-carboxylate) are added at 0° C. to 6.75 g (20 mmol) of N-tert-butyloxycarbonyl-L-glutamic acid 5-benzyl ester (Bachem) and 9.10 g (20 mmol) of the title compound from Example 3c in 200 ml of THF and the mixture is stirred at room temperature for 16 h. It is evaporated to dryness in vacuo and the residue is chromatographed on silica gel (eluent: dichloromethane/methanol 20:1).

Yield: 13.2 g (85% of theory) of a colourless viscous oil.
Elemental analysis:

| calc.: | C 41.87 | H 4.03 | N 3.62 | F 31.89 |
|---|---|---|---|---|
| fnd.: | C 41.99 | H 4.08 | N 3.57 | F 31.69 | b) L-Glutamic acid 5-benzyl ester 1-[(1H,1H,2H,2H, 4H,4H,-3,6,9,12-tetraoxaperfluorotridecyl)methyl] amide 25 ml of trifluoroacetic acid are added at 0° C. to a solution of 12.0 g (15.49 mmol) of the title compound from Example 16a in 50 ml of dichloromethane, and the mixture is subsequently stirred at room temperature for 4 h. It is evaporated to dryness in vacuo and the residue is chromatographed on silica gel (eluent: dichloromethane/methanol 10:1).

Yield: 9.3 g (89% of theory) of an amorphous solid.
Elemental analysis:

| calc.: | C 39.18 | H 3.44 | N 4.15 | F 36.62 |
|---|---|---|---|---|
| fnd.: | C 39.36 | H 3.48 | N 4.11 | F 36.47 | c) L-Glutamic acid 5-benzyl ester N-(2-{2-[2-(2-methoxyethoxy)ethoxy]ethoxy}acetyl)-1-[(1H,1H, 2H,2H,4H,4H,-3,6,9,12-tetraoxaperfluorotridecyl) methyl]amide 3.58 g (17.33 mmol) of dicyclohexylcarbodiimide are added at 0° C. to a solution of 8.5 g (12.60 mmol) of the title compound from Example 16b and 3.07 g (13.86 mmol) of {2-[2-(2-methoxyethoxy)ethoxy]ethoxy}acetic acid (Voegtle et al., Liebigs Ann. Chem., 1980, 858-862) and 1.60 g (13.86 mmol) of N-hydroxysuccinimide in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 9.2 g (83% of theory) of a colourless viscous oil.
Elemental analysis:

| calc.: | C 42.38 | H 4.47 | N 3.19 | F 28.11 |
|---|---|---|---|---|
| fnd.: | C 42.59 | H 4.51 | N 3.14 | F 28.00 | d) L-Glutamic acid N-(2-{2-[2-(2-methoxyethoxy) ethoxy]ethoxy}acetyl)-1-[(1H,1H,2H, 2H, 4H,4H,-3,6,9,12-tetraoxaperfluorotridecyl)methyl] amide 2.0 g of palladium catalyst (10% Pd/C) are added to a solution of 9.0 g (10.24 mmol) of the title compound from Example 16c in 200 ml of ethanol and the mixture is hydrogenated at room temperature for 24 h. It is filtered off from the catalyst and the filtrate is evaporated to dryness in vacuo.

Yield: 8.1 g (quantitative) of a colourless solid.
Elemental analysis:

| calc.: | C 36.56 | H 4.22 | N 3.55 | F 31.32 |
|---|---|---|---|---|
| fnd.: | C 36.78 | H 4.28 | N 3.50 | F 31.19 | e) L-Glutamic acid 5-{[1,4,7-tris(carboxylatomethyl)-1,4,7,10-tetraazacyclododecane-10-N-(2-hydroxy-3-yl]amido}-N-(2-{2-[2-(2-methoxyethoxy) ethoxy]ethoxy}acetyl)-1-[(1H,1H,2H,2H,4H,4H,-3, 6,9,12-tetraoxaperfluorotridecyl)methyl]amide, Gd complex 7.5 g (9.51 mmol) of the title compound from Example 16d, 1.09 g (9.51 mmol) of N-hydroxysuccinimide, 799 mg (19.02 mmol) of lithium chloride and 5.46 g (9.51 mmol) of 1,4,7-tris(carboxylatomethyl)-10-[3-amino-2-hydroxypropyl]-1,4,7,10-tetraazacyclododecane, Gd complex (WO 95/17451, Schering AG) are dissolved with gentle warming in 200 ml of dimethylformamide. 2.42 g (11.89 mmol) of dicyclohexyl-carbodiimide are added at 10° C. and the mixture is stirred at room temperature for 48 h. The solution is poured into 2000 ml of acetone and subsequently stirred for 10 min. The precipitated solid is filtered off and subsequently purified by chromatography (RP-18; eluent: gradient of water/acetonitrile).

Yield 8.5 g (61% of theory) of a colourless solid
Water content (Karl Fischer): 8.1%
Elemental analysis (based on the anhydrous substance):

| calc.: | C 36.64 | H 4.57 | N 7.29 | F 18.37 | Gd 11.70 |
|---|---|---|---|---|---|
| fnd.: | C 36.88 | H 4.63 | N 7.18 | F 18.22 | Gd 11.59 |

Example 17 a) N-tert-Butyloxycarbonyl-L-glutamic acid 1-[(1H, 1H,2H,2H,4H,4H,-3,6,9,12-tetraoxaperfluorotridecyl)methyl]amide 2.0 g of palladium catalyst (10% Pd/C) are added to a solution of 12.0 g (15.49 mmol) of the title compound from Example 16a in 200 ml of ethanol and the mixture is hydrogenated at room temperature for 24 h. It is filtered off from the catalyst and the filtrate is evaporated to dryness in vacuo.

Yield: 10.6 g (quantitative) of a colourless solid.
Elemental analysis:

| calc.: | C 35.10 | H 3.68 | N 4.09 | F 36.09 |
|---|---|---|---|---|
| fnd.: | C 35.39 | H 3.72 | N 4.08 | F 36.01 | b) N-tert-butyloxycarbonyl-L-glutamic acid 5-(2-{2-[2-(2-methoxyethoxy)ethoxy]-ethoxy}ethyl)amide 1-[(1H,1H,2H,2H,4H,4H,-3,6,9,12-tetraoxaperfluorotridecyl)-methyl]amide 3.77 g (18.26 mmol) of dicyclohexylcarbodiimide are added at 0° C. to a solution of 10.0 g (14.61 mmol) of the title compound from Example 17a and 3.03 g (14.61 mmol) of (2-{2-[2-(2-methoxyethoxy)ethoxy]ethoxy}ethyl)amine (Whitessides et al., JACS, 1994, 5057-5062) and 2.27 g (14.61 mmol) of N-hydroxysuccinimide in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 10:1).

Yield: 10.7 g (84% of theory) of a colourless viscous oil.
Elemental analysis:

| calc.: | C 39.87 | H 5.08 | N 4.81 | F 28.27 |
|---|---|---|---|---|
| fnd.: | C 40.05 | H 5.14 | N 4.74 | F 28.09 | c) L-Glutamic acid 5-(2-{2-[2-(2-methoxyethoxy) ethoxy]ethoxy}ethyl)amide 1-[(1H,1H,2H,2H,4H, 4H,-3,6,9,12-tetraoxaperfluorotridecyl)methyl]amide 25 ml of trifluoroacetic acid are added at 0° C. to a solution of 10.0 g (11.45 mmol) of the title compound from Example 17b in 50 ml of dichloromethane, and the mixture is subsequently stirred at room temperature for 4 h. It is evaporated to dryness in vacuo and the residue is chromatographed on silica gel (eluent: dichloromethane/methanol 10:1).

Yield: 8.5 g (96% of theory) of an amorphous solid.
Elemental analysis:

| calc.: | C 37.27 | H 4.69 | N 5.43 | F 31.93 |
|---|---|---|---|---|
| fnd.: | C 37.45 | H 4.68 | N 5.39 | F 31.84 | d) N-[1,4,7-Tris(carboxylatomethyl)-1,4,7,10-tetraazacyclododecane-10-N-(pentanoyl-3-aza-4-oxo-5-methyl-5-yl)]-L-glutamic acid 5-(2-{2-[2-(2-methoxyethoxy)ethoxy]-ethoxy}ethyl)amide 1-[(1H,1H,2H,2H,4H,4H,-3,6,9,12-tetraoxaperfluorotridecyl)-methyl]amide, Gd complex 8.0 g (10.34 mmol) of the title compound from Example 17c, 1.19 g (10.34 mmol) of N-hydroxysuccinimide, 869 mg (20.68 mmol) of lithium chloride and 6.51 g (10.34 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.67 g (12.93 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 9.0 g (59% of theory) of a colourless solid
Water content (Karl Fischer): 6.5%
Elemental analysis (based on the anhydrous substance):

| calc.: | C 37.28 | H 4.66 | N 8.09 | F 17.83 | Gd 11.35 |
|---|---|---|---|---|---|
| fnd.: | C 37.46 | H 4.72 | N 7.98 | F 17.71 | Gd 11.25 |

Example 18 a) L-2-Benzyloxycarbonylamino-4-aminobutyric acid[(1H,1H,2H,2H,4H,4H,-3,6,9,12-tetraoxaperfluorotridecyl)methyl]amide 24.7 g (100 mmol) of EEDQ (ethyl 2-ethoxy-1,2-dihydroquinoline-1-carboxylate) are added at 0° C. to 17.62 g (50 mmol) of L-2-benzyloxycarbonylamino-4-terbutyloxycarbonylaminobutyric acid (Bachem) and 22.76 g (50 mmol) of the title compound from Example 3c in 200 ml THF and the mixture is stirred at room temperature for 16 h. It is evaporated to dryness in vacuo, the residue is dissolved in 80 ml of dichloromethane, treated at 0° C. with 40 ml of trifluoroacetic acid, and subsequently stirred at room temperature for 4 h. It is evaporated to dryness in vacuo and the residue is chromatographed on silica gel (eluent: dichloromethane/methanol 10:1).

Yield: 25.2 g (73% of theory) of a colourless viscous oil.
Elemental analysis:

| calc.: | C 38.33 | H 3.51 | N 6.09 | F 35.82 |
|---|---|---|---|---|
| fnd.: | C 38.69 | H 3.48 | N 6.00 | F 35.64 | b) L-2-Benzyloxycarbonylamino-4-(2-{2-[2-(2-methoxyethoxy)ethoxy]ethoxy}acetyl)-aminobutyric acid[(1H,1H,2H,2H,4H,4H,-3,6,9,12-tetraoxaperfluorotridecyl)methyl]-amide 7.48 g (36.26 mmol) of dicyclohexylcarbodiimide are added at 0° C. to a solution of 20 g (29.01 mmol) of the title compound from Example 18a and 6.45 g (29.01 mmol) of {2-[2-(2-methoxyethoxy)ethoxy]ethoxy}acetic acid (Voegtle et al., *Liebigs Ann. Chem.*, 1980, 858-862) and 3.34 g (29.01 mmol) of N-hydroxysuccinimide in 200 ml of dimethylformamide, and the mixture is stirred at 0° C. for 3 h and subsequently at room temperature for 16 h. It is filtered off from the precipitated urea, the filtrate is evaporated to dryness in vacuo and the residue is chromatographed on silica gel (eluent: dichloromethane/methanol 20:1).

Yield: 20.7 g (80% of theory) of a colourless viscous oil.
Elemental analysis:

| calc.: | C 41.67 | H 4.51 | N 4.70 | F 27.64 |
|---|---|---|---|---|
| fnd.: | C 41.95 | H 4.58 | N 4.66 | F 27.39 | c) L-2-Amino-4-(2-{2-[2-(2-methoxyethoxy)ethoxy]ethoxy}acetyl)aminobutyric acid[(1H,1H,2H,2H,4H,4H,-3,6,9,12-tetraoxaperfluorotridecyl)methyl]amide 2.0 g of palladium catalyst (10% Pd/C) are added to a solution of 20.0 g (22.38 mmol) of the title compound from Example 18b in 200 ml of ethanol and the mixture is hydrogenated at room temperature for 24 h. It is filtered off from the catalyst and the filtrate is evaporated to dryness in vacuo.

Yield: 17.1 g (quantitative) of a colourless solid.
Elemental analysis:

| calc.: | C 36.37 | H 4.51 | N 5.53 | F 32.52 |
|---|---|---|---|---|
| fnd.: | C 36.87 | H 4.69 | N 5.36 | F 32.18 | d) L-2-[1,4,7-Tris(carboxylatomethyl)-1,4,7,10-tetraazacyclododecane-10-N-(pentanoyl-3-aza-4-oxo-5-methyl-5-yl)]-amino-4-(2-{2-[2-(2-methoxyethoxy)ethoxy]-ethoxy}acetyl)aminobutyric acid [(1H,1H,2H,2H,4H,4H,-3,6,9,12-tetraoxaperfluorotridecyl)methyl]amide, Gd complex 15.0 g (19.75 mmol) of the title compound from Example 18c, 2.27 g (19.75 mmol) of N-hydroxysuccinimide, 1.68 g (39.50 mmol) of lithium chloride and 12.43 g (19.75 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 5.09 g (24.69 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 23.4 g (59% of theory) of a colourless solid
Water content (Karl Fischer): 6.5%

Example 19 a) 2-N-[1,4,7-Tris(carboxylatomethyl)-1,4,7,10-tetraazacyclododecane-10-N-(pentanoyl-3-aza-4-oxo-5-methyl-5-yl)]-6-N-benzyloxycarbonyl-L-lysine[N-methyl-(1H,1H,2H,2H,4H,4H,-3,6,9,12-tetraoxaperfluorohexadecyl)]amide, Gd complex 50.0 g (57.64 mmol) of the title compound from Example 1e, 6.63 g (57.64 mmol) of N-hydroxysuccinimide, 4.88 g (115.28 mmol) of lithium chloride and 36.30 g (57.64 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 400 ml of dimethyl sulphoxide. 14.87 g (72.05 mmol) of dicyclohexylcarbodiimide are added at 10° C. and the mixture is stirred at room temperature for 16 h. The solution is poured into 5000 ml of diethyl ether and subsequently stirred for 10 min. The precipitated solid is filtered off and subsequently residue chromatographed on silica gel (eluent: dichloromethane/methanol/aq. ammonia 10:5:1).

Yield 57.4 g (64% of theory) of a colourless solid
Water content (Karl Fischer): 4.8%
Elemental analysis (based on the anhydrous substance):

| calc.: | C 37.35 | H 3.82 | N 7.58 | F 24.40 | Gd 10.63 |
|---|---|---|---|---|---|
| fnd.: | C 37.59 | H 3.75 | N 7.44 | F 24.22 | Gd 10.59 | b) 2-N-[1,4,7-Tris(carboxylatomethyl)-1,4,7,10-tetraazacyclododecane-10-N-(pentanoyl-3-aza-4-oxo-5-methyl-5-yl)]-L-lysine[N-methyl-(1H,1H,2H,2H,4H,4H,-3,6,9,12-tetraoxaperfluorohexadecyl)]amide, Gd complex 5.0 g of palladium catalyst (10% Pd/C) are added to a solution of 55 g (35.4 mmol) of the title compound from Example 19a in 600 ml of methanol and 100 ml of water and the mixture is hydrogenated at room temperature for 24 h. It is filtered off from the catalyst and the filtrate is evaporated to dryness in vacuo.

Yield: 50.7 g (quantitative) of a colourless solid.
Water content (Karl Fischer): 6.0%
Elemental analysis (based on the anhydrous substance):

| calc.: | C 33.93 | H 3.75 | N 8.33 | F 26.84 | Gd 11.69 |
|---|---|---|---|---|---|
| fnd.: | C 34.12 | H 3.70 | N 8.22 | F 26.69 | Gd 11.52 | c) 2-N-[1,4,7-Tris(carboxylatomethyl)-1,4,7,10-tetraazacyclododecane-10-N-(pentanoyl-3-aza-4-oxo-5-methyl-5-yl)]-6-N-(1-O-α-d-carbonylmethylmannopyranose)-L-lysine[N-methyl-(1H,1H,2H,2H,4H,4H,-3,6,9,12-tetraoxaperfluorohexadecyl)]amide, Gd complex 1.80 g (8.74 mmol) of dicyclohexylcarbodiimide are added at 0° C. to a solution of 10.0 g (6.99 mmol) of the title compound from Example 19b and 4.19 g (6.99 mmol) of 1-O-α-d-carbonylmethyl-(2,3,4,6-tetra-O-benzyl)mannopyranose (prepared according to WO 99/01160 A1) and 806 mg (6.99 mmol) of N-hydroxysuccinimide in 100 ml of dimethylformamide, and the mixture is stirred at 0° C. for 3 h and subsequently at room temperature for 16 h. It is filtered off from the precipitated urea and the filtrate is evaporated to dryness in vacuo. The residue is dissolved in 100 ml of methanol, treated with 2.0 g of palladium catalyst (10% Pd/C) and hydrogenated at room temperature for 24 h. It is filtered off from the catalyst and the filtrate is evaporated to dryness in vacuo. The residue is taken up in a little water, filtered off from insoluble constituents, and the filtrate is subsequently purified by chromatography (RP-18; eluent: gradient of water/acetonitrile).

Yield 7.5 g (64% of theory) of a colourless solid
Water content (Karl Fischer): 6.2%
Elemental analysis (based on the anhydrous substance):

| calc.: | C 35.91 | H 4.15 | N 7.44 | F 23.98 | Gd 10.45 |
|---|---|---|---|---|---|
| fnd.: | C 36.12 | H 4.11 | N 7.38 | F 23.81 | Gd 10.36 |

Example 20 a) 2-N-[1,4,7-Tris(carboxylatomethyl)-1,4,7,10-tetraazacyclododecane-10-N-(pentanoyl-3-aza-4-oxo-5-methyl-5-yl)]-6-N-{2-[2-(2-methoxyethoxy)ethoxy]acetyl}-L-lysine[N-methyl-(1H,1H,2H,2H,4H,4H,-3,6,9,12-tetraoxaperfluorohexadecyl)]-amide, Gd complex 2.84 g (13.75 mmol) of dicyclohexylcarbodiimide are added at 0° C. to a solution of 14.31 g (10.0 mmol) of the title compound from Example 19b and 1.96 g (11.0 mmol) of [2-(2-methoxyethoxy)ethoxy]acetic acid (Aldrich) and 1.27 g (11.0 mmol) of N-hydroxysuccinimide in 100 ml of dimethylformamide, and the mixture is stirred at 0° C. for 3 h and subsequently at room temperature for 16 h. It is filtered off from the precipitated urea and the filtrate is evaporated to dryness in vacuo. The residue is taken up in a little water, filtered off from the insoluble constituents, and the filtrate is subsequently purified by chromatography (RP-18; eluent: gradient of water/acetonitrile).

Yield 12.4 g (77% of theory) of a colourless solid
Water content (Karl Fischer): 6.7%
Elemental analysis (based on the anhydrous substance):

| calc.: | C 35.91 | H 4.15 | N 7.44 | F 23.98 | Gd 10.45 |
|---|---|---|---|---|---|
| fnd.: | C 36.22 | H 4.07 | N 7.36 | F 23.81 | Gd 10.22 |

Example 21 a) (2H,2H,4H,4H,-3,6,9,12-Tetraoxaperfluorohexadecanoic acid)N-[2-(2-methoxy-ethoxy)ethyl]amide 2.55 g (20 mmol) of oxalyl chloride are added to 10 g (16.5 mmol) of the title compound from Example 1a in 100 ml of dichloromethane and the mixture is stirred at room temperature for 14 h. It is evaporated to dryness in vacuo, the residue is dissolved in 100 ml of dichloromethane, 3.93 g (33 mmol) of 2-(methoxyethoxy)ethylamine (Whitesides et al., *JACS*,

---

Elemental analysis (based on the anhydrous substance):

| calc.: | C 36.79 | H 4.56 | N 8.17 | F 18.01 | Gd 11.47 |
|---|---|---|---|---|---|
| fnd.: | C 36.94 | H 4.48 | N 8.12 | F 17.89 | Gd 11.32 |

1994, 5057-5062) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 11.2 g (96% of theory) of a colourless wax

Elemental analysis:

| calc.: | C 28.87 | H 2.28 | N 1.98 | F 51.04 |
|---|---|---|---|---|
| fnd.: | C 29.04 | H 2.32 | N 2.00 | F 50.78 | b) N-[2-(2-Methoxyethoxy)ethyl]-(1H,1H,2H,2H,4H,4H,-3,6,9,12-tetraoxaperfluorohexadecyl)amine 10.5 g (14.85 mmol) of the title compound from Example 21a in 50 ml of THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. It is evaporated to dryness in vacuo, and the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.4 g (82% of theory) of a colourless oil

Elemental analysis:

| calc.: | C 29.45 | H 2.62 | N 2.02 | F 52.06 |
|---|---|---|---|---|
| fnd.: | C 29.66 | H 2.58 | N 1.98 | F 51.86 | c) 1,4,7-Tris(carboxylatomethyl)-10-{(3-aza-4-oxo-5-methyl-5-yl)-acid-N-(1H,1H,2H,2H,4H,4H,-3,6,9,12-tetraoxaperfluorohexadecyl)-N-[2-(2-methoxyethoxy)ethyl]amide}-1,4,7,10-tetraazacyclododecane, Gd complex 8 g (11.54 mmol) of the title compound from Example 21b, 1.33 g (11.54 mmol) of N-hydroxysuccinimide, 974 mg (23.08 mmol) of lithium chloride and 7.26 g (11.54 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.98 g (14.43 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 8.4 g (52% of theory) of a colourless solid

Water content (Karl Fischer): 6.8%

Elemental analysis (based on the anhydrous substance):

| calc.: | C 33.13 | H 3.55 | N 6.44 | F 27.66 | Gd 12.05 |
|---|---|---|---|---|---|
| fnd.: | C 33.41 | H 3.58 | N 6.39 | F 27.50 | Gd 11.95 |

Example 22 a) (2H,2H,4H,4H,-3,6,9,12-Tetraoxaperfluorohexadecanoic acid)N-{2-[2-(2-methoxy-ethoxy)ethoxy]ethyl}amide 2.55 g (20 mmol) of oxalyl chloride are added to 10 g (16.5 mmol) of the title compound from Example 1a in 100 ml of dichloromethane and the mixture is stirred at room temperature for 14 h. It is evaporated to dryness in vacuo, the residue is dissolved in 100 ml of dichloromethane, 5.39 g (33 mmol) of 2-[2-(methoxyethoxy)ethoxy]ethyl-amine (Whitesides et al., JACS, 1994, 5057-5062) are added and the mixture is subsequently stirred at room temperature for 4 h. The reaction solution is treated with 100 ml of 1 N hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:1).

Yield: 11.4 g (92% of theory) of a colourless wax

Elemental analysis:

| calc.: | C 30.37 | H 2.68 | N 1.86 | F 48.04 |
|---|---|---|---|---|
| fnd.: | C 30.52 | H 2.65 | N 1.84 | F 57.89 | b) N-{2-[2-(2-Methoxyethoxy)ethoxy]ethyl}-(1H,1H,2H,2H,4H,4H,-3,6,9,12-tetraoxaperfluorohexadecyl)amine 10.0 g (13.31 mmol) of the title compound from Example 22a in 50 ml of THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. It is evaporated to dryness in vacuo, the residue is taken up in 100 ml of 5% strength sodium hydroxide solution and extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 8.6 g (88% of theory) of a colourless oil

Elemental analysis:

| calc.: | C 30.95 | H 3.01 | N 1.90 | F 48.95 |
|---|---|---|---|---|
| fnd.: | C 30.68 | H 2.97 | N 1.87 | F 48.67 | c) 1,4,7-Tris(carboxylatomethyl)-10-[(3-aza-4-oxo-5-methyl-5-yl)acid N-(1H,1H,2H,2H,4H,4H,-3,6,9,12-tetraoxaperfluorohexadecyl)-N-{2-[2-(2-methoxyethoxy)ethoxy]-ethyl}amide]1,4,7,10-tetraazacyclododecane, Gd complex 8 g (10.43 mmol) of the title compound from Example 22b, 1.20 g (10.43 mmol) of N-hydroxysuccinimide, 880 mg (20.86 mmol) of lithium chloride and 6.56 g (10.43 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.69 g (13.04 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 8.4 g (56% of theory) of a colourless solid
Water content (Karl Fischer): 6.5%
Elemental analysis (based on the anhydrous substance):

| calc.: | C 33.83 | H 3.74 | N 6.23 | F 26.76 | Gd 11.66 |
|---|---|---|---|---|---|
| fnd.: | C 34.03 | H 3.71 | N 6.14 | F 26.59 | Gd 11.49 |

Example 23 a) [1-O-α-d-(2,3,4,6-Tetra-O-benzyl)mannopyranosyl]acetamide 11.45 g (90 mmol) of oxalyl chloride are added to 40 g (66.81 mmol) of 1-O-α-d-carbonylmethyl-(2,3,4,6-tetra-O-benzyl)mannopyranose (prepared according to WO 99/01160 A1) in 300 ml of dichloromethane and the mixture is stirred at room temperature for 14 h. It is evaporated to dryness in vacuo, the residue is dissolved in 400 ml dichloromethane, ammonia gas is passed into the solution at 0° C. for about 2 h and the mixture is subsequently stirred at room temperature for 4 h. The reaction solution is treated with 400 ml of 1 N of hydrochloric acid, and thoroughly stirred for 15 min. The organic phase is separated off, dried over magnesium sulphate and evaporated to dryness in vacuo. The residue is chromatographed on silica gel (eluent: ethyl acetate/hexane 1:2).

Yield: 34.1 g (85% of theory) of a colourless oil
Elemental analysis:

| calc.: | C 72.34 | H 6.58 | N 2.34 |
|---|---|---|---|
| fnd.: | C 72.69 | H 6.54 | N 2.39 | b) 2-[1-O-α-d-(2,3,4,6-Tetra-O-benzyl)mannopyranosyl]ethylamine 33 g (55.21 mmol) of the title compound from Example 23a in 100 ml of THF are treated with 30 ml of 10 M boranedimethyl sulphide (in THF) and heated under reflux for 5 h. The mixture is cooled to 0° C., 100 ml of methanol are added dropwise, and it is stirred at room temperature for 1 h and subsequently evaporated to dryness in vacuo. The residue is taken up in a mixture of 200 ml of ethanol/100 ml of ethanolamine and stirred at 60° C. for 14 h. It is evaporated to dryness in vacuo, the residue is taken up in 300 ml of 5% strength sodium hydroxide solution and extracted three times with 300 ml each of dichloromethane. The combined organic phases are dried over magnesium sulphate, evaporated to dryness in vacuo and the residue is chromatographed on silica gel (eluent: dichloromethane/methanol 10:1).

Yield: 26.2 g (81% of theory) of a colourless solid
Elemental analysis:

| calc.: | C 74.08 | H 7.08 | N 2.40 |
|---|---|---|---|
| fnd.: | C 74.55 | H 7.19 | N 2.31 | c) (2H,2H,4H,4H,-3,6,9,12-Tetraoxaperfluorohexadecanoic acid)N-{2-[1-O-α-d-(2,3,4,6-tetra-O-benzyl)mannopyranosyl]ethyl}amide 4.93 g (23.90 mmol) of dicyclohexylcarbodiimide are added at 0° C. to a solution of 11.16 g (19.12 mmol) of the title compound from Example 23b and 11.59 g (19.12 mmol) of the title compound from Example 1a and 2.2 g (19.12 mmol) of N-hydroxysuccinimide in 200 ml of dimethylformamide, and the mixture is stirred at 0° C. for 3 h and subsequently at room temperature for 16 h. It is filtered off from precipitated urea, the filtrate is evaporated to dryness in vacuo and the residue is chromatographed on silica gel (eluent: dichloromethane/methanol 20:1).

Yield: 15.7 g (71% of theory) of a colourless viscous oil.
Elemental analysis:

| calc.: | C 49.20 | H 3.78 | N 1.20 | F 30.80 |
|---|---|---|---|---|
| fnd.: | C 49.44 | H 3.69 | N 1.18 | F 30.59 | d) N-{2-[1-O-α-d-(2,3,4,6-Tetra-O-benzyl)mannopyranosyl]ethyl}-(1H,1H,2H,2H,4H,4H,-3,6,9,12-tetraoxaperfluorohexadecyl)amine 15.0 g (12.80 mmol) of the title compound from Example 23c in 50 ml of THF are treated with 15 ml of 10 M boranedimethyl sulphide (in THF) and heated under reflux for 5 h. The mixture is cooled to 0° C., 20 ml of methanol are added dropwise, and it is stirred at room temperature for 1 h and subsequently evaporated to dryness in vacuo. The residue is taken up in a mixture of 100 ml of ethanol/50 ml of 1 M hydrochloric acid and stirred at 40° C. for 14 h. It is evaporated to dryness in vacuo, the residue is taken up in 100 ml of 5% strength sodium hydroxide solution and the mixture is extracted three times with 100 ml each of dichloromethane. The combined organic phases are dried over magnesium sulphate, evaporated to dryness in vacuo and the residue is chromatographed on silica gel (eluent: dichloromethane/methanol 10:1).

Yield: 12.2 g (82% of theory) of a colourless oil
Elemental analysis:

| calc.: | C 49.79 | H 4.00 | N 1.21 | F 31.18 |
|---|---|---|---|---|
| fnd.: | C 49.88 | H 4.13 | N 1.18 | F 31.04 | e) N-[2-(1-O-α-d-Mannopyranosyl)ethyl]-(1H,1H, 2H,2H,4H,4H,-3,6,9,12-tetraoxaperfluorohexadecyl) amine 2.0 g of palladium catalyst (10% Pd/C) are added to a solution of 11.5 g (9.93 mmol) of the title compound from Example 23d in 200 ml of ethanol and the mixture is hydrogenated at room temperature for 24 h. It is filtered off from the catalyst and the filtrate is evaporated to dryness in vacuo.
Yield: 7.90 g (quantitative) of a colourless solid.
Elemental analysis:

| calc.: | C 30.13 | H 2.78 | N 1.76 | F 45.27 |
|---|---|---|---|---|
| fnd.: | C 30.59 | H 2.92 | N 1.67 | F 44.89 | f) 1,4,7-Tris(carboxylatomethyl)-10-{[(3-aza-4-oxo-5-methyl-5-yl)acid N-(1H,1H,2H,2H,4H,4H,-3,6,9,12-tetraoxaperfluorohexadecyl)-N-[2-(1-O-α-d-mannopyranosyl)-ethyl]amide}1,4,7,10-tetraazacyclododecane, Gd complex 7 g (8.78 mmol) of the title compound from Example 23e, 1.01 g (8.78 mmol) of N-hydroxysuccinimide, 741 mg (17.56 mmol) of lithium chloride and 5.52 g (8.78 mmol) of 1,4,7-tris(carboxylatomethyl)-10-[1-carboxy-3-aza-4-oxo-5-methylpentan-5-yl]-1,4,7,10-tetraazacyclododecane, Gd complex (WO 98/24775, Schering AG, (Example 1)) are dissolved with gentle warming in 200 ml of dimethyl sulphoxide. 2.26 g (10.98 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).
Yield 7.7 g (58% of theory) of a colourless solid
Water content (Karl Fischer): 6.9%
Elemental analysis (based on the anhydrous substance):

| calc.: | C 33.24 | H 3.58 | N 5.96 | F 25.62 | Gd 11.16 |
|---|---|---|---|---|---|
| fnd.: | C 33.45 | H 3.55 | N 5.89 | F 25.57 | Gd 11.05 |

Example 24 a) 10-(5-Oxotetrahydrofuran-2-ylmethyl)-1,4,7-tris(carboxymethyl)-1,4,7,10-tetraazacyclododecane 8.3 g (207.6 mmol) of sodium hydroxide are added to 12.0 g (34.6 mmol) of 1,4,7-tris-(carboxymethyl)-1,4,7,10-tetraazacyclododecane (DO3A) in 50 ml of water. For this, a solution of 5.02 g (43.25 mmol) of 3-oxiranylpropionic acid (Dakoji et al., *J. Am. Chem. Soc.*, 1996, 10971-10979) is added dropwise to 50 ml of n-butanol/50 ml of 2-propanol and the solution is heated to 80° C. for 24 h. The reaction solution is evaporated to dryness in vacuo, and the residue is treated with 300 ml of water and adjusted to pH 3 with 3 N hydrochloric acid. Subsequently, the mixture is extracted three times with 200 ml each of n-butanol, the combined butanol phases are evaporated to dryness in vacuo and the residue is purified by chromatography (RP-18; eluent: gradient of water/acetonitrile).
Yield 13.6 g (79% of theory) of a colourless solid
Water content (Karl Fischer): 10.4%

Elemental analysis (based on the anhydrous substance):

| calc.: | C 51.34 | H 7.26 | N 12.60 |
|---|---|---|---|
| fnd.: | C 51.63 | H 7.05 | N 12.44 | b) 10-(5-Oxotetrahydrofuran-2-ylmethyl)-1,4,7-tris(carboxymethyl)-1,4,7,10-tetraazacyclododecane, Gd complex 12.0 g (24.2 mmol) of the title compound from Example 23a are dissolved in 100 ml of water and 1 ml of acetic acid, treated with 4.39 g (12.1 mmol) of gadolinium oxide and stirred at 80° C. for 6 h. The solution is filtered, evaporated to dryness and subsequently purified by chromatography (RP-18; eluent: gradient of water/acetonitrile).
Yield 13.8 g (89% of theory) of a colourless solid
Water content (Karl Fischer): 6.5%
Elemental analysis (based on the anhydrous substance):

| calc.: | C 38.12 | H 4.88 | N 9.36 | Gd 26.26 |
|---|---|---|---|---|
| fnd.: | C 38.26 | H 4.89 | N 9.21 | Gd 26.09 | c) 1,4,7-Tris(carboxylatomethyl)-10-[(4-hydroxy-5-yl)acid N-(1H,1H,2H,2H,4H,4H,-3,6,9,12-tetraoxaperfluorohexadecyl)-N-(2-methoxyethyl)amide]1,4,7,10-tetraazacyclododecane, Gd complex 2.5 g (3.85 mmol) of the title compound from Example 2b and 3.70 g (5.78 mmol) of the title compound from Example 23b are dissolved in 50 ml of methanol and the mixture is stirred at a temperature of 50° C. for 48 h. It is evaporated to dryness and subsequently purified by chromatography (RP-18; eluent: gradient of water/acetonitrile).
Yield 3.89 g (75% of theory) of a colourless solid
Water content (Karl Fischer): 7.2%
Elemental analysis (based on the anhydrous substance):

| calc.: | C 32.72 | H 3.47 | N 5.61 | F 28.92 | Gd 12.60 |
|---|---|---|---|---|---|
| fnd.: | C 32.98 | H 3.44 | N 5.49 | F 28.77 | Gd 12.45 |

Example 25 a) 1,4,7-Tris(carboxylatomethyl)-10-[(4-(R)-carboxylato-4-yl)acid N-(1H,1H,2H,2H,-4H,4H,-3,6,9,12-tetraoxaperfluorohexadecyl)-N-(2-methoxyethyl)amide]1,4,7,10-tetraazacyclododecane, Gd complex monosodium salt and 1,4,7-tris(carboxylato-methyl)-10-{[(R)-(2-carboxylatoethyl)yl]acid N-(1H,1H,2H,2H,4H,4H,-3,6,9,12-tetraoxaperfluorohexadecyl)-N-(2-methoxyethyl)amide}1,4,7,10-tetraazacyclododecane, Gd complex monosodium salt 2.5 g (3.85 mmol) of the title compound from Example 2b, 493 mg (4.82 mmol) of triethylamine and 3.84 g (4.82 mmol) of monopentafluoroophenyl 2-(R)-2-[4,7,10-tris(carboxylatomethyl)-1,4,7,10-tetraazacyclododecane-1-yl]pentanedicarboxylate, Gd complex (WO 2005/0014154, EPIX PHARMACEUTICALS, INC., (Example 9: EP-2104-15-Pfp)) are dissolved in 50 ml of dimethyl sulphoxide and stirred at room temperature for 16 h. The solution is poured into 1000 ml of acetone and subsequently stirred for 10 min. The precipitated solid is filtered off and subsequently purified by chromatography (RP-18; eluent: gradient of water/acetonitrile). The fractions comprising the product are evaporated, dissolved in water, neutralized with 0.1 N sodium hydroxide solution and subsequently lyophilized Yield: 2.01 g (37% of theory) of a colourless solid as a 3:2 regeoismer mixture.
Water content (Karl Fischer): 8.5%
Elemental analysis (based on the anhydrous substance):

| calc.: | C 31.81 | H 3.14 | N 5.45 | F 28.11 | Gd 12.25 |
|---|---|---|---|---|---|
| fnd.: | C 32.04 | H 3.11 | N 5.39 | F 28.02 | Gd 12.16 |

Example 26 a) 1,4,7-Tris(tert-butoxycarboxylatomethyl)-10-[(3-aza-4-oxo-5-methyl-5-yl)acid N-(1H,1H,2H,2H,4H,4H,-3,6,9,12-tetraoxaperfluorohexadecyl)-N-(2-methoxyethyl)amide]1,4,7,10-tetraazacyclododecane, sodium bromide complex 20 g (30.80 mmol) of the title compound from Example 2b, 1.42 g (12.32 mmol) of N-hydroxysuccinimide and 23.0 g (30.80 mmol) of 1,4,7-tris(tert-butoxycarboxylatomethyl)-10-[1-carboxy-3-aza-4-oxo-5-methylpentan-5-yl]-1,4,7,10-tetraazacyclododecane, sodium bromide complex (WO 98/24775, Schering AG, (Example 1d)) are dissolved with gentle warming in 400 ml of dimethylformamide. 3.18 g (15.4 mmol) of dicyclohexylcarbodiimide are added at 10° C. and the mixture is stirred at room temperature for 16 h. It is filtered off from the precipitated urea, the filtrate is evaporated to dryness in vacuo and the residue is chromatographed on silica gel (eluent: dichloromethane/methanol 20:1).
Yield 27.7 g (65% of theory) of a colourless solid
Elemental analysis:

| calc.: | C 40.10 | H 5.05 | N 6.10 | F 26.20 |
|---|---|---|---|---|
| fnd.: | C 40.84 | H 5.26 | N 5.88 | F 25.87 | b) 1,4,7-Tris(carboxymethyl)-10-[(3-aza-4-oxo-5-methyl-5-yl)acid N-(1H,1H,2H,2H,-4H,4H,-3,6,9,12-tetraoxaperfluorohexadecyl)-N-(2-methoxyethyl)amide]1,4,7,10-tetraazacyclododecane 25 g (18.14 mmol) of the title compound from Example 25a are dissolved in 150 ml of trifluoroacetic acid and stirred at room temperature for 5 h. The mixture is evaporated to dryness, taken up in water and subsequently purified by chromatography (RP-18; eluent: gradient of water/acetonitrile).
Yield 17.1 g (81% of theory) of a colourless solid
Water content (Karl Fischer): 4.7%
Elemental analysis (based on the anhydrous substance):

| calc.: | C 36.90 | H 4.10 | N 7.59 | F 32.62 |
|---|---|---|---|---|
| fnd.: | C 37.21 | H 4.12 | N 7.46 | F 32.48 |

Example 27 a) 1,4,7-Tris(carboxylatomethyl)-10-[(3-aza-4-oxo-5-methyl-5-yl)acid N-(1H,1H,2H,2H,4H,4H,-3,6,9,12-tetraoxaperfluorohexadecyl)-N-(2-methoxyethyl)amide]1,4,7,10-tetraazacyclododecane, Y complex 2.0 g (1.81 mmol) of the title compound from Example 25a are dissolved in 50 ml of water and 1 ml of acetic acid, treated with 387 mg (1.99 mmol) of yttrium chloride and stirred at 80° C. for 6 h. The mixture is neutralized with ammonia, evaporated to dryness and subsequently purified by chromatography (RP-18; eluent: gradient of water/acetonitrile).
Yield 1.92 g (84% of theory) of a colourless solid
Water content (Karl Fischer): 5.5%
Elemental analysis (based on the anhydrous substance):

| calc.: | C 34.24 | H 3.55 | N 7.05 | F 30.27 | Y 7.45 |
|---|---|---|---|---|---|
| fnd.: | C 34.55 | H 3.61 | N 6.87 | F 30.11 | Y 7.31 |

Example 28 a) 1,4,7-Tris(carboxylatomethyl)-10-[(3-aza-4-oxo-5-methyl-5-yl)acid N-(1H,1H,2H,2H,4H,4H,-3,6,9,12-tetraoxaperfluorohexadecyl)-N-(2-methoxyethyl)amide]-1,4,7,10-tetraazacyclododecane, Dy complex 2.0 g (1.81 mmol) of the title compound from Example 25a are dissolved in 50 ml of water and 1 ml of acetic acid, treated with 534 mg (1.99 mmol) of dysprosium chloride and stirred at 80° C. for 6 h. The mixture is neutralized with ammonia, evaporated to dryness and subsequently purified by chromatography (RP-18; eluent: gradient of water/acetonitrile).
Yield 2.14 g (87% of theory) of a colourless solid
Water content (Karl Fischer): 6.1%
Elemental analysis (based on the anhydrous substance):

| calc.: | C 32.25 | H 3.34 | N 6.64 | F 28.51 | Dy 12.83 |
|---|---|---|---|---|---|
| fnd.: | C 32.48 | H 3.41 | N 6.44 | F 28.32 | Dy 12.69 |

Example 29 a) 1,4,7-Tris(carboxylatomethyl)-10-[(3-aza-4-oxo-5-methyl-5-yl)acid N-(1H,1H,2H,2H,4H,4H,-3,6,9,12-tetraoxaperfluorohexadecyl)-N-(2-methoxyethyl)amide]1,4,7,10-tetraazacyclododecane, Yb complex 2.0 g (1.81 mmol) of the title compound from Example 25a are dissolved in 50 ml of water and 1 ml of acetic acid, treated with 555 mg (1.99 mmol) of ytterbium chloride and stirred at 80° C. for 6 h. The mixture is neutralized with ammonia, evaporated to dryness and subsequently purified by chromatography (RP-18; eluent: gradient of water/acetonitrile).
Yield 2.10 g (84% of theory) of a colourless solid
Water content (Karl Fischer): 6.7%
Elemental analysis (based on the anhydrous substance):

| calc.: | C 31.99 | H 3.32 | N 6.58 | F 28.27 | Yb 13.55 |
|---|---|---|---|---|---|
| fnd.: | C 32.28 | H 3.24 | N 6.49 | F 28.07 | Yb 13.41 |

Example 30 a) Benzyl 4-benzyloxycarbonylamino-5-[bis(2-benzyloxycarbonylaminoethyl)amino]-pentanecarboxylate 17.87 g (50 mmol) of Z-Glu-(OBn)-OH (Bachem) are dissolved in 200 ml of methylene chloride and a solution of 15.5 g (55 mmol) of trifluoromethanesulphonic anhydride (Aldrich) and 6.97 g (65 mmol) of 2,6-dimethylpyridine (Aldrich) in 100 ml of methylene chloride is added dropwise at −78° C. in the course of 30 min and the mixture is stirred at at 0° C. for 3 h. The reaction mixture is extracted twice with 100 ml each of ice water and the organic phase is dried using sodium sulphate. The crude product is then added dropwise at −20° C. to a solution of 18.57 g (50 mmol) of N,N''-di-Z-diethylenetriamine (Fluka) and 12.9 g (100 mmol) of ethyldiisopropylamine in 200 ml of methylene chloride and the mixture is stirred at −20° C. for 6 h. Subsequently, it is stirred at room temperature for a further 24 h. The reaction mixture is extracted twice with 150 ml of water, and the organic phase is dried using sodium sulphate, evaporated to dryness and chromatographed on silica gel (hexane/ethyl acetate 5:1). The fractions comprising the product are combined and evaporated.

Elemental analysis:

| calc.: | C 67.21 | H 6.52 | N 7.88 |
|---|---|---|---|
| fnd.: | C 67.44 | H 6.49 | N 7.88 | b) 4-Amino-5-[bis(2-aminoethyl)amino]pentanecarboxylic acid 14.2 g (20 mmol) of benzyl 4-benzyloxycarbonylamino-5-[bis(2-benzyloxycarbonyl-aminoethyl)amino]pentanecarboxylate are dissolved in 300 ml of isopropanol, treated with 30 ml of water and 3 g of palladium catalyst (10% Pd/C) are added. The mixture is hydrogenated at 50° C. for 8 hours. It is filtered off from the catalyst and the filtrate is evaporated to dryness in vacuo.

Yield: 4.35 g (quantitative) of a colourless powder
Elemental analysis:

| calc.: | C 49.52 | H 10.16 | N 25.67 |
|---|---|---|---|
| fnd.: | C 49.67 | H 10.18 | N 25.57 | c) 1-(Sodium sulphonatobutyl)-4-carboxy-3-benzyloxy-6-methyl-1[H]-pyridin-2-one 4.31 g (15 mmol) of 4-ethoxycarbonyl-3-benzyloxy-6-methyl-1[H]-pyridin-2-one (International Patent Application WO 03/016923, Example 2) in 15 ml of DMF are treated with 0.41 g (17 mmol) of lithium hydroxide and, after addition of 2.04 g (15 mmol) of 1,4-butane sultone, stirred overnight at room temperature. Subsequently, the solvent is distilled off, the residue is treated with 50 ml of 2 N sodium hydroxide solution and the mixture is stirred at room temperature for 6 hours. The solution is adjusted to pH 3 by addition of AMBERLITE® IR-120 (H⁺) ion exchanger and freeze-dried. The lyophilizate is chromatographed on an RP-18 Lichroprep column (eluent: water). The fractions comprising the product are combined and evaporated to dryness.

Elemental analysis:

| calc.: | C 51.79 | H 4.83 | N 3.36 | Na 5.51 | S 7.68 |
|---|---|---|---|---|---|
| fnd.: | C 51.53 | H 4.97 | N 3.12 | Na 5.11 | S 7.29 | d) 1-(Sodium sulphonatobutyl)-4-(4-nitrophenyloxycarbonyl)-3-benzyloxy-6-methyl-1[H]-pyridin-2-one 2.09 g (5 mmol) of the title compound from Example 30c and 765 mg (5.5 mmol) of nitrophenol are dissolved in 30 ml of DMF, treated with 1 ml of ethyldiisopropylamine and 1.77 g (5.5 mmol) of O-(benzotriazol-1-yl)-N,N,N',N'-tetramethyluronium tetrafluoroborate and stirred overnight at room temperature. The reaction mixture is evaporated to dryness and chromatographed on silica gel (isopropanol). The fractions comprising the product are combined and evaporated.

Elemental analysis:

| calc.: | C 53.53 | H 4.31 | N 5.20 | Na 4.27 | S 5.95 |
|---|---|---|---|---|---|
| fnd.: | C 53.42 | H 4.55 | N 5.03 | Na 4.02 | S 6.20 | e) 5-[Bis-(2-{[1-(sodium sulphonatobutyl)-3-benzyloxy-6-methyl-2-oxo-1,2-dihydro-pyridine-4-carbonyl]amino}ethyl)amino]-4-{[1-(sodium sulphonatobutyl)-3-benzyloxy-6-methyl-2-oxo-1,2-dihydropyridine-4-carbonyl]amino}pentanecarboxylic acid 2.15 g (4 mmol) of the title compound from Example 30d and 262 mg (1.2 mmol) of 4-amino-5-[bis(2-aminoethyl)amino]pentanecarboxylic acid (Example 30b) are dissolved in 50 ml of DMF, treated with 870 ul (5 mmol) of ethyldiisopropylamine and stirred at room temperature for three days. The reaction mixture is evaporated to dryness and chromatographed on Lichroprep RP-18 (water/acetonitrile gradient). The fractions comprising the product are combined and evaporated.

Elemental analysis:

| calc.: | C 53.42 | H 5.41 | N 6.92 | Na 4.87 | S 6.79 |
|---|---|---|---|---|---|
| fnd.: | C 53.21 | H 5.67 | N 6.77 | Na 5.01 | S 6.38 | f) 5-[Bis(2-{[1-(sodium sulphonatobutyl)-3-hydroxy-6-methyl-2-oxo-1,2-dihydro-pyridine-4-carbonyl]amino}ethyl)amino]-4-{[1-(sodium sulphonatobutyl)-3-hydroxy-6-methyl-2-oxo-1,2-dihydropyridine-4-carbonyl]amino}pentanecarboxylic acid 1.0 g of palladium catalyst (10% Pd/C) is added to a solution of 1.42 g (1 mmol) of the title compound from Example 30e in 100 ml of ethanol and the mixture is hydrogenated at room temperature for 48 h. It is filtered off from the catalyst and the filtrate is evaporated to dryness in vacuo. The residue is complexed without further characterization.

g) Gadolinium complex of 5-[bis(2-{[1-(sodium sulphonatobutyl)-3-hydroxy-6-methyl-2-oxo-1,2-dihydropyridine-4-carbonyl]amino}ethyl)amino]-4-{[1-(sodium sulphonatobutyl)-3-hydroxy-6-methyl-2-oxo-1,2-dihydropyridine-4-carbonyl]amino}pentanecarboxylic acid 371 mg (1 mmol) of gadolinium chloride hexahydrate are added to 1.15 g (1 mmol) of the title compound from Example 30f in 50 ml of water at pH 8.5 (pH stat) and the mixture is stirred overnight at room temperature. The reaction mixture is evaporated to dryness and chromatographed on Lichroprep RP-18 (water/acetonitrile gradient). The fractions comprising the product are combined and evaporated.

Water content (Karl Fischer): 8.1%
Elemental analysis (based on the anhydrous substance):

| calc.: | C 38.15 | H 4.12 | Gd 11.89 | N 7.41 | Na 6.95 | S 7.27 |
| fnd.: | C 37.88 | H 4.23 | Gd 11.62 | N 7.39 | Na 7.11 | S 7.09 | h) Gadolinium complex of 5-[bis(2-{[1-(sodium sulphonatobutyl)-3-hydroxy-6-methyl-2-oxo-1,2-dihydropyridine-4-carbonyl]amino}ethyl)amino]-4-{[1-(sodium sulphonatobutyl)-3-hydroxy-6-methyl-2-oxo-1,2-dihydropyridine-4-carbonyl]amino}pentanecarboxylic acid [N-(1H,1H,2H,2H,4H,4H,-3,6,9,12-tetraoxaperfluorohexadecyl)-N-(2-methoxyethyl)]amide 1.48 g (2.28 mmol) of the title compound from Example 2b, 263 mg (2.28 mmol) of N-hydroxysuccinimide and 3.0 g (2.28 mmol) of the title compound from Example 30g are dissolved with gentle warming in 50 ml of dimethyl sulphoxide. 588 mg (2.85 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 2.15 g (46% of theory) of a colourless solid
Water content (Karl Fischer): 4.8%
Elemental analysis (based on the anhydrous substance):

| calc.: | C 35.81 | H 3.57 | Gd 8.08 | N 5.76 | Na 3.54 | S 4.94 | F 18.55 |
| fnd.: | C 36.08 | H 3.55 | Gd 8.00 | N 5.75 | Na 3.49 | S 4.87 | F 18.49 |

Example 31 a) [Bis(2-{[1-(sodium sulphonatobutyl)-3-benzyloxy-6-methyl-2-oxo-1,2-dihydro-pyridine-4-carbonyl]amino}ethyl)amino]ethylamine 6.45 g (12 mmol) of the title compound from Example 30d and 876 mg (6 mmol) of tris(2-aminoethyl)amine are dissolved in 50 ml of DMF, treated with 2.6 ml (15 mmol) of ethyldiisopropylamine and stirred at room temperature for three days. The reaction mixture is evaporated to dryness and chromatographed on Lichroprep RP-18 (water/acetonitrile gradient). The fractions comprising the product are combined and evaporated.

Elemental analysis:

| calc.: | C 44.72 | H 5.69 | N 10.79 | Na 5.90 | S 8.23 |
| fnd.: | C 44.89 | H 5.66 | N 10.81 | Na 5.32 | S 8.15 | b) 2,3-Bisbenzyloxy-N-{[bis(2-{[1-(sodium sulphonatobutyl)-3-benzyloxy-6-methyl-2-oxo-1,2-dihydropyridine-4-carbonyl]amino}ethyl)amino]ethyl}-terephthalic acid monoamide 4.4 g (5.65 mmol) of the title compound from Example 31a and 4.91 g (8.47 mmol) of (2,3-bisbenzyloxy)-1,4-(bis-2-thioxothiazolidine-3-carbonyl)benzene (Raymond et al., Inorg. Chem. (2003), (42), 4930) are dissolved in 100 ml of methylene chloride and stirred at room temperature for three days. The reaction mixture is extracted with 100 ml of 1 N sodium hydroxide solution and with 100 ml of saturated sodium chloride solution, and the organic phase is dried using sodium sulphate, evaporated to dryness and chromatographed on Lichroprep RP-18 (water/acetonitrile gradient). The fractions comprising the product are combined and evaporated.

Elemental analysis:

| calc.: | C 59.17 | H 5.50 | N 6.37 | S 4.86 |
| fnd.: | C 59.47 | H 5.39 | N 6.29 | S 4.71 | c) 2,3-Dihydroxy-N-{[bis(2-{[1-(sodium sulphonatobutyl)-3-hydroxy-6-methyl-2-oxo-1,2-dihydropyridine-4-carbonyl]amino}ethyl)amino]ethyl}terephthalic acid monoamide 1.0 g of palladium catalyst (10% Pd/C) is added to a solution of 5.2 g (3.94 mmol) of the title compound from Example 31b in 100 ml of ethanol and the mixture is hydrogenated at room temperature for 48 h. It is filtered off from the catalyst and the filtrate is evaporated to dryness in vacuo. The residue is complexed without further characterization.

d) Gadolinium complex of 2,3-dihydroxy-N-{[bis(2-{[1-(sodium sulphonatobutyl)-3-hydroxy-6-methyl-2-oxo-1,2-dihydropyridine-4-carbonyl]amino}ethyl)amino]ethyl}-terephthalic acid monoamide 1.46 g (3.94 mmol) of gadolinium chloride hexahydrate are added to 3.75 g (3.94 mmol) of the title compound from Example 31c in 100 ml of water at pH 8.5 (pH stat) and the mixture is stirred overnight at room temperature. The reaction mixture is evaporated to dryness and chromatographed on Lichroprep RP-18 (water/acetonitrile gradient). The fractions comprising the product are combined and evaporated.

Water content (Karl Fischer): 8.0%
Elemental analysis (based on the anhydrous substance):

| calc.: | C 39.15 | H 3.91 | Gd 13.85 | N 7.40 | Na 6.08 | S 5.65 |
| fnd.: | C 39.44 | H 3.88 | Gd 13.72 | N 7.28 | Na 7.22 | S 5.44 | e) 6-N-(2,3-Dihydroxy-N-{[bis(2-{[1-(sodium sulphonatobutyl)-3-hydroxy-6-methyl-2-oxo-1,2-dihydropyridine-4-carbonyl]amino}ethyl)amino]ethyl}-terephthalyl)-2-N-(1-O-α-d-carbonylmethylmannopyranose)-L-lysine[N-methyl-(1H,1H,2H,2H,4H,4H,-3,6,9,12-tetraoxaperfluorohexadecyl)]amide, Gd complex 2.10 g (2.20 mmol) of the title compound from Example 1g, 254 mg (2.28 mmol) of N-hydroxysuccinimide and 2.5 g (2.20 mmol) of the title compound from Example 30g are dissolved with gentle warming in 50 ml of dimethyl sulphoxide. 580 mg (2.79 mmol) of dicyclohexylcarbodiimide are added at 10° C. and the mixture is stirred at room temperature for 16 h. The solution is poured into 2000 ml of acetone and subsequently stirred for 10 min. The precipitated solid is filtered off and subsequently purified by chromatography (RP-18; eluent: gradient of water/acetonitrile).

Yield 3.15 g (65% of theory) of a colourless solid
Water content (Karl Fischer): 5.3%
Elemental analysis (based on the anhydrous substance):

| | | | | | | | | | | | | |
|---|---|---|---|---|---|---|---|---|---|---|---|---|
| calc.: | C 37.12 | H 3.70 | Gd 7.59 | N 6.09 | Na 3.33 | S 3.10 | F 17.43 |
| fnd.: | C 37.43 | H 3.66 | Gd 7.44 | N 5.98 | Na 3.43 | S 3.06 | F 17.36 |

Example 32

Relaxivity

The T1 and T2 relaxation times of water and plasma (bovine) having increasing concentrations of the substance from Example 2c) contained therein were determined at 40° C. using an NMR pulse spectrometer (Minispec PC 20) at 0.47 T (Table 1).

TABLE 1

Relaxivity of the substance from Example 2 c)

| Gd concentration | | Relaxivity [l/(mmol * s)] | |
|---|---|---|---|
| [mmol/l] | Matrix | R1 | R2 |
| 0.000-0.009 | water | 5.3 ± 0.4 | 5.3 ± 1.2 |
| 0.020-1.099 | water | 17.8 ± 0.1 | 16.3 ± 0.2 |
| 0.271-1.086 | plasma | 26.0 ± 0.5 | 35.1 ± 0.3 |

From the R1 relaxivities in water at high and low concentrations, a critical micelle formation concentration (CMC) of 0.02 mmol of Gd/l can be determined. The relaxivity in plasma is greater than that in water and indicates a protein bond.

Example 33

Acute Toxicity after Single Intravenous Administration in Mice

Exploratory

After intravenous administration of the substances of Examples 2c), 21 c) and 22 c) in mice (n=3; injection rate: 2 ml/min), the acute systemic tolerability ($LD_{50}$) was determined in an exploratory manner. In each case, a number of doses were investigated using an observation period of 7 days. The average acute toxicities to be expected were 2.5 mmol of Gd/kg of body weight for the substance from Example 2c) and >10.0 mmol of Gd/kg of body weight for the substances from Examples 21c) and 22 c).

Example 34

Release of Histamine after Single Intravenous Administration in Rats

After intravenous administration of the substances from Examples 2c) and 22 c) in rats (n=3), the release of histamine was determined at different points in time. For this, blood was taken from the carotid artery before and 10, 30 and 60 minutes after contrast agent administration, and the histamine contained in the plasma was determined by means of an ELISA system. The histamine values measured can be seen in Table 2. The histamine blank values in the conscious rats were in the normal range known from the literature. The compounds according to the invention induced no relevant histamine release.

TABLE 2

Plasma histamine values after administration of the substances from Example 2 c) and Example 22 c).

| | Histamine [ng/ml] | | | |
|---|---|---|---|---|
| | baseline | 10 min p.i. | 30 min p.i. | 60 min p.i. |
| Title substance from Example 2 | 3 ± 2 | 4 ± 4 | 5 ± 3 | 3 ± 2 |
| Title substance from Example 22 | 3 ± 1 | 7 ± 3 | 4 ± 1 | 4 ± 1 |

Example 35

Excretion after Intravenous Administration in Rats

After intravenous administration of 50 μmol of total gadolinium/kg of body weight of substances from Examples 2c), 21 c) and 22 c) in rats (n=3), the metal content was determined fractionally up to 14 days after administration by means of atomic emission spectrometry (ICP-AES) in the excretion medium urine and faeces, and in the body (rest of body) (Table 3).

TABLE 3

Excretion after administration of the substances from Examples 2 c), 21 c) and 22 c).

| | Gd content [% dose] | | |
|---|---|---|---|
| | urea | faeces | rest of body |
| Title substance from Example 2 | 0.8 ± 0.2 | 92.9 ± 1.5 | 0.2 ± 0.3 |
| Title substance from Example 21 | 3.8 ± 0.1 | 84.9 ± 0.7 | 0.0 ± 0.0 |
| Title substance from Example 22 | 1.8 ± 0.1 | 83.4 ± 2.6 | 0.0 ± 0.0 |

Example 36

Plasma Kinetics after Intravenous Administration in Rats

After intravenous administration of 50 μmol of total gadolinium/kg of body weight of the substances from Examples 2c), 21 c) and 22 c) in rats (n=3), blood samples were taken at different points in time (up to 24 h p.i.) by means of a catheter in the common carotid artery, and the metal content was determined by means of atomic emission spectrometry (ICP-AES) and converted to plasma values by means of a conversion factor (0.625). The pharmacokinetic parameters (Table 4) were calculated from the plasma concentrations by means of special software (WinNonlin).

TABLE 4

Plasma kinetics after administration of the substances from Examples 2 c), 21 c) and 22 c).

|  |  | Title substance from Example 2 | Title substance from Example 21 | Title substance from Example 22 |
| --- | --- | --- | --- | --- |
| α-t½ | min | 18.7 ± 2.0 | 28.4 ± 1.5 | 23.6 ± 0.6 |
| β-t½ | h | 1.2 ± 0.2 | 1.3 ± 0.2 | 1.8 ± 0.3 |
| Vc | l/kg | 0.05 ± 0.00 | 0.04 ± 0.00 | 0.04 ± 0.00 |
| Vd ss | l/kg | 0.08 ± 0.01 | 0.05 ± 0.00 | 0.06 ± 0.00 |
| Total Clearance | ml/min * kg | 1.60 ± 0.07 | 0.83 ± 0.11 | 1.13 ± 0.11 |

Example 37

MRT Demonstration of Lymph Nodes after Intravenous Administration in Rats

The figures show exemplary MR shots of popliteal lymph nodes at different points in time after intravenous administration of 50 μmol of Gd/kg of body weight of the substance from Example 2c) in FIG. 1, of the substance from Example 21 c) in FIG. 2, and of the substance from Example 22 c) in FIG. 3 in rats. The $T_1$-weighted turbo spin-echo shots (1.5 T; sequence: T1-TSE; TR 451 ms, TE 8.7 ms) illustrate the strong signal increase in the functional lymph node tissue at early points in time (up to 60 min p.i.).

Figure 1:
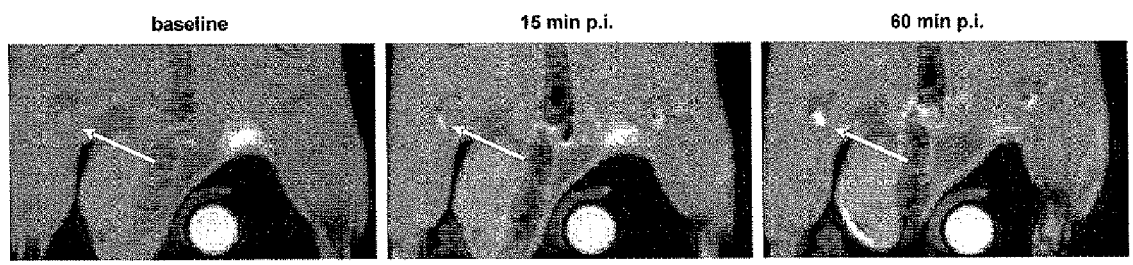
FIG. 1 is three MR shots (images)
Figure 2:
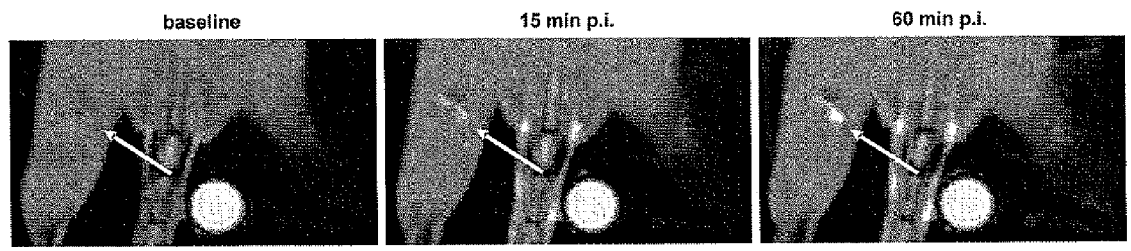
FIG. 2 is three MR shots (images)
Figure 3:
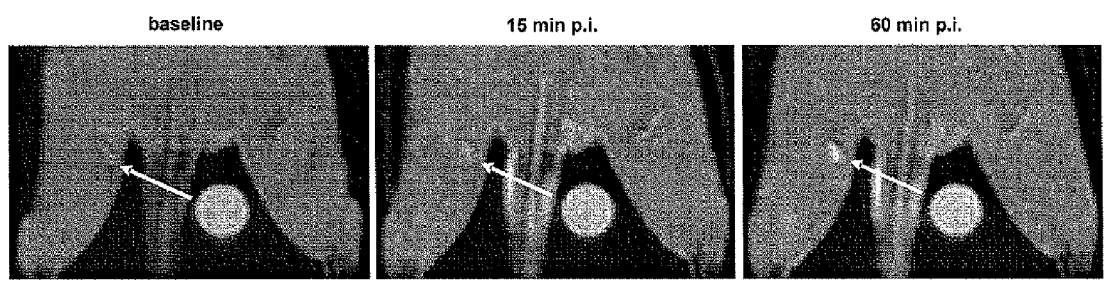
FIG. 3 is three MR shots (images)

The invention claimed is:
1. A metal chelate selected from:
6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine-[N-methyl-(1H,1H,2H,2H,4H,4H,-3,6,9,12-tetraoxaperfluoro-hexadecyl)]amide, complexes with at least one metal ion equivalent of atomic number 57-83;
1,4,7-Tris(carboxylatomethyl)-10-[(3-aza-4-oxo-5-methyl-5-yl)-acid N-(1H,1H,2H, 2H,-4H,4H,-3,6,9,12-tetraoxaperfluorohexadecyl)-N-(2-methoxyethyl)amide]-1,4,7,10-tetra-azacyclododecane, complexes with at least one metal ion equivalent of atomic number 57-83;
6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(1H,1H,2H,2H,4H,4H,-3,6,9,12-tetraoxaperfluoro-tridecyl)]amide, complexes with at least one metal ion equivalent of atomic number 57-83;
1,4,7-Tris(carboxylatomethyl)-10-[(3-aza-4-oxo-5-methyl-5-yl)acid N-(1H,1H,2H,2H,-4H,4H,-3,6,9,12-tetraoxaperfluorotridecyl)-N-(2-methoxyethyl)amide]1,4,7,10-tetra-azacyclododecane, complexes with at least one metal ion equivalent of atomic number 57-83;
6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(2H,2H,4H,4H,-3,6,9,12-tetraoxa-5,8,11-trimethyl-perfluoropentadecyl)]amide, complexes with at least one metal ion equivalent of atomic number 57-83;
1,4,7-Tris(carboxylatomethyl)-10-[(3-aza-4-oxo-5-methyl-5-yl)acid N-(2H,2H,4H, 4H,-3,6,9,12-tetraoxa-5,8,11-trimethylperfluoropentadecyl)-N-(2-methoxyethyl)amide]1,4,7,10-tetra-azacyclododecane, complexes with at least one metal ion equivalent of atomic number 57-83;
6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(3,6,9,12,15-pentaoxa-5,8,11,14-tetramethyl-perfluorooctadecyl)]amide, complexes with at least one metal ion equivalent of atomic number 57-83;
1,4,7-Tris(carboxylatomethyl)-10-[(3-aza-4-oxo-5-methyl-5-yl)acid N-(3,6,9,12,15-pentaoxa-5,8,11,14-tetramethylperfluorooctadecyl)-N-(2-methoxyethyl)amide]1,4,7,10-tetra-azacyclododecane, complexes with at least one metal ion equivalent of atomic number 57-83;
N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-3,6,9,12-tetraoxa-perfluorotridecyl)-2-[2-(2-methoxyethoxy)ethoxy]acetamide, complexes with at least one metal ion equivalent of atomic number 57-83;
N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-6,9,12,15-tetraoxa-8,11,14-trimethylperfluoropentadecyl)-2-[2-(2-methoxyethoxy)ethoxy]-acetamide, complexes with at least one metal ion equivalent of atomic number 57-83;
6-N-(1-O-α-d-Carbonylmethylmannopyranose)-2-N-(2H,2H,4H,4H-3,6,9,12,-tetraoxaperfluorotridecanoyl)-L-lysine[1,4,7-tris-(carboxylatomethyl)-1,4,7,10-tetraazacyclododecane-10-N-(2-hydroxy-3-yl)]amide, complexes with at least one metal ion equivalent of atomic number 57-83;
6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine[1,4,7-tris-(carboxylatomethyl)-1,4,7,10-tetraazacyclododecane-10-N-(2-hydroxy-3-yl)]amide, complexes with at least one metal ion equivalent of atomic number 57-83;

6-N-[1,4,7-Tris(carboxylatomethyl)-1,4,7,10-tetraazacyclododecane-10-N-(pentanoyl-3-aza-4-oxo-5-methyl-5-yl)]-2-N-(2H,2H,4H,4H-3,6,9,12,-tetraoxa-perfluorotridecanoyl)-L-lysine(2-{2-[2-(2-methoxyethoxy)ethoxy]ethoxy}ethyl)amide, complexes with at least one metal ion equivalent of atomic number 57-83;

3,5-N,N'-Bis[1,4,7-tris(carboxylatomethyl)-1,4,7,10-tetraazacyclododecane-10-N-(pentanoyl-3-aza-4-oxo-5-methyl-5-yl)]-benzoic acid [(1H,1H,2H,2H,4H,4H,-3,6,9,12-tetraoxaperfluorotridecyl)methyl]amide, complexes with at least one metal ion equivalent of atomic number 57-83;

N-[1,4,7-Tris(carboxylatomethyl)-1,4,7,10-tetraazacyclododecane-10-N-(pentanoyl-3aza-4-oxo-5-methyl-5-yl)]-3-{2-[2-(2-methoxyethoxy)ethoxy]ethyl}-L-serine 1-[(1H,1H,2H,2H,4H,4H,-3,6,9,12-tetraoxaperfluorotridecyl)methyl]amide, complexes with at least one metal ion equivalent of atomic number 57-83;

L-Glutamic acid 5-{[1,4,7-tris(carboxylatomethyl)-1,4,7,10-tetraazacyclododecane-10-N-(2-hydroxy-3-yl)]amido}-N-(2-{2-[2-(2-methoxyethoxy)ethoxy]ethoxy}acetyl)-1-[(1H,1H,2H,2H,4H,4H,-3,6,9,12-tetraoxaperfluorotridecyl)methyl]amide, complexes with at least one metal ion equivalent of atomic number 57-83;

N-[1,4,7-Tris(carboxylatomethyl)-1,4,7,10-tetraazacyclododecane-10-N-(pentanoyl-3-aza-4-oxo-5-methyl-5-yl)]-L-glutamic acid 5-(2-{2-[2-(2-methoxyethoxy)ethoxy]-ethoxy}ethyl)amide 1-[(1H,1H,2H,2H,4H,4H,-3,6,9,12-tetraoxaperfluorotridecyl)-methyl]amide, complexes with at least one metal ion equivalent of atomic number 57-83;

L-2-[1,4,7-Tris(carboxylatomethyl)-1,4,7,10-tetraazacyclododecane-10-N-(pentanoyl-3-aza-4-oxo-5-methyl-5-yl)]-amino-4-(2-{2-[2-(2-methoxyethoxy)ethoxy]-ethoxy}acetyl)aminobutyric acid [(1H,1H,2H,2H,4H,4H,-3,6,9,12-tetraoxaperfluoro-tridecyl)methyl]amide, complexes with at least one metal ion equivalent of atomic number 57-83;

2-N-[1,4,7-Tris(carboxylatomethyl)-1,4,7,10-tetraazacyclododecane-10-N-(pentanoyl-3-aza-4-oxo-5-methyl-5-yl)]-6-N-benzyloxycarbonyl-L-lysine[N-methyl-(1H,1H,2H,2H,4H,4H,-3,6,9,12-tetraoxaperfluorohexadecyl)]amide, complexes with at least one metal ion equivalent of atomic number 57-83;

2-N-[1,4,7-Tris(carboxylatomethyl)-1,4,7,10-tetraazacyclododecane-10-N-(pentanoyl-3-aza-4-oxo-5-methyl-5-yl)]-L-lysine[N-methyl-(1H,1H,2H,2H,4H,4H,-3,6,9,12-tetraoxaperfluorohexadecyl)]amide, complexes with at least one metal ion equivalent of atomic number 57-83;

2-N-[1,4,7-Tris(carboxylatomethyl)-1,4,7,10-tetraazacyclododecane-10-N-(pentanoyl-3-aza-4-oxo-5-methyl-5-yl)]-6-N-(1-O-α-d-carbonylmethylmannopyranose)-L-lysine[N-methyl-(1H,1H,2H,2H,4H,4H,-3,6,9,12-tetraoxaperfluorohexadecyl)]amide, complexes with at least one metal ion equivalent of atomic number 57-83;

2-N-[1,4,7-Tris(carboxylatomethyl)-1,4,7,10-tetraazacyclododecane-10-N-(pentanoyl-3-aza-4-oxo-5-methyl-5-yl)]-6-N-{2-[2-(2-methoxyethoxy)ethoxy]acetyl}-L-lysine[N-methyl-(1H,1H,2H,2H,4H,4H,-3,6,9,12-tetraoxaperfluorohexadecyl)]-amide, complexes with at least one metal ion equivalent of atomic number 57-83;

1,4,7-Tris(carboxylatomethyl)-10-{(3-aza-4-oxo-5-methyl-5-yl)-acid-N-(1H,1H,2H,2H,-4H,4H,-3,6,9,12-tetraoxaperfluorohexadecyl)-N-[2-(2-methoxyethoxy)ethyl]amide}-1,4,7,10-tetraazacyclododecane, complexes with at least one metal ion equivalent of atomic number 57-83;

1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorohexadecyl)-N-{2-[2-(2-methoxyethoxy)ethoxy]-ethyl}amide]1,4,7,10-tetraazacyclododecane, complexes with at least one metal ion equivalent of atomic number 57-83;

1,4,7-Tris(carboxylatomethyl)-10-{[(3-aza-4-oxo-5-methyl-5-yl)acid N-(1H,1H,2H, 2H,-4H,4H,-3,6,9,12-tetraoxaperfluorohexadecyl)-N-[2-(1-O-α-d-mannopyranosyl)ethyl]amide}1,4,7,10-tetraazacyclododecane, complexes with at least one metal ion equivalent of atomic number 57-83;

1,4,7-Tris(carboxylatomethyl)-10-[(4-hydroxy-5-yl)acid N-(1H,1H,2H,2H,4H,4H,-3,6,9,12-tetraoxaperfluorohexadecyl)-N-(2-methoxyethyl)amide]1,4,7,10-tetraaza-cyclododecane, complexes with at least one metal ion equivalent of atomic number 57-83;

1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorohexadecyl)-N-(2-methoxyethyl)amide]-1,4,7,10-tetra-azacyclododecane, complexes with at least one metal ion equivalent of atomic number 57-83;

1,4,7-Tris(carboxylatomethyl)-10-[(3-aza-4-oxo-5-methyl-5-yl)acid N-(1H,1H,2H, 2H,-4H,4H,-3,6,9,12-tetraoxaperfluorohexadecyl)-N-(2-methoxyethyl)amide] 1,4,7,10-tetra-azacyclododecane, complexes with at least one metal ion equivalent of atomic number 57-83;

5-[bis(2-{[1-(sodium sulphonatobutyl)-3-hydroxy-6-methyl-2-oxo-1,2-dihydropyridine-4-carbonyl]amino}ethyl)amino]-4-{[1-(sodium sulphonato-butyl)-3-hydroxy-6-methyl-2-oxo-1,2-dihydropyridine-4-carbonyl]amino}pentane-carboxylic acid [N-(1H,1H,2H,2H,4H,4H,-3,6,9,12-tetraoxaperfluorohexadecyl)-N-(2-methoxyethyl)]amide, complexes with at least one metal ion equivalent of atomic number 57-83; and 6-N-(2,3-Dihydroxy-N-{[bis(2-{[1-(sodium sulphonatobutyl)-3-hydroxy-6-methyl-2-oxo-1,2-dihydropyridine-4-carbonyl]amino}ethyl)amino]ethyl}-terephthalyl)-2-N-(1-O-α-d-carbonylmethylmannopyranose)-L-lysine[N-methyl-(1H,1H,2H,2H,4H,4H,-3,6,9,12-tetraoxaperfluorohexadecyl)]amide, complexes with at least one metal ion equivalent of atomic number 57-83; and salts thereof.

2. A metal chelate according to claim 1, wherein said metal chelate is selected from:

6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine-[N-methyl-(1H,1H,2H,2H,4H,4H,-3,6,9,12-tetraoxaperfluoro-hexadecyl)]amide, Gd complex;

1,4,7-Tris(carboxylatomethyl)-10-[(3-aza-4-oxo-5-methyl-5-yl)-acid N-(1H,1H,2H, 2H,-4H,4H,-3,6,9,12-tetraoxaperfluorohexadecyl)-N-(2-methoxyethyl)amide]-1,4,7,10-tetra-azacyclododecane, Gd complex;

6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(1H,1H,2H,2H,4H,4H,-3,6,9,12-tetraoxaperfluoro-tridecyl)]amide, Gd complex;

1,4,7-Tris(carboxylatomethyl)-10-[(3-aza-4-oxo-5-methyl-5-yl)acid N-(1H,1H,2H,2H, -4H,4H,-3,6,9,12-tetraoxaperfluorotridecyl)-N-(2-methoxyethyl)amide]1,4,7,10-tetra-azacyclododecane, Gd complex;

6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(2H,2H,4H,4H,-3,6,9,12-tetraoxa-5,8,11-trimethyl-perfluoropentadecyl)]amide, Gd complex;

1,4,7-Tris(carboxylatomethyl)-10-[(3-aza-4-oxo-5-methyl-5-yl)acid N-(2H,2H,4H, 4H,-3,6,9,12-tetraoxa-5,8,11-trimethylperfluoropentadecyl)-N-(2-methoxyethyl)amide]1,4,7,10-tetra-azacyclododecane, Gd complex;

6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(3,6,9,12,15-pentaoxa-5,8,11,14-tetramethyl-perfluorooctadecyl)]amide, Gd complex;

1,4,7-Tris(carboxylatomethyl)-10-[(3-aza-4-oxo-5-methyl-5-yl)acid N-(3,6,9,12,15-pentaoxa-5,8,11,14-tetramethylperfluorooctadecyl)-N-(2-methoxyethyl)amide]1,4,7,10-tetra-azacyclododecane, Gd complex;

N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,4H,4H-3,6,9,12-tetraoxa-perfluorotridecyl)-2-[2-(2-methoxyethoxy)ethoxy]acetamide, Gd complex;

N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-6,9,12,15-tetraoxa-8,11,14-trimethylperfluoropentadecyl)-2-[2-(2-methoxyethoxy)ethoxy]-acetamide, Gd complex;

6-N-(1-O-α-d-Carbonylmethylmannopyranose)-2-N-(2H,2H,4H,4H-3,6,9,12,-tetraoxaperfluorotridecanoyl)-L-lysine[1,4,7-tris-(carboxylatomethyl)-1,4,7,10-tetraazacyclododecane-10-N-(2-hydroxy-3-yl)]amide, Gd complex;

6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine[1,4,7-tris-(carboxylatomethyl)-1,4,7,10-tetraazacyclododecane-10-N-(2-hydroxy-3-yl)]amide, Gd complex;

6-N-[1,4,7-Tris(carboxylatomethyl)-1,4,7,10-tetraazacyclododecane-10-N-(pentanoyl-3-aza-4-oxo-5-methyl-5-yl)]-2-N-(2H,2H,4H,4H-3,6,9,12,-tetraoxa-perfluorotridecanoyl)-L-lysine(2-{2-[2-(2-methoxyethoxy)ethoxy]ethoxy}ethyl)amide, Gd complex;

3,5-N,N'-Bis[1,4,7-tris(carboxylatomethyl)-1,4,7,10-tetraazacyclododecane-10-N-(pentanoyl-3-aza-4-oxo-5-methyl-5-yl)]benzoic acid [(1H,1H,2H,2H,4H,4H,-3,6,9,12-tetraoxaperfluorotridecyl)methyl]amide, Gd complex;

N-[1,4,7-Tris(carboxylatomethyl)-1,4,7,10-tetraazacyclododecane-10-N-(pentanoyl-3-aza-4-oxo-5-methyl-5-yl)]-3-{2-[2-(2-methoxyethoxy)ethoxy]ethyl}-L-serine 1-[(1H,1H,2H,2H,4H,4H,-3,6,9,12-tetraoxaperfluorotridecyl)methyl]amide, Gd complex;

L-Glutamic acid 5-{[1,4,7-tris(carboxylatomethyl)-1,4,7,10-tetraazacyclododecane-10-N-(2-hydroxy-3-yl)]amido}-N-(2-{2-[2-(2-methoxyethoxy)ethoxy]ethoxy}acetyl)-1-[(1H,1H,2H,2H,4H,4H,-3,6,9,12-tetraoxaperfluorotridecyl)methyl]amide, Gd complex;

N-[1,4,7-Tris(carboxylatomethyl)-1,4,7,10-tetraazacyclododecane-10-N-(pentanoyl-3-aza-4-oxo-5-methyl-5-yl)]-L-glutamic acid 5-(2-{2-[2-(2-methoxyethoxy)ethoxy]-ethoxy}ethyl)amide 1-[(1H,1H,2H,2H,4H,4H,-3,6,9,12-tetraoxaperfluorotridecyl)-methyl]amide, Gd complex;

L-2-[1,4,7-Tris(carboxylatomethyl)-1,4,7,10-tetraazacyclododecane-10-N-(pentanoyl-3-aza-4-oxo-5-methyl-5-yl)]-amino-4-(2-{2-[2-(2-methoxyethoxy)ethoxy]ethoxy}acetyl)aminobutyric acid [(1H,1H,2H,2H,4H,4H,-3,6,9,12-tetraoxaperfluoro-tridecyl)methyl]amide, Gd complex;

2-N-[1,4,7-Tris(carboxylatomethyl)-1,4,7,10-tetraazacyclododecane-10-N-(pentanoyl-3-aza-4-oxo-5-methyl-5-yl)]-6-N-benzyloxycarbonyl-L-lysine[N-methyl-(1H,1H,2H,2H,4H,4H,-3,6,9,12-tetraoxaperfluorohexadecyl)]amide, Gd complex;

2-N-[1,4,7-Tris(carboxylatomethyl)-1,4,7,10-tetraazacyclododecane-10-N-(pentanoyl-3-aza-4-oxo-5-methyl-5-yl)]-L-lysine[N-methyl-(1H,1H,2H,2H,4H,4H,-3,6,9,12-tetraoxaperfluorohexadecyl)]amide, Gd complex;

2-N-[1,4,7-Tris(carboxylatomethyl)-1,4,7,10-tetraazacyclododecane-10-N-(pentanoyl-3-aza-4-oxo-5-methyl-5-yl)]-6-N-(1-O-α-d-carbonylmethylmannopyranose)-L-lysine[N-methyl-(1H,1H,2H,2H,4H,4H,-3,6,9,12-tetraoxaperfluorohexadecyl)]amide, Gd complex;

2-N-[1,4,7-Tris(carboxylatomethyl)-1,4,7,10-tetraazacyclododecane-10-N-(pentanoyl-3-aza-4-oxo-5-methyl-5-yl)]-6-N-[2-[2-(2-methoxyethoxy)ethoxy]acetyl}-L-lysine[N-methyl-(1H,1H,2H,2H,4H,4H,-3,6,9,12-tetraoxaperfluorohexadecyl)]-amide, Gd complex;

1,4,7-Tris(carboxylatomethyl)-10-{(3-aza-4-oxo-5-methyl-5-yl)-acid-N-(1H,1H,2H,2H,-4H,4H,-3,6,9,12-tetraoxaperfluorohexadecyl)-N-[2-(2-methoxyethoxy)ethyl]amide}-1,4,7,10-tetraazacyclododecane, Gd complex; 1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorohexadecyl)-N-{2-[2-(2-methoxyethoxy)ethoxy]-ethyl}amide]1,4,7,10-tetraazacyclododecane, Gd complex;

1,4,7-Tris(carboxylatomethyl)-10-{[(3-aza-4-oxo-5-methyl-5-yl)acid N-(1H,1H,2H, 2H,-4H,4H,-3,6,9,12-tetraoxaperfluorohexadecyl)-N-[2-(1-O-α-d-mannopyranosyl)ethyl]amide}1,4,7,10-tetraazacyclododecane, Gd complex;

1,4,7-Tris(carboxylatomethyl)-10-[(4-hydroxy-5-yl)acid N-(1H,1H,2H,2H,4H,4H,-3,6,9,12-tetraoxaperfluorohexadecyl)-N-(2-methoxyethyl)amide]1,4,7,10-tetraaza-cyclododecane, Gd complex;

1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorohexadecyl)-N-(2-methoxyethyl)amide]-1,4,7,10-tetra-azacyclododecane, Dy complex;

1,4,7-Tris(carboxylatomethyl)-10-[(3-aza-4-oxo-5-methyl-5-yl)acid N-(1H,1H,2H, 2H,-4H,4H,-3,6,9,12-tetraoxaperfluorohexadecyl)-N-(2-methoxyethyl)amide]1,4,7,10-tetra-azacyclododecane, Yb complex;

5-[bis(2-{[1-(sodium sulphonatobutyl)-3-hydroxy-6-methyl-2-oxo-1,2-dihydropyridine-4-carbonyl]amino}ethyl)amino]-4-{[1-(sodium sulphonato-butyl)-3-hydroxy-6-methyl-2-oxo-1,2-dihydropyridine-4-carbonyl]amino}pentane-carboxylic acid [N-(1H,1H,2H,2H,4H,4H,-3,6,9,12-tetraoxaperfluorohexadecyl)-N-(2-methoxyethyl)]amide, Gd complex; and 6-N-(2,3-Dihydroxy-N-{[bis(2-{[1-(sodium sulphonatobutyl)-3-hydroxy-6-methyl-2-oxo-1,2-dihydropyridine-4-carbonyl]amino}ethyl)amino]ethyl}-terephthalyl)-2-N-(1-O-α-d-carbonylmethylmannopyranose)-L-lysine[N-methyl-(1H,1H,2H,2H,4H,4H,-3,6,9,12-tetraoxaperfluorohexadecyl)]amide, Gd complex;
and salts thereof.

3. A metal chelate according to claim 1, wherein said metal chelate is a 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine-[N-methyl-(1H,1H,2H,2H,4H,4H,-3,6,9,12-tetraoxaperfluoro-hexadecyl)]amide, complex with at least one metal ion equivalent of atomic number 57-83 or a salt thereof.

4. A metal chelate according to claim 1, wherein said metal chelate is a 1,4,7-Tris(carboxylatomethyl)-10-[(3-aza-4-oxo-5-methyl-5-yl)-acid N-(1H,1H,2H, 2H,4H,4H,-3,6,9,12-tetraoxaperfluorohexadecyl)-N-(2-methoxyethyl)amide]-1,4,7,10-tetra-azacyclododecane, complex with at least one metal ion equivalent of atomic number 57-83 or a salt thereof.

5. A metal chelate according to claim 1, wherein said metal chelate is a 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(1H,1H,2H,2H,4H,4H,-3,6,9,12-tetraoxaperfluoro-tridecyl)]amide, complex with at least one metal ion equivalent of atomic number 57-83 or a salt thereof.

6. A metal chelate according to claim 1, wherein said metal chelate is a 1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorotridecyl)-N-(2-methoxyethyl)amide]1,4,7,10-tetraazacyclododecane, complex with at least one metal ion equivalent of atomic number 57-83 or a salt thereof.

7. A metal chelate according to claim 1, wherein said metal chelate is a 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(2H,2H,4H,4H,-3,6,9,12-tetraoxa-5,8,11-trimethyl-perfluoropentadecyl)]amide, complex with at least one metal ion equivalent of atomic number 57-83 or a salt thereof.

8. A metal chelate according to claim 1, wherein said metal chelate is a 1,4,7-Tris(carboxylatomethyl)-10-[(3-aza-4-oxo-5-methyl-5-yl)acid N-(2H,2H,4H, 4H,-3,6,9,12-tetraoxa-5,8,11-trimethylperfluoropentadecyl)-N-(2-methoxyethyl)amide]1,4,7,10-tetra-azacyclododecane, complex with at least one metal ion equivalent of atomic number 57-83 or a salt thereof.

9. A metal chelate according to claim 1, wherein said metal chelate is a 6-N-[1,4,7-Tris(carboxylatomethyl)-1,4,7,10-tetraazacyclododecane-10-N-(pentanoyl-3-aza-4-oxo-5-methyl-5-yl)]-2-N-(1-O-α-d-carbonylmethylmannopyranose)-L-lysine[N-methyl-(3,6,9,12,15-pentaoxa-5,8,11,14-tetramethyl-perfluorooctadecyl)]amide, complex with at least one metal ion equivalent of atomic number 57-83 or a salt thereof.

10. A metal chelate according to claim 1, wherein said metal chelate is a 1,4,7-Tris(carboxylatomethyl)-10-[(3-aza-4-oxo-5-methyl-5-yl)acid N-(3,6,9,12,15-pentaoxa-5,8,11,14-tetramethylperfluorooctadecyl)-N-(2-methoxyethyl)amide]1,4,7,10-tetra-azacyclododecane, complex with at least one metal ion equivalent of atomic number 57-83 or a salt thereof.

11. A metal chelate according to claim 1, wherein said metal chelate is a N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-3,6,9,12-tetraoxaperfluorotridecyl)-2-[2-(2-methoxyethoxy)ethoxy]acetamide, complex with at least one metal ion equivalent of atomic number 57-83 or a salt thereof.

12. A metal chelate according to claim 1, wherein said metal chelate is a N-{[1,4,7-Tris(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H-6,9,12,15-tetraoxa-8,11,14-trimethyl-perfluoropentadecyl)-2-[2-(2-methoxyethoxy)ethoxy]-acetamide, complex with at least one metal ion equivalent of atomic number 57-83 or a salt thereof.

13. A metal chelate according to claim 1, wherein said metal chelate is a 6-N-(1-O-α-d-Carbonylmethylmannopyranose)-2-N-(2H,2H,4H,4H-3,6,9,12,-tetraoxaperfluorotridecanoyl)-L-lysine[1,4,7-tris-(carboxylatomethyl)-1,4,7,10-tetraazacyclododecane-10-N-(2-hydroxy-3-yl)]amide, complex with at least one metal ion equivalent of atomic number 57-83 or a salt thereof.

14. A metal chelate according to claim 1, wherein said metal chelate is a 6-N-{2-[2-(2-Methoxyethoxy)ethoxy]acetyl}-2-N-(2H,2H,4H,4H-3,6,9,12,-tetraoxa-5,8,11-trimethylperfluoropentadecanoyl)-L-lysine[1,4,7-tris-(carboxylatomethyl)-1,4,7,10-tetraazacyclododecane-10-N-(2-hydroxy-3-yl)]amide, complex with at least one metal ion equivalent of atomic number 57-83 or a salt thereof.

15. A metal chelate according to claim 1, wherein said metal chelate is a 6-N-[1,4,7-Tris(carboxylatomethyl)-1,4,7,10-tetraazacyclododecane-10-N-(pentanoyl-3-aza-4-oxo-5-methyl-5-yl)]-2-N-(2H,2H,4H,4H-3,6,9,12,-tetraoxa-perfluorotridecanoyl)-L-lysine(2-{2-[2-(2-methoxyethoxy)ethoxy]ethoxy}ethyl)amide, complex with at least one metal ion equivalent of atomic number 57-83 or a salt thereof.

16. A metal chelate according to claim 1, wherein said metal chelate is a 3,5-N,N'-Bis[1,4,7-tris(carboxylatomethyl)-1,4,7,10-tetraazacyclododecane-10-N-(pentanoyl-3-aza-4-oxo-5-methyl-5-yl)]benzoic acid [(1H,1H,2H,2H,4H,4H,-3,6,9,12-tetraoxaperfluorotridecyl)methyl]amide, complex with at least one metal ion equivalent of atomic number 57-83 or a salt thereof.

17. A metal chelate according to claim 1, wherein said metal chelate is a N-[1,4,7-Tris(carboxylatomethyl)-1,4,7,10-tetraazacyclododecane-10-N-(pentanoyl-3-aza-4-oxo-5-methyl-5-yl)]-3-{2-[2-(2-methoxyethoxy)ethoxy]ethyl}-L-serine 1-[(1H,1H,2H,2H,4H,4H,-3,6,9,12-tetraoxaperfluorotridecyl)methyl]amide, complex with at least one metal ion equivalent of atomic number 57-83 or a salt thereof.

18. A metal chelate according to claim 1, wherein said metal chelate is a L-Glutamic acid 5-{[1,4,7-tris(carboxylatomethyl)-1,4,7,10-tetraazacyclododecane-10-N-(2-hydroxy-3-yl)]amido}-N-(2-{2-[2-(2-methoxyethoxy)ethoxy}acetyl)-1-[(1H,1H,2H,2H,4H,4H,-3,6,9,12-tetraoxaperfluorotridecyl)methyl]amide, complex with at least one metal ion equivalent of atomic number 57-83 or a salt thereof.

19. A metal chelate according to claim 1, wherein said metal chelate is a N-[1,4,7-Tris(carboxylatomethyl)-1,4,7,10-tetraazacyclododecane-10-N-(pentanoyl-3-aza-4-oxo-5-methyl-5-yl)]-L-glutamic acid 5-(2-{2-[2-(2-methoxyethoxy)ethoxy]-ethoxy}ethyl)amide 1-[(1H,1H,2H,2H,4H,4H,-3,6,9,12-tetraoxaperfluorotridecyl)-methyl]amide, complex with at least one metal ion equivalent of atomic number 57-83 or a salt thereof.

20. A metal chelate according to claim 1, wherein said metal chelate is a L-2-[1,4,7-Tris(carboxylatomethyl)-1,4,7,10-tetraazacyclododecane-10-N-(pentanoyl-3-aza-4-oxo-5-methyl-5-yl)]-amino-4-(2-{2-[2-(2-methoxyethoxy)ethoxy]-ethoxy}acetyl)aminobutyric acid [(1H,1H,2H,2H,4H,4H,-3,6,9,12-tetraoxaperfluoro-tridecyl)methyl]amide, complex with at least one metal ion equivalent of atomic number 57-83 or a salt thereof.

21. A metal chelate according to claim 1, wherein said metal chelate is a 2-N-[1,4,7-Tris(carboxylatomethyl)-1,4,7, 10-tetraazacyclododecane-10-N-(pentanoyl-3-aza-4-oxo-5-methyl-5-yl)]-6-N-benzyloxycarbonyl-L-lysine[N-methyl-(1H,1H,2H,2H,4H,4H,-3,6,9,12-tetraoxaperfluorohexadecyl)]amide, complex with at least one metal ion equivalent of atomic number 57-83 or a salt thereof.

22. A metal chelate according to claim 1, wherein said metal chelate is a 2-N-[1,4,7-Tris(carboxylatomethyl)-1,4,7,10-tetraazacyclododecane-10-N-(pentanoyl-3-aza-4-oxo-5-methyl-5-yl)]-L-lysine[N-methyl-(1H,1H,2H,2H,4H,4H,-3,6,9,12-tetraoxaperfluorohexadecyl)]amide, complex with at least one metal ion equivalent of atomic number 57-83 or a salt thereof.

23. A metal chelate according to claim 1, wherein said metal chelate is a 2-N-[1,4,7-Tris(carboxylatomethyl)-1,4,7,10-tetraazacyclododecane-10-N-(pentanoyl-3-aza-4-oxo-5-methyl-5-yl)]-6-N-(1-O-α-d-carbonylmethylmannopyranose)-L-lysine[N-methyl-(1H,1H,2H,2H,4H,4H,-3,6,9,12-tetraoxaperfluorohexadecyl)]amide, complex with at least one metal ion equivalent of atomic number 57-83 or a salt thereof.

24. A metal chelate according to claim 1, wherein said metal chelate is a 2-N-[1,4,7-Tris(carboxylatomethyl)-1,4,7,10-tetraazacyclododecane-10-N-(pentanoyl-3-aza-4-oxo-5-methyl-5-yl)]-6-N-{2-[2-(2-methoxyethoxy)ethoxy]acetyl}-L-lysine[N-methyl-(1H,1H,2H,2H,4H,4H,-3,6,9,12-tetraoxaperfluorohexadecyl)]-amide, complex with at least one metal ion equivalent of atomic number 57-83 or a salt thereof.

25. A metal chelate according to claim 1, wherein said metal chelate is a 1,4,7-Tris(carboxylatomethyl)-10-{(3-aza-4-oxo-5-methyl-5-yl)-acid-N-(1H,1H,2H,2H,4H,4H,-3,6,9,12-tetraoxaperfluorohexadecyl)-N-[2-(2-methoxyethoxy)ethyl]amide}-1,4,7,10-tetra-azacyclododecane, complex with at least one metal ion equivalent of atomic number 57-83 or a salt thereof.

26. A metal chelate according to claim 1, wherein said metal chelate is a 1,4,7-Tris(carboxylatomethyl)-10-[(3-aza-4-oxo-5-methyl-5-yl)acid N-(1H,1H,2H,2H, 4H,4H,-3,6,9,12-tetraoxaperfluorohexadecyl)-N-{2-[2-(2-methoxyethoxy)ethoxy]-ethyl}amide]1,4,7,10-tetraazacyclododecane, complex with at least one metal ion equivalent of atomic number 57-83 or a salt thereof.

27. A metal chelate according to claim 1, wherein said metal chelate is a 1,4,7-Tris(carboxylatomethyl)-10-{[(3-aza-4-oxo-5-methyl-5-yl)acid N-(1H,1H,2H, 2H,4H,4H,-3,6,9,12-tetraoxaperfluorohexadecyl)-N-[2-(1-O-α-d-mannopyranosyl)ethyl]amide}1,4,7,10-tetraazacyclododecane, complex with at least one metal ion equivalent of atomic number 57-83 or a salt thereof.

28. A metal chelate according to claim 1, wherein the metal ion equivalent is an element of atomic number 62, 64, 70, 75 or 77.

29. A metal chelate according to claim 1, wherein the metal ion equivalent is selected from praseodymium(III), neodymium(III), samarium(III), gadolinium(III), ytterbium(III), bismuth(III), dysprosium(III) and yttrium(III).

30. A metal chelate according to claim 1, wherein the metal ion equivalent is selected from praseodymium(III), neodymium(III), samarium(III), ytterbium(III), gadolinium(III), terbium(III), dysprosium(III), holmium(III), and erbium(III).

31. A pharmaceutical composition comprising at least one metal chelate according to claim 1, and at least one customary galenic additive.

* * * * *

UNITED STATES PATENT AND TRADEMARK OFFICE
CERTIFICATE OF CORRECTION

PATENT NO.          : 8,263,040 B2
APPLICATION NO.     : 11/873986
DATED               : September 11, 2012
INVENTOR(S)         : Johannes Platzek et al.

It is certified that error appears in the above-identified patent and that said Letters Patent is hereby corrected as shown below:

In the Claims:

Column 88, line 30 (Claim 2), reads: "complex; 1,4,7-Tris(carboxylatomethyl)-10-[3-aza-4-"
It should read: -- complex;
       1,4,7-Tris(carboxylatomethyl)-10-[3-aza-4- --.

Column 92, line 24 (Claim 29), reads: "bismuth (III), dysprosium (III) and yttrium (III)."
It should read: -- bismuth (III) and dysprosium (III). --.

Signed and Sealed this
Fifth Day of February, 2013

Teresa Stanek Rea
*Acting Director of the United States Patent and Trademark Office*